US011091770B2

(12) United States Patent
Baum et al.

(10) Patent No.: US 11,091,770 B2
(45) Date of Patent: Aug. 17, 2021

(54) COMPOSITIONS AND METHODS FOR CONTROLLING INSECT PESTS

(71) Applicant: Monsanto Technology LLC, St. Louis, MO (US)

(72) Inventors: James A. Baum, Webster Groves, MO (US); Brian D. Eads, Ballwin, MO (US); Jeremy A. Kroemer, Ballwin, MO (US); Christina Marie Taylor, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 15/300,661

(22) PCT Filed: Mar. 27, 2015

(86) PCT No.: PCT/US2015/022985
§ 371 (c)(1),
(2) Date: Sep. 29, 2016

(87) PCT Pub. No.: WO2015/153339
PCT Pub. Date: Oct. 8, 2015

(65) Prior Publication Data
US 2017/0183683 A1    Jun. 29, 2017

Related U.S. Application Data

(60) Provisional application No. 61/973,484, filed on Apr. 1, 2014.

(51) Int. Cl.
*C12N 15/82* (2006.01)
*A01N 63/10* (2020.01)
*A01N 57/16* (2006.01)

(52) U.S. Cl.
CPC ......... *C12N 15/8286* (2013.01); *A01N 57/16* (2013.01); *A01N 63/10* (2020.01); *C12N 15/8218* (2013.01); *C12N 2310/14* (2013.01); *C12N 2320/00* (2013.01); *Y02A 40/146* (2018.01)

(58) Field of Classification Search
CPC .................................................. C12N 15/8286
USPC ........................................................ 800/279
See application file for complete search history.

(56) References Cited

U.S. PATENT DOCUMENTS

| 3,687,808 | A | 8/1972 | Merigan et al. |
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,469,863 | A | 9/1984 | Ts'o et al. |
| 4,476,301 | A | 10/1984 | Imbach et al. |
| 4,535,060 | A | 8/1985 | Comai |
| 4,581,847 | A | 4/1986 | Hibberd et al. |
| 4,666,828 | A | 5/1987 | Gusella |
| 4,683,202 | A | 7/1987 | Mullis |
| 4,732,250 | A | 3/1988 | Maucher et al. |
| 4,761,373 | A | 8/1988 | Anderson et al. |
| 4,769,061 | A | 9/1988 | Comai |
| 4,801,531 | A | 1/1989 | Frossard |
| 4,810,648 | A | 3/1989 | Stalker |
| 4,879,219 | A | 11/1989 | Wands et al. |
| 4,940,835 | A | 7/1990 | Shah et al. |
| 4,971,908 | A | 11/1990 | Kishore et al. |
| 5,004,863 | A | 4/1991 | Umbeck |
| 5,011,771 | A | 4/1991 | Bellet et al. |
| 5,013,659 | A | 5/1991 | Bedbrook et al. |
| 5,015,580 | A | 5/1991 | Christou et al. |
| 5,023,243 | A | 6/1991 | Tullis |

(Continued)

FOREIGN PATENT DOCUMENTS

AU        2008325989 A1    5/2009
AU    AU 2008258254 B2    7/2014
(Continued)

OTHER PUBLICATIONS

Thomas et al. 2001, The Plant Journal 25(4):417-425.*
Yibrah et al. 1993, Hereditas 118:273-2890.*
Arpaia et al., "Production of transgenic eggplant (*Solanum melongena* L.) resistant to Colorado Potato Beetle (*Leptinotarsa decemlineata* Say)," *Theor. Appl. Genet.*, 95:329-334 (1997).
Banerjee et al., "Efficient production of transgenic potato (*S. tuberosum* L. ssp. *andigena*) plants via *Agrobacteriutn tumefaciens*-mediated transformation," *Plant Sci.*, 170(4):732-738 (2006).
(Continued)

*Primary Examiner* — Li Zheng
(74) *Attorney, Agent, or Firm* — Arnold & Porter Kaye Scholer LLP; Amanda Carmany-Rampey; David R. Marsh

(57) ABSTRACT

Disclosed herein are methods of controlling insect pests which infest crop plants, in particular *Spodoptera frugiperda* (fall armyworm), *Lygus hesperus* (western tarnished plant bug), *Euschistus heros* (neotropical brown stink bug), and *Plutella xylostella* (diamondback moth), and methods of providing plants resistant to such pests. Also disclosed are polynucleotides and recombinant DNA molecules and constructs useful in such methods, insecticidal compositions such as topical sprays containing insecticidal double-stranded RNAs, and plants with improved resistance to infestation by these insects. Further disclosed are methods of selecting target genes for RNAi-mediated silencing and control of these insect pests.

15 Claims, 2 Drawing Sheets
Specification includes a Sequence Listing.

(56) References Cited

U.S. PATENT DOCUMENTS

| | | |
|---|---|---|
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,278,302 A | 1/1994 | Caruthers et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Haberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,714,331 A | 2/1998 | Buchardt et al. |
| 5,719,046 A | 2/1998 | Guerineau et al. |
| 5,719,262 A | 2/1998 | Buchardt et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,898,031 A | 4/1999 | Crooke |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,107,094 A | 8/2000 | Crooke |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,232,536 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,303,374 B1 | 10/2001 | Zhang et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |

(56) References Cited

U.S. PATENT DOCUMENTS

| | | |
|---|---|---|
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,843,985 B2 | 1/2005 | Erickson, Jr. et al. |
| 6,992,237 B1 | 1/2006 | Habben et al. |
| 7,022,896 B1 | 4/2006 | Weeks et al. |
| 7,026,528 B2 | 4/2006 | Cheng et al. |
| 7,056,704 B2 | 6/2006 | Tuschl et al. |
| 7,078,196 B2 | 7/2006 | Tuschl et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,855,323 B2 | 12/2010 | Huang et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,097,712 B2 | 1/2012 | Paldi et al. |
| 8,143,480 B2 | 3/2012 | Axtell et al. |
| 8,158,414 B2 | 4/2012 | Rommens et al. |
| 8,507,457 B2 | 8/2013 | Paldi et al. |
| 8,548,778 B1 | 10/2013 | Hart et al. |
| 8,554,490 B2 | 10/2013 | Tang et al. |
| 8,598,332 B1 | 12/2013 | Waterhouse et al. |
| 9,006,414 B2 | 4/2015 | Huang et al. |
| 9,121,022 B2 | 9/2015 | Sammons et al. |
| 9,422,557 B2 | 8/2016 | Ader |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0086356 A1 | 7/2002 | Tuschl et al. |
| 2002/0114784 A1 | 8/2002 | Li et al. |
| 2002/0123476 A1 | 9/2002 | Emanuele et al. |
| 2003/0017068 A1 | 1/2003 | Larrain et al. |
| 2003/0044443 A1 | 3/2003 | Erickson, Jr. et al. |
| 2003/0092651 A1 | 5/2003 | Norris et al. |
| 2003/0096980 A1 | 5/2003 | Froehler et al. |
| 2003/0140371 A1 | 7/2003 | Stevens et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0180945 A1 | 9/2003 | Wang et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2004/0259247 A1 | 12/2004 | Tuschl et al. |
| 2005/0005319 A1 | 1/2005 | della-Cioppa et al. |
| 2005/0044591 A1 | 2/2005 | Yao et al. |
| 2005/0080032 A1 | 4/2005 | Gross et al. |
| 2005/0095199 A1 | 5/2005 | Whyard et al. |
| 2005/0215435 A1 | 9/2005 | Menges et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011448 A1 | 1/2007 | Chhabra et al. |
| 2007/0011775 A1 | 1/2007 | Allen et al. |
| 2007/0021360 A1 | 1/2007 | Nyce et al. |
| 2007/0026765 A1 | 2/2007 | Renn |
| 2007/0050860 A1 | 3/2007 | Andersen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0219151 A1 | 9/2007 | Satishchandran et al. |
| 2007/0232188 A1 | 10/2007 | Probasco |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0194512 A1 | 8/2008 | John et al. |
| 2008/0214443 A1 | 9/2008 | Baum et al. |
| 2008/0261303 A1 | 10/2008 | Kreutzer et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1* | 12/2009 | Baum .................. A01N 63/02 800/298 |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |

(56) References Cited

U.S. PATENT DOCUMENTS

| | | |
|---|---|---|
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0053231 A1 | 3/2012 | Paldi et al. |
| 2012/0107355 A1 | 5/2012 | Harris et al. |
| 2012/0108497 A1 | 5/2012 | Paldi et al. |
| 2012/0128218 A1 | 5/2012 | Amyot et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2012/0297501 A1* | 11/2012 | Beghyn .............. C12N 15/8218 800/265 |
| 2012/0316220 A1 | 12/2012 | Ward et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0058890 A1 | 3/2013 | Raemaekers et al. |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0232646 A1 | 9/2013 | Baum et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0289097 A1 | 10/2013 | Paldi et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2014/0371298 A1 | 12/2014 | Paldi et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |
| 2017/0037407 A1 | 2/2017 | Gleit-Kielmanowicz et al. |
| 2017/0088838 A1 | 3/2017 | Inberg et al. |
| 2017/0183683 A1 | 6/2017 | Zheng et al. |
| 2017/0260522 A1 | 9/2017 | Zheng et al. |

FOREIGN PATENT DOCUMENTS

| | | |
|---|---|---|
| CA | 2806295 A1 | 2/2011 |
| CN | 1505504 A | 6/2004 |
| CN | 101139607 A | 3/2008 |
| CN | 101279950 A | 10/2008 |
| CN | 101279951 A | 10/2008 |
| CN | 101914540 A | 12/2010 |
| CN | 102822350 A | 12/2012 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 375 408 A1 | 6/1990 |
| EP | 0 804 600 A1 | 11/1997 |
| EP | 1 157 991 A2 | 11/2001 |
| EP | 1 238 586 A1 | 9/2002 |
| EP | 1 416 049 A1 | 5/2004 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| EP | 2 703 489 A1 | 3/2014 |
| EP | 2 703 490 A1 | 3/2014 |
| EP | 2 706 114 A1 | 3/2014 |
| EP | 3 066 200 A1 | 9/2016 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009-508481 A | 3/2009 |
| JP | 2009067739 A | 4/2009 |
| JP | 2009114128 A | 5/2009 |
| JP | 2009126792 A | 6/2009 |

(56) References Cited

FOREIGN PATENT DOCUMENTS

| | | |
|---|---|---|
| JP | 2009137851 A | 6/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/47193 | 12/1997 |
| WO | WO 97/49816 A1 | 12/1997 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/04176 A1 | 1/2000 |
| WO | WO 00/32757 A2 | 6/2000 |
| WO | WO 00/034035 A2 | 6/2000 |
| WO | WO 00/044914 A1 | 8/2000 |
| WO | WO 01/07601 A2 | 2/2001 |
| WO | WO 01/34815 A1 | 5/2001 |
| WO | WO 2001/085970 A2 | 11/2001 |
| WO | WO 02/14472 A2 | 2/2002 |
| WO | WO 02/066660 A2 | 8/2002 |
| WO | WO 03/000679 A2 | 1/2003 |
| WO | WO 03/004649 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 2003/014357 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A2 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | 2005/110068 A2 | 11/2005 |
| WO | WO 2005/107437 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/074976 A1 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A2 | 3/2009 |
| WO | WO 2009/046384 A1 | 4/2009 |
| WO | WO 2009/060429 A2 | 5/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090402 A2 | 7/2009 |
| WO | WO 2009/091862 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |

(56) References Cited

FOREIGN PATENT DOCUMENTS

| | | |
|---|---|---|
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/128465 A1 | 11/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/021171 A1 | 2/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/164100 A2 | 12/2012 |
| WO | WO 2012/177639 A2 | 12/2012 |
| WO | WO 2013/010690 A1 | 1/2013 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/001336 A2 | 1/2015 |
| WO | WO 2015/010026 A2 | 1/2015 |
| WO | WO 2016/018887 A1 | 2/2016 |

OTHER PUBLICATIONS

Baum et al., "Control of coleopteran insect pests through RNA interference," *Nature Biotechnol.*, 25(11):1322-1326 (2007).
Becker et al., "Fertile transgenic wheat from microprojectile bombardment of scutellar tissue," *Plant J.*, 5(2), pp. 299-307 (1994).
Bytebier et al., "T-DNA organization in tumor cultures and transgenic plants of the monocotyledon *Asparagus officinalis*," *Proc. Natl. Acad. Sci. USA.*, 84:5345-5349 (1997).
CERA. (2012). GM Crop Database. Center for Environmental Risk Assessment (CERA), ILSI Research Foundation, Washington D.C., available electronically at www.cera-gmc.org/?action=gm_crop_database.
Chakravarty et al., "Genetic Transformation in Potato: Approaches and Strategies," *Amer. J. Potato Res.*, 84(4):301-311 (2007).
Cheng et al., "Production of fertile transgenic peanut (*Arachis hypogaea* L.) plants using Agrobacterium tumefaciens," *Plant Cell Rep.*, 15(9): 653-657 (1996).

Davidson and Ellington, "Engineering regulatory RNAs," *Trends Biotechnol.*, 23(3):109-112 (2005).
De Framond et al., "Mini-Ti: A New Vector Strategy for Plant Genetic Engineering," *Biotechnology*, 1:262-269 (1983).
Du et al., "A systematic analysis of the silencing effects of an active siRNA at all single-nucleotide mismatched target sites," *Nucleic Acids Res.*, 33(5):1671-1677 (2005).
Gallic et al., "Identification of the motifs within the tobacco mosaic virus 5'-leader responsible for enhancing translation," *Nucleic Acids Res.*, 20(17):4631-4638 (1992).
Gong et al., "Silencing of Rieske iron-sulfur protein using chemically synthesized siRNA as a potential biopesticide against *Plutella xylostella*," *Pest Manag. Sci.*, 67:514-520 (2011).
Hoekema et al., "A binary plant vector strategy based on separation of vir- and T-region of the *Agrobacterium tumefaciens* Ti-plasmid," *Nature*, 303:179-180 (1983).
International Search Report dated Oct. 1, 2015 in corresponding International Application No. PCT/US2015/022985.
Invitrogen's "Guide to Baculovirus Expression Vector Systems (BEVS) and Insect Cell Culture Techniques," (Life Technologies, Carlsbad, CA)(2002).
Isaacs et al., "Engineered riboregulators enable post-transcriptional control gene expression," *Nat. Biotechnol.*, 22(7):841-847 (Jul. 2004).
Kertbundit et al., "In vivo random β-glucuronidase gene fusions in *Arabidopsis thaliana*," *Proc. Natl. Acad. Sci. USA.*, 88:5212-5216 (1991).
Lee et al., "Aptamer database," *Nucleic Acids Res.*, 32(Database issue):D95-100 (2004).
Li et al., "Establishment of a highly efficient transformation system for pepper (*Capsicum annuum* L.)," *Plant Cell Reports*, 21:785-788 (2003).
Lu et al, "RNA silencing in plants by the expression of siRNA duplexes," *Nucleic Acids Research*, 32(21):e171 (2004).
Lu et al., "OligoWalk: an online siRNA design tool utilizing hybridization thermodynamics," *Nucleic Acids Res.*, 36(Web Server issue):W104-108 (2008).
Mandal et al., "Adenine riboswitches and gene activation by disruption of a transcription terminator," *Nature Struct. Mol. Biol.*, 11:29-35 (2004).
Mandal et al., "Gene regulation by riboswitches," *Nature Rev. Mol. Cell Biol.*, 5:451-463 (2004).
Mao et al., "Silencing a botton bollworm P450 monoosygenase gene by plant-mediated RNAi impairs larval tolerance of gossypol," *Nature Biotechnol.*, 25(11):1307-1313 (2007).
Masoud et al., "Constitutive expression of an inducible β-1,3-glucanase in alfalfa reduces disease severity caused by the oomycete pathogen *Phytophthora megasperma* f. sp*medicaginis*, but does not reduce disease severity of chitin-containing fungi," *Transgen. Res.*, 5:313-323 (1996).
Pitino et al., "Silencing of Aphid Genes by dsRNA Feeding from Plants," *PLoS One*,6(10):e25709 (2011).
Pridgeon et al., "Topically Applied AaelAP1 Double-Stranded RNA Kills Feman Adults of *Aedes aegypti*," *J. Med. Entomol.*, 45(3):414-420 (2008).
Reynolds et al., Rational siRNA design for RNA Interference,: *Nature Biotechnol.*, 22:326-330 (2004).
Sindhu et al., "Effective and specific in planta RNAi in cyst nematodes: expression interference of four parasitism genes reduces parasitic success," *J. Exp. Botany*, 60(1):315-324 (2009).
Steeves et al., "Transgenic soybeans expressing siRNAs specific to a major sperm protein gene suppress *Heterodera glycines* reproduction," *Funci. Plant Biol.*, 33(11):991-999 (2006).
Sun et al., "A highly efficient transformation protocol for Micro-Tom, a model cultivar for tomato functional genomics," *Plant Cell Physiol.*, 47(3):426-431 (2006).
Zhang et al., "Transgenic rice plants produced by electroporation-mediated plasmid uptake into photoplasts," *Plant Cell Rep.*, 7(6):379-384 (1988).
Advisory Action dated Feb. 22, 2013, in U.S. Appl. No. 13/332,430.
Agricultural Chemical Usage 2006 Vegetables Summary, Agricultural Statistics Board, NASS, USDA, pp. 1-372 (2007).
Agrios, Plant Pathology (Second Edition), 2:466-470 (1978).

(56) References Cited

OTHER PUBLICATIONS

Amarzguioui et al., "An algorithm for selection of functional siRNA sequences," Biochemical and Biophysical Research Communications, 316:1050-1058 (2004).
Amdam et al., Disruption of vitellogenin gene function in adult honeybees by intra-abdominal injection of double-stranded RNA, *BMC Biotechnology*, 3(1):1-8 (2003).
An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).
Andersen et al., "Delivery of siRNA from lyophilized polymeric surfaces," Biomaterials, 29:506-512 (2008).
Anonymous, "Agronomy Facts 37: Adjuvants for enhancing herbicide performance," n.p., 1-8, (Jan. 26, 2000), Web, (Jan. 21, 2014).
Aoki et al., "In Vivo Transfer Efficiency of Antisense Oligonucleotides into the Myocardium Using HVJ—Liposome Method," Biochem Biophys Res Commun, 231:540-545 (1997).
Arpaia et al., "Production of transgenic eggplant (*Solanum melongena* L.) resistant to Colorado Potato Beetle (*Leptinotarsa decemlineata* Say)," (1997) Theor. Appl. Genet., 95:329-334 (1997).
Artymovich, "Using RNA interference to increase crop yield and decrease pest damage," MMG 445 Basic Biotech., 5(1):7-12 (2009).
Ascencio-Ibanez et al., "DNA abrasion onto plants is an effective method for geminivirus infection and virus-induced gene silencing," Journal of Virological Methods, 142:198-203 (2007).
Axtell et al., "A Two-Hit Trigger for siRNA Biogenesis in Plants," Cell, 127:565-577 (2006).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Bart et al., "A novel system for gene silencing using siRNAs in rice leaf and stem-derived protoplasts," Plant Methods, 2(13):1-9 (2006).
Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Baum et al., "Control of coleopteran insect pests through RNA interference," *Nature Biotechnology*, 25(11):1322-1326 (2007).
Baum et al., "Progress Towards RNAi-Mediated Insect Pest Management" *Advances in Insect Physiology*, 47:249-295 (2014).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bhargava et al., "Long double-stranded RNA-mediated RNA interference as a tool to achieve site-specific silencing of hypothalamic neuropeptides," Brain Research Protocols, 13:115-125 (2004).
Bhatia et al., "Aphid resistance in *Brassica* crops: Challenges, biotechnological progress and emerging possibilities," *Biotechnology Advances* 29:879-955 (2011).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Breaker et al., "A DNA enzyme with Mg2+-dependent RNA phosphoesterase activity," Chemistry and Biology, 2:655-660 (1995).
Brodersen et al., "The diversity of RNA silencing pathways in plants," Trends in Genetics, 22(5):268-280 (2006).
Busch et al., "RNAi for discovery of novel crop protection products," Pflanzenschutz-Nachrichten Bayer, 58(1):34-50 (2005).
Campbell et al., "Gene-knockdown in the honey bee mite *Varroa destructor* by a non-invasive approach: studies on a glutathione S-transferase," Parasites & Vectors, 3(1):73, pp. 1-10 (2010).
Carthew, "Gene silencing by double-stranded RNA," *Curr Opin Cell Biol.*, 13(2):244-248 (2001).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chang et al., "Dual-target gene silencing by using long, sythetic siRNA duplexes without triggering antiviral responses," Molecules and Cells, 27(6)"689-695 (2009).
Chang et al., "Cellular Internalization of Fluorescent Proteins via Arginine-rich Intracellular Delivery Peptide in Plant Cells," Plant Cell Physiol., 46(3):482-488 (2005).
Chen et al., "Exploring MicroRNA-Like Small RNAs in the Filamentous Fungus *Fusarium oxysporum*," PLOS One, 9(8):e104956:1-10 (2014).
Christiaens et al., "The challenge of RNAi-mediated control of hemipterans," Current Opinion in Insect Science, 6:15-21 (2014).
CN101914540 Patent Diclosure, "Introduction of RNA into plant by interference," (2010).
Colorado Potato Beetle, *Leptinotarsa decemlineata*,Transcriptome, PLoS One, 9(1):e86012 (2014).
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Concise Descriptions of Relevance filed by a third party dated Nov. 29, 2012, in U.S. Appl. No. 13/042,856.
Constan et al., "An outer envelope membrane component of the plastid protein import apparatus plays an essential role in *Arabidopsis*," The Plant Journal, 38:93-106 (2004).
Cooney et al., "Site-Specific Oligonucleotide Binding Represses Transcription of the Human c-myc Gene in Vitro," Science ,241:456-459 (1988).
COST Action FA0806 progress report "Plant virus control employing RNA-based vaccines: A novel non-transgenic strategy" (2010).
Cox-Foster et al., "A Metagenomic Survey of Microbes in Honey Bee Colony Collapse Disorder," *Science*, 318(5848):283-287 (2007).
Dalakoums et al., "Induction of Silencing in Plants by High-Pressure Spraying of In vitro—Synthesized Small RNAs," Frontiers in Plant Science, 7(1327):1-5 (2016).
Dalmay et al., "An RNA-Depenedent RNA Polymerase Gene in *Arabidopsis* Is Required for Posttranscriptional Gene Silencing Mediated by a Transgene but Not by a Virus," Cell, 101:543-553 (2000).
Davidson et al., "Engineering regulatory RNAs," TRENDS in Biotechnology, 23(3):109-112 (2005).
Dawson et al., "cDNA cloning of the complete genome of tobacco mosaic virus and production of infectious transcripts," Proc. Natl. Acad. Sci. USA, 83:1832-1836 (1986).
De Framond, "MINI-Ti: A New Vector Strategy for Plant Genetic Engineering," Nature Biotechnology, 1:262-269 (1983).
Desai et al., "Reduction in deformed wing virus infection in larval and adult honey bees (*Apis mellifera* L.) by double-stranded RNA ingestion," Insect Molecular Biology, 21(4):446-455 (2012).
Di Prisco et al. "Varroa Destructor Is an Effective Vector of Israeli Acute Paralysis Virus in the Honeybee, *Apis mellifera*", Journal of General Virology, 92: 151-155 (2011).

(56) References Cited

OTHER PUBLICATIONS

Di Stilio et al., "Virus-Induced Gene Silencing as a Tool for Comparative Functional Studies in Thalictrum," PLoS One, 5(8):e12064 (2010).
Diallo et al., "Long Endogenous dsRNAs Can Induce Complete Gene Silencing in Mammalian Cells and Primary Cultures," Oligonucleotides, 13:381-392 (2003).
Dietemann et al, "Varroa destructor: research avenues towards sustainable control," Journal of Apicultural Research, 51(1):125-132 (2012).
Dietzl et al., "A genome-wide transgenic RNAi library for conditional gene inactivation in *Drosophila*," Nature, 448:151-157 (2007).
Du et al., "A systematic analysis of the silencing effects of an active siRNA at all single-nucleotide mismatched target sites," Nucleic Acids Research, 33(5):1671-1677 (2005).
Dunoyer et al., "Small RNA Duplexes Function as Mobile Silencing Signals Between Plant Cells," Science, 328:912-916 (2010).
Eamens et al., "RNA Silencing in Plants: Yesterday, Today, and Tomorrow," Plant Physiology, 147(2):456-468 (2008).
Ellington et al., "In vitro selection of RNA molecules that bind specific ligands," Nature, 346:818-822 (1990).
Eudes et al., "Cell-penetrating peptides," Plant Signaling & Behavior, 3(8):549-5550 (2008).
European Cooperation in the field of Scientific and Technical Research—Memorandum of Understanding for COST Action FA0806 (2008).
European Search Report and the European Search Opinion dated Feb. 3, 2014, in European Patent Application No. 13156180.5.
European Search Report dated Feb. 3, 2014, in European Patent Application No. 13156180.4.
European Search Report dated Feb. 6, 2014, in European Patent Application No. 13156183.9.
European Search Report dated Jun. 29, 2018, in European Patent Application No. 18157745.3.
European Search Report dated Sep. 7, 2017, in European Patent Application No. 17152830.0.
Examination Report dated Mar. 1, 2018, in Australian Patent Application No. 2013264742.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Feb. 6, 2014, in European Patent Application No. 13156183.9.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated May 23, 2018, in European Patent Application No. 15826865.6.
Extended European Search Report dated Nov. 7, 2017, in European Patent Application No. 15811092.4.
Extended European Search Report dated Nov. 8, 2017, in European Patent Application No. 15737282.2.
Extended European Search Report dated Oct. 8, 2013, in European Patent Application No. 11753916.3.
Extended European Search Report dated Sep. 29, 2016, in European Patent Application No. 14778840.0.
Extended European Search Report dated Apr. 13, 2018, in European Patent Application No. 15812530.0.
Extended European Search Report dated Mar. 15, 2018, in European Patent Application No. 17181861.0.
Fairbairn et al. "Host-Delivered RNAi: An Effective Strategy to Silence Genes in Plant Parasitic Nematodes", Planta, 226(6):1525-1533 (2007) Abstract.
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Fiala et al., "Reversible Downregulation of Protein Kinase A during Olfactory Learning Using Antisense Technique Impairs Long-Term Memory Formation in the Honeybee, *Apis mellifera*," J. Neuroscience, 19:10125-10134 (1999).
Final Office Action dated Apr. 7, 2016, in U.S. Appl. No. 13/619,980.
Final Office Action dated Aug. 1, 2013, in U.S. Appl. No. 13/318,636.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 18, 2011, in U.S. Appl. No. 12/222,949.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2015, in U.S. Appl. No. 13/612,985.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Nov. 7, 2013, in U.S. Appl. No. 13/042,856.
Final Office Action dated Oct. 15, 2012, in U.S. Appl. No. 13/332,430.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/603,347.
Final Office Action dated Sep. 9, 2016, in U.S. Appl. No. 14/608,951.
Fire et al., "Potent and specific genetic interference by double-stranded RNA in Caenorhabditis elegans," Nature, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Foley et al., "The distribution of *Aspergillus* spp. Opportunistic parasites in hives and their pathogenicity to honey bees," *Veterinary Microbiology*, 169:203-210 (2014).
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Friedberg, "Automated protein function prediction—the genomic challenge," Briefings in Bioinformatics, 7(3):225-242 (2006).
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).

(56) References Cited

OTHER PUBLICATIONS

Fukunaga et al., "dsRNA with 5' overhangs v contributes to endogenous and antiviral RNA silencing pathways in plants," The EMBO Journal, 28(5):545-555 (2009).
Further Examination Report dated May 16, 2014, in New Zealand Patent Application No. 601784.
Gallie et al., "Identification of the motifs within the tobacco mosaic virus 5'—leader responsible for enhancing translation," Nucleic Acids Res., 20(17):4631-4638 (1992).
Gan et al., "Bacterially expressed dsRNA protects maize against SCMV infection," Plant Cell Rep, 29(11):1261-1268 (2010).
Gao et al., "Down-regulation of acetolactate synthase compromises 01-1-mediated resistance to powdery mildew in tomato," BMC Plant Biology, 14 (2014).
Gao et al., "Nonviral Methods for siRNA Delivery," Molecular Pharmaceutics, 6(3):651-658 (2008).
Garbian et al., "Bidirectional Transfer of RNAi between Honey Bee and Varroa destructor: Varroa Gene Silencing Reduces Varroa Population," 8(12):1- 9:e1003035 (2012).
Gaskin et al., "Novel organosillicone adjuvants to reduce agrochemical spray volumes on row crops," New Zealand Plant Protection, 53:350-354 (2000).
Gill et al. "Stripped-Down DNA Repair in a High Reduced Parasite", BMC Molecular Biology, 8(24): 1-14 (2007).
Gomez-Zurita et al., "Recalibrated Tree of Leaf Beetles (*Chrysomelidae*) Indicates Independent Diversification of Angiosperms and Their Insect Herbivores," PLoS One, 4(e360):1-8 (2007).
Gong et al., "Silencing of Rieske iron—sulfur protein using chemically synthesised siRNA as a potential biopesticide against Plutella xylostella," Pest Manag Sci, 67:514-520 (2011).
Gossamer Threads, Compendium of Herbicide Adjuvants: Organo-Silicone Surfactant, p. 1-4 (1998).
Hagio, "Chapter 25: Direct Gene Transfer into Plant Mature Seeds via Electroporation After Vacuum Treatment," Electroporation and Sonoporation in Developmental Biology, p. 285-293 (2009).
Hamilton et al., "Two classes of short interfering RNA in RNA silencing," EMBO J., 21(17):4671-4679 (2002).
Han et al., "Molecular Basis for the Recognition of Primary microRNAs by the Drosha-DGCR8 Complex," Cell, 125(5):887-901 (2006).
Hannon, "RNA interference," Nature, 481:244-251 (2002).
Henderson et al., "U.S. National Bee Colony Loss Survey, www.beesurvey.com, Preliminary Findings With Respect to Colony Collapse Disorder (CCD)," Bee Alert Technology, Inc. (2007).
Heneberg et al., "Assemblage of filamentous fungi associated with aculeate hymenopteran brood in reed galls," *Journal of Invertebrate Pathology*, 133:95-106 (2016).
Herman et al., "A three-component dicamba O-demethylase from Pseudomonas maltophilia, strain DI-6: gene isolation, characterization, and heterologous expression," J. Biol. Chem., 280: 24759-24767 (2005).
Hess, "Surfactants and Additives," 1999 Proceedings of the California Weed Science Society, 51:156-172 (1999).
Hewezi et al., "Local infiltration of high- and low-molecular-weight RNA from silenced sunflower (*Helianthus annuus* L.) plants triggers post-transcriptional gene silencing in non-silenced plants," Plant Biotechnology Journal, 3:81-89 (2005).
Himber et al., "Transitivity-dependant and -independent cell-to-cell movement of RNA silencing," The EMBO Journal, 22(17):4523-4533 (2003).
Hsieh et al., "A library of siRNA duplexes targeting the phosphoinositide 3-kinase pathway: determinants of gene silencing for use in cell-based screens," Nucleic Acids Res., 32(3):893-901 (2004).
Hu et al., "High efficiency transport of quantum dots into plant roots with the aid of silwet L-77," Plant Physiology and Biochemistry, 48:703-709 (2010).
Huang et al., "Engineering broad root-know resistance in transgenic plants by RNAi silencing of a conserved and essential root-knot nematode parasitism gene," *Proc. Natl. Acad. Sci. USA*, 103(39):14302-14306 (2006).
Huesken et al., "Design of a genome-wide siRNA library using an artificial neural network," Nature Biotechnology, 23(8): 995-1001 (2005).
Hunter et al., "Large-Scale Field Application of RNAi Technology Reducing Israeli Acute Paralysis Virus Disease in Honey Bees (*Apis mellifera*, Hymenoptera: Apidae)," PLoS Pathogens, 6(12):e1001160-1-el 001160-10 (2010).
Hunter et al., "RNA Interference Strategy to suppress Psyllids & Leafhoppers," International Plant and Animal Genome XIX, 15-19 (2011).
Huvenne et al., "Mechanisms of dsRNA uptake in insects and potential of RNAi for pest control: A review," *Journal of Insect Physiology*, 56:227-235 (2010).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Apr. 26, 2012, in International Application No. PCT/IL2010/000844.
International Preliminary Report on Patentability dated Feb. 1, 2010, in International Application No. PCT/IL2008/001440.
International Preliminary Report on Patentability dated Feb. 21, 2012, in International Application No. PCT/IB2010/053776.
International Preliminary Report on Patentability dated Nov. 17, 2011, in International Application No. PCT/IB2010/051980.
International Preliminary Report on Patentability dated Oct. 23, 2014, in International Application No. PCT/IL2013/050321.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Dec. 31, 2015, in International Application No. PCT/US2015/042415.
International Search Report and Written Opinion dated Feb. 23, 2015, in International Application No. PCT/US2014/063832.
International Search Report and Written Opinion dated Feb. 24, 2011, in International Application No. PCT/IL2010/000844.
International Search Report and Written Opinion dated Jul. 19, 2010, in International Application No. PCT/IB2010/051980.
International Search Report and Written Opinion dated Jul. 8, 2015, in International Application No. PCT/US2015/011408.

(56) References Cited

OTHER PUBLICATIONS

International Search Report and Written Opinion dated Mar. 26, 2015, in International Application No. PCT/US2014/069535.
International Search Report and Written Opinion dated May 23, 2017, in International Application No. PCT/US2017/015061.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report and Written Opinion dated Nov. 30, 2010, in International Application No. PCT/IB2010/053776.
International Search Report and Written Opinion dated Oct. 1, 2015 in International Application No. PCT/US2015/022985.
International Search Report and Written Opinion dated Oct. 17, 2016, in International Application No. PCT/US2016/030579.
International Search Report and Written Opinion dated Oct. 28, 2013, in International Application No. PCT/IL2013/050321.
International Search Report dated Aug. 13, 2009, in International Application No. PCT/IL2008/001440.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," Nature Biotechnology, 22(7):841-847 (2004).
Jarvis et al, "An *Arabidopsis* mutant defective in the plastid general protein import apparatus," Science, 282:100-103 (1998).
Ji et al., "Regulation of small RNA stability: methylation and beyond," Cell Research, 22:624-636 (2012).
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Jones-Rhoades et al., "MicroRNAs and Their Regulatory Roles in Plants," Annu. Rev. Plant Biol., 57:19-53 (2006).
Kam et al., "Nanotube Molecular Transporters: Internalization of Carbon Nanotube—Protein Conjugates into Mammalian Cells," J. Am. Chem. Soc., 126(22):6850-6851 (2004).
Katoh et al., "Specific residues at every third position of siRNA shape its efficient RNAi activity," Nucleic Acids Res., 35(4): e27 (2007).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Khovorova et al., "Rational siRNA design for RNA interference," Nature Biotechnol., 22 :326-330 (2004).
Kikkert et al., "Stable Transformation of Plant Cells by Particle Bombardment/Biolistics," Methods in Molecular Biology, 286:61-78 (2005).
Kim et al., "Optimization of Conditions for Transient Agrobacterium-Mediated Gene Expression Assays in *Arabidopsis*," Plant Cell Reports, 28:1159-1167 (2009).
Kim et al., "Synthetic dsRNA Dicer substrates enhance RNAi potency and efficacy," Nature Biotechnology, 23(2):222-226 (2005).
Klahre et al., "High molecular weight RNAs and small interfering RNAs induce systemic posttranscriptional gene silencing in plants," Proc. Natl. Acad. Sci. USA, PNAS, 99(18):11981-11986 (2002).
Kondylis et al., "The Golgi apparatus: Lessons from *Drosophila*," FEBS Letters 583:3827-3838 (2009).
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Kumar et al., "Sequencing, De Novo Assembly and Annotation of the Colorado Potato Beetle, Leptinotarsa decemlineata, Transcriptome," PLOS One, 9(1):e86012:1-17 (2014).
Kusaba, "RNA interference in crop plants," Curr Opin Biotechnol, 15(2):139-143 (2004).
Lee et al., "A systematic RNAi screen identifies a critical role for mitochondria in C. elegans longevity." Nature Genetics, 33:40-48 (2003).
Lee et al., "Aptamer Database," Nucleic Acids Research, 32:D95-D100 (2004).
Li et al, "RNA interference in *Nilaparvata lugens* (Homoptera:Delphacidae) based on dsRNA ingestion," Pest Manag. Sci., 67:852-859 (2011).
Li et at., "Long dsRNA but not siRNA initiates RNAi in western corn rootworm larvae and adults," Journal of Applied Entomology, 139(6):432-445 (2015).
Liu et al., "Prevention of Chinese Sacbrood Virus Infection in Apis Ceram. Using RNA Interference," Current Microbiology, 61(5):422-428 (2010).
Liu et al., "Carbon Nanotubes as Molecular Transporters for Walled Plant Cells," Nano Letters, 9(3):1007-1010 (2009).
Liu et al., "Comparative study on the interaction of DNA with three different kinds of surfactants and the formation of multilayer films," Bioelectrochemistiy, 70:301-307 (2007).
Liu et al., "DNAzyme-mediated recovery of small recombinant RNAs from a 5S rRNA-derived chimera expressed in *Escherichia coli*," BMC Biotechnology, 10:85 (2010).
Liu et al., "RNA interference in Nilaparvata lugens (Homoptera : Delphacidae) based on dsRNA ingestion," Pest Manag. Sci., 67:852-859 (2011).
Liu, "Influence of Sugars on the Foliar Uptake of Bentazone and Glyphosate," New Zealand Plant Protection, 55:159-162 (2002).
Liu, "The Transformation of Nucleic Acid Degradants in Plants," China Organic Fertilizers, Agriculture Press, ISBN: 7-1091634 (with English translation).
Llave et al., "Endogenous and Silencing-Associated Small RNAs in Plants," The Plant Cell, 14:1605-1619 (2002).
Lu et al., "Oligo Walk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
Luque et al., "Water Permeability of Isolated Cuticular Membranes: A Structural Analysis," Archives of Biochemistry and Biophysics, 317(2):417-422 (1995).
Maas et al., "Mechanism and optimized conditions for PEG mediated DNA transfection into plant protoplasts," Plant Cell Reports, 8:148-149 (1989).
MacKenzie et al., "Transgenic Nicotiana debneyii expressing viral coat protein are resistant to potato virus S infection," Journal of General Virology, 71:2167-2170 (1990).
Maggi et al., "Resistance Phenomena to Amitraz From Population of the Ectoparasitic Mite Varroa Destructor of Argentina," Parasitology Research, 107(5):1189-1192 (2010).
Maher III et al., "Inhibition of DNA binding proteins by oligonucleotide-directed triple helix formation," Science, 245(4919):725-730 (1989).
Makkouk et al., "Virus Diseases of Peas, Beans, and Faba Bean in the Mediterranean region," Adv Virus Res, 84:367-402 (2012).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Mao et al., "Silencing a cotton bollworm P450 monooxygenase gene by plant-mediated RNAi impairs larval tolerance of gossypol.," Nat Biotechnol., 25(11):1307-13 (2007).
Maori et al., "Isolation and characterization of Israeli acute paralysis virus, a dicistrovirus affecting honeybees in Israel: evidence for

(56) References Cited

OTHER PUBLICATIONS diversity due to intra- and inter-species recombination," *Journal of General Virology*, 88:3428-3438 (2007).
Maori et al., "Israel Acute Paralysis Virus of Bees, Complete Genome," GenBank EMBL, EBI Dbfetch, XP002533679, Accession No. EF219380, Nov. 21, 2007.
Maori et al., "Reciprocal sequence exchange between non-retro viruses and hosts leading to the appearance of new host phenotypes," *Virology*, 362(2):342-349 (2007).
Maori et al., "IAPV, a bee-affecting virus associated with Colony Collapse Disorder can be silenced by dsRNA ingestion," Insect Molecular Biology, 18(1):55-60 (2009).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," Transge.
Matveeva et al., "Prediction of antisense oligonucleotide efficacy by in vitro methods," Nature Biotechnology, 16:1374-1375 (1998).
McGinnis, "RNAi for functional genomics in plants," Brief Funct Genomics, 9(2):111-7 (2010).
Meins et al., "RNA Silencing Systems and Their Relevance to Plant Development," Annu. Rev. Cell Dev. Biol., 21:297-318 (2005).
Melnyk et al., "Intercellular and systemic movement of RNA silencing signals," The EMBO Journal, 30:3553-3563 (2011).
Migge et al., "Greenhouse-grown conditionally lethal tobacco plants obtained by expression of plastidic glutamine synthetase antisense RNA may contribute to biological safety," Plant Science 153:107-112 (2000).
Molnar et al., "Plant Virus-Derived Small Interfering RNAs Originate redominantly from Highly Structured Single-Stranded Viral RNAs," Journal of Virology, 79(12):7812-7818 (2005).
Molnar et al., "Small Silencing RNAs in Plants Are Mobile and Direct Epigenetic Modification in Recipient Cells," Science, 328:872-875 (2010).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Moser et al., "Sequence—Specific Cleavage of Double Helical DNA by Triple Helix Formation," Science, 238:645-646 (1987).
Mount et al., "Gene and Metabolite Regulatory Network Analysis of Early Developing Fruit Tissues Highlights New Candidate Genes for the Control of Tomato Fruit Composition and Development," Plant Physiology, 149:1505- 1528 (2009).
Nakayashiki et al. "Evolution and Diversification of RNA Silencing Proteins in Fungi", Journal of Molecular Evolution, 63(1):127-135 (2006).
Non-Final Office Action dated Apr. 11, 2013, in U.S. Appl. No. 13/042,856.
Non-Final Office Action dated Apr. 15, 2014, in U.S. Appl. No. 13/446,557.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Feb. 5, 2014, in U.S. Appl. No. 13/446,557.
Non-Final Office Action dated Jan. 7, 2013, in U.S. Appl. No. 13/318,636.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 21, 2018, in U.S. Appl. No. 13/619,980.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated May 30, 2012, in U.S. Appl. No. 13/332,430.
Non-Final Office Action dated May 4, 2015, in U.S. Appl. No. 13/932,051.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 23, 2010, in U.S. Appl. No. 12/222,949.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Nord-Larsen et al., "Cloning, characterization and expression analysis of tonoplast intrinsic proteins and glutamine synthetase in ryegrass (*Lolium perenne* L.)," Plant Cell Reports, 28(10):1549-1562 (2009).
Nowak et al., "A new and efficient method for inhibition of RNA viruses by DNA interference," The FEBS Journal, 276:4372-4380 (2009).
Nunes et al., "A non-invasive method for silencing gene transcriptoin in honeybees maintained under natural conditions," *Insect Biochemistry and Molecular Biology*, 39:157-160 (2009).
Office Action dated 2015, in Chinese Patent Application No. 201080056585.9.
Office Action dated Apr. 13, 2016, in Chinese Patent Application No. 201280053985.3.
Office Action dated Apr. 15, 2014, in U.S. Appl. No. 13/446,557.
Office Action dated Aug. 1, 2013, in U.S. Appl. No. 13/318,636.

(56) References Cited

OTHER PUBLICATIONS

Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 25, 2015, in New Zealand Patent Application No. 700791.
Office Action dated Aug. 25, 2016, in Eurasian Patent Application No. 201201264.
Office Action dated Aug. 28, 2013, in Chinese Patent Application No. 201180012795.2.
Office Action dated Aug. 3, 2015, in Chinese Patent Application No. 201080056585.9 (English translation attached).
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03849.
Office Action dated Dec. 15, 2016, in Ukrainian Patent Application No. a 2014 03852.
Office Action dated Dec. 18, 2014, in Israeli Patent Application No. 216154 (with English translation).
Office Action dated Dec. 21, 2015, in Israeli Patent Application No. 240416 (with English translation).
Office Action dated Dec. 27, 2016, in Ukrainian Patent Application No. a 2012 11548.
Office Action dated Dec. 31, 2014, in Israeli Patent Application No. 205594 (with English translation).
Office Action dated Dec. 5, 2017, in Japanese Patent Application No. 2016-502033.
Office Action dated Feb. 17, 2011, in European Patent Application No. 08847971.2.
Office Action dated Feb. 17, 2014, in European Patent Application No. 08847971.2.
Office Action dated Feb. 17, 2014, in Mexican Patent Application No. MX/a/2012/010479.
Office Action dated Feb. 21, 2018, in Mexican Patent Application No. MX/a/2015/012632 (with English translation).
Office Action dated Feb. 24, 2014, in Eurasian Patent Application No. 201201264.
Office Action dated Feb. 5, 2015, in European Patent Application No. 13156183.9.
Office Action dated Feb. 6, 2015, in European Patent Application No. 10719620.6.
Office Action dated Jan. 19, 2014, in Israeli Patent Application No. 205594 (with English translation).
Office Action dated Jan. 26, 2015, in Israeli Patent Application No. 205594 (with English translation).
Office Action dated Jan. 26, 2015, in Israeli Patent Application No. 219193 (with English translation).
Office Action dated Jan. 30, 2015, in Mexican Patent Application No. Mx/a/2012/004378 (with English translation).
Office Action dated Jan. 7, 2013, in U.S. Appl. No. 13/318,636.
Office Action dated Jul. 11, 2017, in Mexican Patent Application No. MX/a/2015/013118 (with English translation).
Office Action dated Jul. 12, 2013, in European Patent Application No. 08847971.2.
Office Action dated Jul. 18, 2016, in Indonesian Patent Application No. W00201203610.
Office Action dated Jul. 2, 2013, in Chinese Patent Application No. 201080056585.9.
Office Action dated Jul. 23, 2015, in Ukrainian Patent Application No. 201211548.
Office Action dated Jul. 3, 2017, in Mexican Patent Application No. MX/a/2015/012632 (with English translation).
Office Action dated Jul. 6, 2017, in Mexican Patent Application No. MX/a/2015/013103 (with English translation).
Office Action dated Jun. 29, 2012, in European Patent Application No. 08847971.2.
Office Action dated Jun. 20, 2016, in Chinese Patent Application No. 201280054819.5.
Office Action dated Jun. 24, 2016, in Chinese Patent Application No. 201280053984.9.
Office Action dated Jun. 28, 2010, in U.S. Appl. No. 12/222,949.
Office Action dated Jun. 8, 2015, in European Patent Application No. 13156185.4.
Office Action dated Mar. 10, 2014, in European Patent Application No. 13156180.4.
Office Action dated Mar. 10, 2014, in European Patent Application No. 13156180.5.
Office Action dated Mar. 16, 2017, in Chinese Patent Application No. 201280054819.5.
Office Action dated Mar. 17, 2014, in European Patent Application No. 13156183.9.
Office Action dated Mar. 18, 2011, in U.S. Appl. No. 12/222,949.
Office Action dated Mar. 19, 2012, in Israeli Patent Application No. 205594 (English Translation attached).
Office Action dated Mar. 19, 2015, in Canadian Patent Application No. 2,704,858.
Office Action dated Mar. 20, 2015, in Indian Patent Application No. 1150/MUMNP/2010.
Office Action dated Mar. 8, 2018 (with English translation), in Chilean Patent Application No. 201403192.
Office Action dated May 12, 2014, in Chinese Patent Application No. 201080056585.9.
Office Action dated May 12, 2014, in Mexican Patent Application No. MX/a/2012/004378 (English Translation attached).
Office Action dated May 29, 2015, in European Patent Application No. 13156180.4.
Office Action dated May 29, 2015, in European Patent Application No. 13156180.5.
Office Action dated May 3, 2016, in Chilean Patent Application No. 201601057.
Office Action dated May 30, 2012, in U.S. Appl. No. 13/332,430.
Office Action dated Nov. 10, 2014, in European Patent Application No. 10779855.5.
Office Action dated Nov. 15, 2016, in Mexican Patent Application No. MX/a/2014/003068 (with English translation).
Office Action dated Nov. 21, 2012, in U.S. Appl. No. 13/318,636.
Office Action dated Nov. 6, 2014, in Australian Patent Application No. 2010244122.
Office Action dated Oct. 15, 2012, in U.S. Appl. No. 13/332,430.
Office Action dated Oct. 21, 2015, in European Patent Application No. 13723252.6.
Office Action dated Oct. 23, 2013, in Australian Patent Application No. 2008325989.
Office Action dated Oct. 31, 2013, , in Mexican Patent Application No. MX/a/2012/004378 (English Translation attached).
Office Action dated Oct. 31, 2013, in Mexican Patent Application No. MX/a/2012/004378.
Office Action dated Oct. 8, 2013, in European Patent Application No. 10719620.6.
Office Action dated Sep. 29, 2014, European Patent Application No. 13156180.4.
Office Action dated Sep. 29, 2014, in European Patent Application No. 13156180.5.
Office Action dated Sep. 1, 2015, in European Patent Application No. 10779855.5.
Office Action dated Sep. 23, 2010, in U.S. Appl. No. 12/222,949.
Office Action dated Sep. 28, 2015, in U.S. Appl. No. 13/932,051.
Office Action dated Sep. 29, 2014, in European Patent Application No. 13156180.4.

(56) References Cited

OTHER PUBLICATIONS

Office Action dated Sep. 4, 2015, in European Patent Application No. 13156183.9.
Office Action dated Sep. 5, 2016, in Ukrainian Patent Application No. a 2014 03846.
Office Action dated Sep. 6, 2017, in Chinese Patent Application No. 2014800154012 (with English translation).
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," Science Asia, 33:35-39 (2007).
Orbović et al., "Foliar-Applied Surfactants and Urea Temporarily Reduce Carbon Assimilation of Grapefruit Leaves," J. Amer. Soc. Hort. Sci., 126(4):486-490 (2001).
Ouellet et al., "Members of the Acetohydroxyacid Synthase Muligene Family of *Brassica napus* Have Divergent Patterns of Expression," The Plant Journal, Blackwell Scientific Publications, Oxford, GB, 2(3):321-330 (1992).
Paddison et al., "Stable suppression of gene expression by RNAi in mammalian cells," Proc. Natl Acad. Sci. USA, 99(3):1443-1448 (2002).
Palacios et al., "Genetic Analysis of Israel Acute Paralysis Virus: Distinct Clusters Are Circulating in the United States," *Journal of Virology*, 82(13):6209-6217 (2008).
Palauqui et al., "Activation of systemic acquired silencing by localised introduction of DNA," Current Biology, 9:59-66 (1999).
Paldi et al. "Effective Gene Silencing in a Microsporidian Parasite Associated With Honeybee (*Apis mellifera*) Colony Declines", Applied and Environmental Microbiology, 760(17):5960-5964 (2010).
Parera et al., "Dehydration Rate after Solid Matrix Priming Alters Seed Performance of Shrunken-2 Corn," J. Amer. Soc. Hort. Sci., 119(3):629-635 (1994).
Partial European Search Report dated Dec. 6, 2017, in European Patent Application No. 17181861.0.
Partial International Search Report dated Jul. 24, 2013, International Application No. PCT/2013/050321.
Partial International Search Report dated May 13, 2009, in International Application No. PCT/IL2008/001440.
Partial Supplementary European Search Report dated Mar. 2, 2015, in European Patent Application No. 12 831 494.5.
Partial Supplementary European Search Report dated Jan. 11, 2018, in European Patent Application No. 15812530.0.
Patent Examination Report dated Nov. 6, 2014, in Australian Patent Application No. 2010244122.
Patent Examination Report dated Oct. 23, 2013, in Australian Patent Application No. 2008325989.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Jun. 8, 2017, in Australian Patent Application No. 2012308686.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," Plant Physiology, 153:799-805 (2010).
Paungfoo-Lonhienne et al., "DNA uptake by *Arabidopsis* induces changes in the expression of CLE peptides which control root morphology," Plant Signaling & Behavior, 5(9):1112-1114 (2010).

Pei et al., "On the art of identifying effective and specific siRNAs," Nature Methods, 3(9):670-676 (2006).
Peretz et al., "A Universal Expression/Silencing Vector in Plants," Plant Physiology, 145:1251-1263 (2007).
Pitino et al., "Silencing of Aphid Genes by dsRNA Feeding from Plants," *PLos One*, 6:e25709 (2011).
Pornprom et al., "Glutamine synthetase mutation conferring target-site-based resistance to glufosinate in soybean cell selections," Pest Manag Sci, 2009; 65(2):216-222 (2009).
Powles et al., "Evolution in Action: Plants Resistant to Herbicides," Annual Review of Plant Biology, 61(1):317-347 (2010).
Pratt et al., "Amaranthus rudis and A. tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Price et al. "RNAi-Mediated Crop Protection Against Insects", Trends in Biotechnology, XP022757296, 26(7):393-400 (2008).
Pridgeon et al., "Topically Applied AaeIAP1 Double-Stranded RNA Kills Feman Adults of *Aedes aegypti*," J. Med. Entomol., 45(3):414-420 (2008).
Rajur et al., "Covalent Protein—Oligonucleotide Conjugates for Efficient Delivery of Antisense Molecules," Bioconjug Chem., 8:935-940 (1997).
Rakoczy-Trojanowska, "Alternative Methods of Plant Transformation—a short review," Cellular & Molecular Biology Letters, 7:849-858 (2002).
Reddy et al., "Aminomethylphosphonic Acid Accumulation in Plant Species Treated with Glyphosate," J. Agric. Food Chem., 56(6):2125-2130 (2008).
Reither et al., "Specificity of DNA triple helix formation analyzed by a FRET assay," BMC Biochemistry, 3:27 (2002).
Requisition by the Examiner and Examination Search Report dated Mar. 19, 2015, in Canadian Patent Application No. 2,704,858.
Rey et al., "Diversity of Dicotyledenous-Infecting Geminiviruses and Their Associated DNA Molecules in Southern Africa, Including the South-West Indian Ocean Islands," Viruses, 4:1753-1791 (2012).
Reynolds et al., "Rational siRNA design for RNA interference," Nature Biotechnology, 22:326-330 (2004).
Richardson et al., "Targeting and assembly of components of the TOC protein import complex at the chloroplast outer envelope membrane," Frontiers in Plant Science, 5:1-14 (2014).
Riggins et al., "Characterization of de novo transcriptome for waterhemp (*Amaranthus tuberculatus*) using GS-FLX 454 pyrosequencing and its application for studies of herbicide target-site genes," Pest Manag. Sci., 66:1042-1052 (2010).
Robalino et al., "Double-Stranded RNA and Antiviral Immunity in Marine Shrimp: Inducible Host Mechanisms and Evidence for the Evolution of Viral Counter-Responses," Developmental & Comparative Immunology, 31: 539-547 (2007).
Roberts, "Fast-track applications: The potential for direct delivery of proteins and nucleic acids to plant cells for the discovery of gene function," Plant Methods, 1(12):1-3 (2005).
Rose et al., "Functional polarity is introduced by Dicer processing of short substrate RNAs," Nucleic Acids Research, 33(13):4140-4156 (2005).
Rothnie et al., Pararetroviruses and Retroviruses: A Comparative Review of Viral Structure and Gene Expression Strategies, Advances in Virus Research, 44:1-67 (1994).
Ryabov et al., "Cell-to-Cell, but Not Long-Distance, Spread of RNA Silencing That Is Induced in Individual Epidermal Cells," Journal of Virology, 78(6):3149-3154 (2004).
Salanenka et al., "Seedcoat Permeability: Uptake and Post-germination Transport of Applied Model Tracer Compounds," HortScience, 46(4):622-626 (2011).
Santoro et al., "A general purpose RNA-cleaving DNA enzyme," *Proc. Natl. Acad. Sci. USA*, 94:4262-4266 (1997).
Santosh et al., "RNA interference for the control of whiteflies (*Bemisia tabaci*) by oral route," Journal of Biosciences, 36(1):153-161 (2011).

(56) References Cited

OTHER PUBLICATIONS

Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," PNAS, 107(34):14945-14946 (2010).
Schweizer et al., "Double-stranded RNA interferes with gene function at the single-cell level in cereals," The Plant Journal, 24(6):895-903 (2000).
Scott et al., "Towards the elements of successful insect RNAi," Journal of Insect Physiology, 59(12):1212-1221 (2013).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).
Search Report dated Jul. 24, 2017, in Chinese Patent Application No. 201480014392.5 (with English translation).
Search Report dated Oct. 20, 2017, in Chinese Patent Application No. 201380039346.6.
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Second Office Action dated May 12, 2014, in Chinese Patent Application No. 201080056585.9.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A systematic study to determine the extent of gene silencing in Nicotiana benthamiana and other Solanaceae species when heterologous gene sequences are used for virus-induced gene silencing," New Phytologist, 176:782-791 (2007).
Sharma et al., "A simple and efficient Agrobacterium-mediated procedure for transformation of tomato," J. Biosci., 34(3):423 433 (2009).
Shen et al., "The Role of Varroa Mites in Infections and Deformed Wing Virus (DWV) in Honey," Available Online Aug. 18, 2005.
Shintani et al., "Antisense Expression and Overexpression of Biotin Carboxylase in Tobacco Leaves," Plant Physiol., 114:881-886 (1997).
Showalter, "Structure and Function of Plant Cell Wall Proteins," The Plant Cell, 5:9-23 (1993).
Sijen et al., "On the Role of RNA Amplification in dsRNA-Triggered Gene Silencing," Cell, 107:465-476 (2001).
Silwet L-77 Spray Adjuvant for agricultural applications, product description from Momentive Performance Materials, Inc. (2003).
Sindhu et al., "Effective and specific in planta RNAi in cyst nematodes: expression interference of four parasitism genes reduces parasitic success," *J. Exp. Botany*, 60:315-324 (2008).
Siomi et al. "On the Road to Reading the RNA-Interference Code", Nature, 457(7228): 396-404, Jan. 22, 2009. Abstract.
Slamovits et al. "Genome Compaction and Stability in Microsporidian Intracellular Parasites", Current Biology, 14(10): 891-896, May 25, 2004.
Small, "RNAi for revealing and engineering plant gene functions," Current Opinion in Biotechnology, 18:148-153 (2007).
Snead et al., "Molecular basis for improved gene silencing by Dicer substrate interfering RNA compared with other siRNA variants," Nucleic Acids Research, 41(12):6209-6221 (2013).
Soares et al., "Capillary feeding of specific dsRNA induces silencing of the isac gene in nymphal Ixodes scapularis ticks," Insect Mol. Biol., 14(4):443-452 (2005).

Song et al., "Herbicide," New Heterocyclic Pesticide, Chemical Industry Press, 354-356 (2011).
Standifer et al., "Supplemental Feeding of Honey Bee Colonies," *Agriculture Information Bullentin* No. 413, USDA, pp. 1-8 (1977).
Statement of Grounds and Particulars dated Sep. 1, 2017, in Australian Patent No. 2014262189.
Steeves et al., "Transgenic soybeans expressing siRNAs specific to a major sperm protein gene suppress Heterodera glycines reproduction," Funct. Plant Biol., 33:991-999 (2006).
Stevens et al., "New Formulation Technology—SILWET® Organosilicone Surfactants Have Physical and Physiological Properties Which Enhance the Performance of Sprays," Proceedings of the 9th Australian Weeds Conference, pp. 327-331 (1990).
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," Journal of Pesticide Science, 38:103-122 (1993).
Stock et al., "Possible Mechanisms for Surfactant-Induced Foliar Uptake of Agrochemicals," Pestic. Sci., 38:165-177 (1993).
Strat et al., "Specific and nontoxic silencing in mammalian cells with expressed long dsRNAs," Nucleic Acids Research, 34(13):3803-3810 (2006).
Street "Why is DNA (and not RNA) a stable storage form for genetic information?," Biochemistry Revisited, pp. 1-4 (2008).
Sudarsan et al., "Metabolite-binding RNA domains are present in the genes of eukaryotes," RNA, 9:644-647 (2003).
Summons to Attend Oral Proceedings Pursuant to Rule 115(1) EPC, dated Aug. 7, 2017, in European Patent Application No. 12832160.1.
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Supplementary European Search Report dated Jan. 17, 2018, in European Patent Application No. 15773480.7.
Supplementary Partial European Search Report dated Jan. 11, 2018 in European Appln. 15 82 6865.
Supplementary Partial European Search Report dated Oct. 16, 2017, in European Patent Application No. 15773480.7.
Takasaki et al., "An Effective Method for Selecting siRNA Target Sequences in Mammalian Cells," Cell Cycle, 3:790-795 (2004).
Tang et al., "Efficient delivery of small interfering RNA to plant cells by a nanosecond pulsed laser-induced stress wave for post-transcriptional gene silencing," Plant Science, 171:375-381 (2006).
Tank Mixing Chemicals Applied to Peanut Crops: Are the Chemicals Compatible?, College of Agriculture & Life Sciences, NC State University, AGW-653, pp. 1-11 (2004).
Templeton et al., "Improved DNA: liposome complexes for increased systemic delivery and gene expression," Nature Biotechnology, 15:647-652 (1997).
Tenllado et al., "Crude extracts of bacterially expressed dsRNA can be used to protect plants against virus infection," BMC Biotechnology, 3(3):1-11 (2003).
Tenllado et al., "Double-Stranded RNA-Mediated Interference with Plant Virus Infection," Journal of Virology, 75(24):12288-12297 (2001).
Tenllado et al., "RNA interference as a new biotechnological tool for the control of virus diseases in plants," Virus Research, 102:85-96 (2004).
Tepfer, "Risk assessment of virus resistant transgenic plants," Annual Review of Phytopathology, 40:467-491 (2002).
Terenius et al., RNA interference in Lepidoptera: an overview of successful and unsuccessful studies and implications for experimental design, Journal of Insect Physiology, 57(2):231-245 (2011).
Third Office Action dated Nov. 25, 2014, in Chinese Patent Application No. 201080056585.9.
Third Party Submission filed on Nov. 29, 2012 in U.S. Appl. No. 13/042,856.
Thomas et al., "Size constraints for targeting post-transcriptional gene silencing and for RNA-directed methylation in Nicotiana benthamiana using a potato virus X vector," The Plant Journal, 25(4):417-425 (2001).

(56) References Cited

OTHER PUBLICATIONS

Tian et al., "Developmental Control of a Lepidopteran Pest *Spodoptera exigua* by Ingestion of Bacteria Expressing dsRNA of a Non-Midgut Gene," PLoS ONE, 4:e6225, pp. 1-14 (2009).
Timmons et al., "Specific interference by ingested dsRNA," Nature, 395:854 (1998).
Tomari et al., "Perspective: machines for RNAi," Genes & Dev., 19:517-529 (2005).
Töpfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts," Bio/Technology, 6:1072-1074 (1988).
Tran et al., "Control of specific gene expression in mammalian cells by co-expression of long complementary RNAs," FEBS Lett.;573(1-3):127-134 (2004).
Tranel et al., "Resistance of weeds to ALS-inhibiting herbicides: what have we learned?," Weed Science, 50:700-712 (2002).
Translation dated Jan. 15, 2015 of Office Action dated Dec. 18, 2014 From the Israel Patent Office Re. Application No. 216154.
Translation dated Jan. 20, 2015 of Office Action dated Dec. 31, 2014 From the Israel Patent Office Re. Application No. 205594.
Translation of Office Action dated Jul. 2, 2013 From the State Intellectual Property Office of the People's Republic of China Re. Application No. 201080056585.9.
Tsugawa et al., "Efficient transformation of rice protoplasts mediated by a synthetic polycationic amino polymer," Theor Appl Genet, 97:1019-1026 (1998).
Turina et al., "Tospoviruses in the Mediterranean Area," Advances in Virus Research, 84:403-437 (2012).
Turner et al., "RNA interference in the light brown apple moth, *Epiphyas postvittana* (Walker) induced by double-stranded RNA feeding," Insect Mol. Biol., 15(3):383-391 (2006).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Ui-Tei et al., "Guidelines for the selection of highly effective siRNA sequences for mammalian and chick RNA interference," Nucleic Acids Res., 32(3): 936-948 (2004).
Ullu et al., "RNA Interference in Protozoan Parasites," *Cellular Microbiology*, 6(6):509-519 (2004).
Ulrich et al., "Large scale RNAi screen in Tribolium reveals novel target genes for pest control and the proteasome as prime target," BMC genomics, 16(1):671 (2015).
Unnamalai et al., "Cationic oligopeptide-mediated delivery of dsRNA for post-transcriptional gene silencing in plant cells," FEBS Letters, 566:307-310 (2004).
Unniraman et al., "Alternate Paradigm for Intrinsic Transcription Termination in Eubacteria," The Journal of Biological Chemistry, 276(45)(9):41850-41855 (2001).
Unniraman et al., "Conserved Economics of Transcription Termination in Eubacteria," Nucleic Acids Research, 30(3):675-684 (2002).
Upadhyay et al., RNA interference for the control of whiteflies (*Bemisia tabaci*) by oral route, J. Biosci., 36(1):153-161 (2011).
Urayama et al., "Knock-down of OsDCL2 in Rice Negatively Affects Maintenance of the Endogenous dsRNA Virus, Oryza sativa Endornavirus," Plant and Cell Physiology, 51(1):58-67 (2010).
van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vaucheret, "Post-transcriptional small RNA pathways in plants: mechanisms and regulations," Genes Dev., 20:759-771 (2006).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).

Vermeulen et al., "The contributions of dsRNA structure to Dicer specificity and efficiency," RNA, 11(5):674-682 (2005).
Vert et al., "An accurate and interpretable model for siRNA efficacy prediction," BMC Bioinformatics, 7:520 (2006).
Voinnet et al., "Systemic Spread of Sequence-Specific Transgene RNA Degradation in Plants Is Initiated by Localized Introduction of Ectopic Promoterless DNA," Cell, 95:177-187 (1998).
Voinnet, "Origin, Biogenesis, and Activity of Plant MicroRNAs," Cell, 136:669-687 (2009).
Wakelin et al., "A target-site mutation is present in a glyphosate-resistant Lolium rigidum population," Weed Res. (Oxford), 46(5):432-440 (2006).
Walton et al., "Thermodynamic and Kinetic Characterization of Antisense Oligodeoxynucleotide Binding to a Structured mRNA," *Biophysical Journal*, 82:366-377 (2002).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).
Wang et al. "Molecular Characterization of an Arachnid Sodium Channel Gene From the Varroa Mite (Varroa Destructor)", Insect Biochemistry and Molecular Biology, XP002621492, 33(7): 733-739, Jul. 2003. Abstract.
Wang et al. "Tracking Anonymous Peer-to-Peer VoIP Calls on the Internet", ACM, CCS'05, Alexandria, VA, USA, Nov. 7-11, 2005, 11 P., 2005.
Wang et al., "Foliar uptake of pesticides-Present status and future challenge," ScienceDirect, 87:1-8 (2007).
Wang et al., "Principle and technology of genetic engineering in plants," in Plant genetic engineering principles and techniques, Beijing: Science Press, pp. 313-315 (1998).
Wang et al. ,"Silkworm Coatomers and Their Role in Tube Expansion of Posterior Silkgland," PLoS ONE 5(10): E133252 (2010).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," Plant Physiol, 57:855-861 (1976).
Waterhouse et al., "Virus resistance and gene silencing in plants can be induced by simultaneous expression of sense and antisense RNA," Proc Natl Acad Sci USA, 95 13959-13964 (1998).
Welch et al., "Expression of ribozymes in gene transfer systems to modulate target RNA levels," Curr Opin Biotechnol. 9(5):486-496 (1998).
Whyard et al., "Ingested double-stranded RNAs can act as species-specific insecticides," Insect Biochem. Mol. Biol., 39(11):824-832 (2009).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot Noxious Weed Control Board (NWCB) of Washington State (2010) <www.nwcb.wa.govidetail.asp?weed=46>.
Williams "Unique Physiology of Host-Parasite Interactions in Microsporidia Infections," Cellular Microbiology, 11(11):1551-1560 (2009).
Williams et al., "Genome Sequence Surveys of Brachiola Algerae and Edhazardia Aedis Reveal Micriosporidia With Low Gene Densities," BMC Genomics, 9(200):1-9 (2008).
Wilson, et al., "Transcription termination at intrinsic terminators: The role of the RNA hairpin," Proc. Natl. Acad. Sci. USA, 92:8793-8797 (1995).
Winkler et al., "Thiamine derivatives bind messenger RNAs directly to regulate bacterial gene expression," Nature, 419:952-956 (2002).
Written Opinion dated Apr. 7, 2016, in Singapore Patent Application No. 201206152-9.
Written Opinion dated Aug. 13, 2009, in International Application No. PCT/IL2008/001440.
Written Opinion dated Mar. 6, 2017, in Singaporean Patent Application No. 2012061529.

(56) References Cited

OTHER PUBLICATIONS

Written Opinion dated May 8, 2014, in International Application No. PCT/IL2013/050447.
Written Opinion dated Sep. 1, 2014, in Singapore Patent Application No. 201206152-9.
Yadav et al., "Host-Generated Double Stranded RNA Induces RNAi in Plant-Parasitic Nematodes and Protects the Host From Infection," *Molecular & Biochemical Parasitology*, 148:219-222 (2006).
Yao et al., "Development of RNAi Methods for Peregrinus maidis, the Corn Planthopper," PLOS One, 8(8):1-11 (2013).
Yin et al., "Production of double-stranded RNA for interference with TMV infection utilizing a bacterial prokaryotic expression system," Appl. Microbiol. Biotechnol., 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zhang et al., "Agrobacterium-mediated transformation of *Arabidopsis thaliana* using the floral dip method," Nature Protocols, 1(2):1-6 (2006).
Zhang et al., "Cationic lipids and polymers mediated vectors for delivery of siRNA," Journal of Controlled Release, 123:1-10 (2007).
Zhang et al., "Transgenic rice plants produced by electroporation-mediated plasmid uptake into protoplasts," The Plant Cell Rep., 7:379-384 (1988).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhao et al., "Phyllotreta striolata (Coleoptera: Chiysomelidae) Arginine kinase cloning and RNAi-based pest control," European Journal of Entomology, 105(5):815-822 (2008).
Zhao et al., "PsOrl, a potential target for RNA interference-based pest management," *Insect Molecular Biology* 20(1):97-104 (2011).
Zhu et al., "Ingested RNA interference for managing the populations of the Colorado potato beetle, *Leptinotarsa decemlineata*," Pest Manag Sci, 67:175-182 (2010).
Zotti et al., "RNAi technology for insect management and protection of beneficial insects from diseases: lessons, challenges and risk assessments," Neotropical Entomology, 44(3):197-213 (2015).
Bachman et al., "Characterization of the spectrum of insecticidal activity of a double-stranded RNA with targeted activity against Western Corn Rootworm (*Diabrotica virgifera virgifera* LeConte)," *Transgenic Res.*, 22(6):1207-22 (2013).
Chu et al., "Potent RNAi by short RNA triggers," RNA, 14:1714-1719 (2008).
Extended European Search Report dated Nov. 15, 2018, in European Patent Application No. 1818863 3.4.
Hawkins et al., "Promoter targeted small RNAs induce long-term transcriptional gene silencing in human cells," Nucleic Acids Research, 37(9):2984-2995 (2009).
Qiang et al., "Cloning and bioinformatics analysis of an ubiquitin gene of the rice stem borer, Chilo suppressalis Walker (Lepidoptera: Pyralidae)," African Journal of Biotechnology, 10(60):12852-12858 (2011).
Akiyoshi et al., "Genomic Survey of the Non-Cultivatable Opportunistic Human Pathogen, Enterocytozoon bieneusi," PLoS Pathog, 5(I):e1000261:1-14 (2009).
Alarcon-Reverte et al., "Resistance to ACCase-Inhibiting Herbicides in the Weed Lolium Multiflorum," Comm. Appl. Biol. Sci, 73(4):899:902 (2008).
Al-Kaff et al., "Plants rendered herbicide-susceptible by cauliflower mosaic virus-elicited suppression of a 35S promoter-regulated transgene," Nature Biotechnology, 18:995-999 (2000).
Ambrus et al., "The diverse roles of RNA helicases in RNAi," Cell Cycle, 8(21):3500-3505 (2009).
Amdam et al., "The hive bee to forager transition in honeybee colonies: the double repressor hypothesis," Journal of Theoretical Biology, 223:451-464 (2003).

Amdam et al., "Altered Physiology in Worker Honey Bees (Hymenoptera: Apidae) Infested with the Mite Varroa destructor (Acari: Varroidae): A Factor in Colony Loss During Overwintering?" J. Econ. Entomol., 97(3):741-747 (2004).
Andersson et al., "A novel selection system for potato transformation using a mutated AHAS gene," Plant Cell Rep, 22:261-267 (2003).
Araujo et al., "RNA interference of the salivary gland nitrophorin 2 in the triatomine bug Rhodnius prolixus (Hemiptera: Reduviidae) by dsRNA ingestion or injection," Insect Biochemistry and Molecular Biology, 36:683-693 (2006).
Aronstein et al., "SID-I is implicated in systemic gene silencing in the honey bee," Journal of Apicultural Research and Bee World, 45(I):20-24 (2006)
Aronstein et al., "Characterization of a honey bee Toll related receptor gene Aml8w and its potential involvement in antimicrobial immune defense," Apidologie, 36:3-14 (2005).
Database Accession No. BT006855, "Homo sapiens calmodulin 3 (phosphorylase kinase, delta) mRNA" pp. 1-2 (2003).
Database Accession No. EF219380, "SV 1; linear; mRNA; STD; VRL; 9499 BP.," pp. 1-5 (2007).
Extended European Search Report dated Jan. 14, 2019, in European Patent Application No. 16789940.0.
Extended European Search Report dated Mar. 4, 2019, in European Patent Application No. 18 20 7017.7.
Final Office Action dated Sep. 28, 2015, in U.S. Appl. No. 13/932,051.
GenBank Bankit, <https://www.ncbi.nlm.nih.gov/WebSub/?tool=genbank[Sep. 27, 2016 6:27:51 AM]> pp. 1-3 (2016).
Heath et al., "RNA Interference Technology to Control Pest Sea Lampreys—A Proof-of-Concept," PLOS One, 9(2):e88387:1-9 (2014).
International Search Report and Written Opinion dated Aug. 13, 2009, in International Application No. PCT/IL2008/001440.
International Search Report and Written Opinion dated Mar. 26, 2015, in International Application No. PCT/US2014/069353.
Invitation to Pay Additional Fees dated Jul. 24, 2013, in International Application No. PCT/IL/2013/050321.
Invitation to Pay Additional Fees dated May 13, 2009, in International Application No. PCT/IL2008/001440
Non-Final Office Action dated Jun. 28, 2010, in U.S. Appl. No. 12/222,949.
Non-Final Office Action dated Nov. 21, 2012, in U.S. Appl. No. 13/318,636.
Patel et al., "The Making of a Queen: TOR Pathway Is a Key Player in Diphenic Caste Development," Plos One, 2(6):e509:1-7 (2007).
Patent Examination Report No. 1 dated Nov. 6, 2014, in Australian Patent Application No. 2010244122.
Patent Examination Report No. 1 dated Oct. 23, 2013, in Australian Patent Application No. 2008325989.
Pridgeon et al., "Topically Applied AaelAPl Double-Stranded RNA Kills Female Adults of Aedes aegypti" J. Med. Entomol., 45(3):414-420 (2008).
Reddy et al."Organosilicone Adjuvants Increased the Efficacy of Glyphosate for Control of Weeds in Citrus (Citrus spp.)" HortScience 27(9): 1003-1005 (1992).
Second Office Action dated May 12, 2014, in Chinese Patent Application No. 201080056585.9, with English translation of same.
Shen et al., "The role of varroa mites in infections of Kashmir bee virus (KBV) and deformed wing virus (DWV) in honey bees," Virology, 342(1): 141-149 (2005).
Siomi et al., "On the Road to Reading the RNA-Interference Code", Nature, 457(7228): 396-404 (2009).
Slamovits et al., "Genome Compaction and Stability in Microsporidian SiIntracellular Parasites", Current Biology, 14(10): 891-896 (2004).
Supplementary Partial European Search Report date Jan. 11, 2018 in European Appln. 15826865.
Third Office Action dated November 25, 2014, in Chinese Patent Application No. 201080056585.9, with English translation of same.
Wang et al., "Tracking Anonymous Peer-to-Peer VoIP Calls on the Internet," ACM, CCS'05, Alexandria, VA, USA, pp. 1-11 (2005).
Wang et al., "Molecular Characterization of An Arachnid Sodium Channel Gene From the Varroa Mite (Varroa Destructor)", Insect Biochemistry and Molecular Biology, 33(7): 733-739 (2003).

(56) References Cited

OTHER PUBLICATIONS

Yibrah et al., "Antisense RNA inhibition of uidA gene expression in transgenic plants: Evidence for interaction between first and second transformation events," Hereditas, 118:273-280 (1993).

Zrachya et al., "Production of siRNA targeted against TYLCV coat protein transcripts leads to silencing of its expression and resistance to the virus," Transgenic Res., 16:385-398 (2007).

\* cited by examiner

COMPOSITIONS AND METHODS FOR CONTROLLING INSECT PESTS

CROSS-REFERENCE TO RELATED APPLICATIONS AND INCORPORATION OF SEQUENCE LISTINGS

This application is a U.S. National Entry of International Application No. PCT/US2015/022985, filed on Mar. 27, 2015 which claims priority to U.S. Provisional Patent Application No. 61/973,484 filed Apr. 1, 2014, which is incorporated by reference in its entirety herein. A sequence listing contained in the file named "P34352US01_SEQ.txt" which is 71,047 bytes in size (measured in MS-Windows®) and created on Sep. 29, 2016 is filed electronically herewith and incorporated by reference in its entirety.

FIELD OF THE INVENTION

Disclosed herein are methods for controlling invertebrate pest infestations, particularly in plants, and compositions and polynucleotides useful in such methods. More specifically, this invention is related to polynucleotides and methods of use thereof for modifying the expression of genes in an invertebrate pest, particularly through RNA interference. Pest species of interest include insects that infest crop plants, e. g., *Plutella xylostella* (diamondback moth), *Spodoptera frugiperda* (fall armyworm), *Lygus hesperus* (western tarnished plant bug), and *Euschistus heros* (neotropical brown stink bug).

BACKGROUND OF THE INVENTION

Commercial crops are often the targets of attack by invertebrate pests such as insects. Compositions for controlling insect infestations in plants have typically been in the form of chemical insecticides. However, there are several disadvantages to using chemical insecticides. For example, chemical insecticides are generally not selective, and applications of chemical insecticides intended to control insect pests in crop plants can exert their effects on non-target insects and other invertebrates as well. Chemical insecticides often persist in the environment and can be slow to degrade, thus potentially accumulating in the food chain. Furthermore the use of persistent chemical insecticides can result in the development of resistance in the target insect species. Thus there has been a long felt need for more environmentally friendly methods for controlling or eradicating insect infestation on or in plants, i. e., methods which are species-selective, environmentally inert, non-persistent, and biodegradable, and that fit well into pest resistance management schemes.

Insecticidal compositions that include *Bacillus thuringiensis* ("Bt") bacteria have been commercially available and used as environmentally safe and acceptable insecticides for more than thirty years. The effectiveness of these compositions is due to insecticidal proteins that are produced exclusively by Bt bacteria. The insecticidal Bt proteins do not persist in the environment, are highly selective as to the target species affected, exert their effects only upon ingestion by a target insect, and have been shown to be harmless to plants and other non-targeted organisms, including humans and other vertebrates. Transgenic plants containing one or more recombinant genes encoding insecticidal Bt proteins are also available in the art and are resistant to insect pest infestation. One positive environmental result of the use of transgenic plants expressing Bt proteins is a decrease in the amount of chemical insecticides that are applied to control pest infestation in such transgenic crop fields, resulting in decreased contamination of soil and waters by non-degraded or excess chemical insecticides. In addition, there has been a noticeable increase in the numbers of beneficial insects in fields in which Bt protein-expressing transgenic crop plants are grown because of the decrease in the use of non-selective chemical insecticides.

RNA interference (RNAi, RNA-mediated gene suppression) is another approach used for pest control. In invertebrates RNAi-based gene suppression was first demonstrated in nematodes (Fire et al., (1998) *Nature*, 391:806-811; Timmons & Fire (1998) *Nature*, 395:854). Subsequently, RNAi-based suppression of invertebrate genes using recombinant nucleic acid techniques has been reported in a number of species, including agriculturally or economically important pests from various insect and nematode taxa, such as: root-knot nematodes (*Meloidogyne* spp.), see Huang et al. (2006) *Proc. Natl. Acad. Sci. USA*, 103:14302-14306, doi: 10.1073/pnas.0604698103); cotton bollworm (*Helicoverpa armigera*), see Mao et al. (2007) *Nature Biotechnol.*, 25:1307-1313, doi:10.1038/nbt1352; Western corn rootworm (*Diabrotica virgifera* LeConte), see Baum et al. (2007) *Nature Biotechnol.*, 25:1322-1326, doi:10.1038/nbt1359; sugar beet cyst nematode (*Heterodera schachtii*), see Sindhu et al. (2008) *J. Exp. Botany*, 60:315-324, doi: 10.1093/jxb/ern289; mosquito (*Aedes aegypti*), see Pridgeon et al. (2008) *J. Med. Entomol.*, 45:414-420, doi: full/ 10.1603/0022- 2585%282008%2945%5B414%3ATAADRK %5D2.0.CO %3B2 fruit flies (*Drosophila melanogaster*), flour beetles (*Tribolium castaneum*), pea aphids (*Acyrthosiphon pisum*), and tobacco hornworms (*Manduca sexta*), see Whyard et al. (2009) *Insect Biochem. Mol. Biol.*, 39:824-832, doi:10.1016/ j.ibmb.2009.09.00; diamondback moth (*Plutella xylostella*), see Gong et al. (2011) *Pest Manag. Sci.*, 67: 514-520, doi:10.1002/ps.2086; green peach aphid (*Myzus persicae*), see Pitino et al. (2011) *PLoS ONE*, 6:e25709, doi: 10.1371/ journal.pone.0025709; brown planthopper (*Nilaparvata lugens*), see Li et al. (2011) *Pest Manag. Sci.*, 67:852-859, doi:10.1002/ps.2124; and whitefly (*Bemisia tabaci*), see Upadhyay et al. (2011) *J. Biosci.*, 36:153-161, doi:10.1007/ s12038-011-9009-1.

This invention is related to methods of controlling insect pests, in particular insects which infest crop plants and have previously been found to be recalcitrant to RNA-mediated gene suppression methods, e. g., *Plutella xylostella* (diamondback moth), *Spodoptera frugiperda* (fall armyworm), *Lygus hesperus* (western tarnished plant bug), and *Euschistus heros* (neotropical brown stink bug). Double-stranded RNA (dsRNA) trigger sequences have been identified for testing on the recalcitrant insect species *Plutella xylostella* (diamondback moth, DBM), *Spodoptera frugiperda* (fall armyworm, FAW), *Lygus hesperus* (western tarnished plant bug, WTPB), and *Euschistus heros* (neotropical brown stink bug, NBSB). These triggers are designed to suppress novel target genes that are putative orthologues of genes previously demonstrated to be efficacious targets for RNAi-mediated mortality in Western corn rootworm (*Diabrotica virgifera*).

This invention is further related to polynucleotides and recombinant DNA molecules and constructs useful in methods of controlling insect pests. This invention is further related to insecticidal compositions, as well as to transgenic plants resistant to infestation by insect pests. This invention is also related to methods of identifying efficacious double-stranded RNA triggers for controlling insect pests, and methods for identifying target genes that are likely to represent essential functions, making these genes preferred targets for RNAi-mediated silencing and control of insect pests.

SUMMARY OF THE INVENTION

This invention is related to control of insect species, especially those that are economically or agriculturally important pests. The compositions and methods of this invention include recombinant polynucleotide molecules, such as recombinant DNA constructs for making transgenic plants resistant to infestation by insect species and RNA "triggers" that are useful, e. g., as topically applied agents for causing RNAi-mediated suppression of a target gene in a insect species and thus controlling or preventing infestation by that insect species. Another utility of this invention is a polynucleotide-containing composition (e. g., a composition containing a dsRNA trigger for suppressing a target gene) that is topically applied to an insect species or to a plant, plant part, or seed to be protected from infestation by an insect species. This invention is further related to methods for selecting preferred insect target genes that are more likely to be effective targets for RNAi-mediated control of an insect species.

In one aspect, this invention provides a method for controlling an insect infestation of a plant including contacting with a dsRNA an insect that infests a plant, wherein the dsRNA includes at least one segment of 18 or more contiguous nucleotides with a sequence of about 95% to about 100% complementarity with a fragment of a target gene of the insect, and wherein the target gene has a DNA sequence selected from the group consisting of SEQ ID NOs:1-12 and 43-44. In embodiments, the dsRNA includes an RNA strand with a sequence of about 95% to about 100% identity or complementarity with a sequence selected from the group consisting of SEQ ID NOs:13-26, 28-29, 30-42, 45, and 46. In embodiments, the dsRNA includes an RNA strand with a sequence selected from the group consisting of SEQ ID NOs:13-26, 28-29, 30-42, 45, and 46. In embodiments, the dsRNA trigger suppresses a gene in the insect and stunts or kills the insect.

In another aspect, this invention provides a method of causing mortality or stunting in an insect, including providing in the diet of an insect at least one recombinant RNA including at least one silencing element essentially identical or essentially complementary to a fragment of a target gene sequence of the insect, wherein the target gene sequence is selected from the group consisting of SEQ ID NOs:1-12 and 43-44, and wherein ingestion of the recombinant RNA by the insect results in mortality or stunting in the insect. In embodiments, the silencing element includes an RNA strand with a sequence of about 95% to about 100% identity or complementarity with a sequence selected from the group consisting of SEQ ID NOs:13-26, 28-29, 30-42, 45, and 46. In embodiments, the silencing element includes an RNA strand with a sequence selected from the group consisting of SEQ ID NOs:13-26, 28-29, 30-42, 45, and 46.

In another aspect, this invention provides an insecticidal composition including an insecticidally effective amount of a recombinant RNA molecule, wherein the recombinant RNA molecule includes at least one segment of 18 or more contiguous nucleotides with a sequence of about 95% to about 100% complementarity with a fragment of a target gene of an insect that infests a plant, and wherein the target gene has a DNA sequence selected from the group consisting of SEQ ID NOs:1-12 and 43-44. In embodiments, the recombinant RNA molecule is dsRNA. In embodiments, the recombinant RNA molecule includes at least one segment (e. g., an RNA strand or segment of an RNA strand) with a sequence of about 95% to about 100% identity or complementarity with a sequence selected from the group consisting of SEQ ID NOs:13-26, 28-29, 30-42, 45, and 46. In embodiments, the recombinant RNA molecule includes at least one segment (e. g., an RNA strand or segment of an RNA strand) with a sequence selected from the group consisting of SEQ ID NOs:13-26, 28-29, 30-42, 45, and 46.

In another aspect, this invention provides a method of providing a plant having improved resistance to an insect, including expressing in the plant a recombinant DNA construct including DNA encoding at least one silencing element essentially identical or essentially complementary to a fragment of a target gene sequence of the insect, wherein the target gene sequence is selected from the group consisting of SEQ ID NOs:1-12 and 43-44, and wherein ingestion of the recombinant RNA by the insect results in mortality or stunting in the insect. In embodiments, the silencing element is ssRNA. In other embodiments, the silencing element is dsRNA. In embodiments, the silencing element includes RNA (e. g., an RNA strand or segment of an RNA strand) with a sequence of about 95% to about 100% identity or complementarity with a sequence selected from the group consisting of SEQ ID NOs:13-26, 28-29, 30-42, 45, and 46. In embodiments, the silencing element includes RNA (e. g., an RNA strand or segment of an RNA strand) with a sequence selected from the group consisting of SEQ ID NOs:13-26, 28-29, 30-42, 45, and 46.

In another aspect, this invention provides a recombinant DNA construct including a heterologous promoter, such as a heterologous promoter functional in a bacterial cell or in a eukaryotic cell (e. g., a plant cell or an insect cell), operably linked to DNA encoding an RNA transcript including a sequence of about 95% to about 100% identity or complementarity with a sequence selected from the group consisting of SEQ ID NOs:13-26, 28-29, 30-42, 45, and 46. In embodiments, the RNA transcript is ssRNA. In other embodiments, the RNA transcript is dsRNA. In embodiments, the silencing element includes RNA (e. g., an RNA strand or segment of an RNA strand) with a sequence of about 95% to about 100% identity or complementarity with a sequence selected from the group consisting of SEQ ID NOs:13-26, 28-29, 30-42, 45, and 46. In embodiments, the silencing element includes RNA (e. g., an RNA strand or segment of an RNA strand) with a sequence selected from the group consisting of SEQ ID NOs:13-26, 28-29, 30-42, 45, and 46.

In related aspects, this invention provides man-made compositions including the polynucleotide or trigger of this invention, such as dsRNA formulations useful for topical application to a plant or substance in need of protection from an insect infestation, recombinant constructs and vectors useful for making transgenic plant cells and transgenic plants, formulations and coatings useful for treating plants (including plant seeds or propagatable parts such as tubers), plant seeds or propagatable parts such as tubers treated with or containing a polynucleotide of this invention as well as commodity products and foodstuffs produced from such plants, seeds, or propagatable parts (especially commodity products and foodstuffs having a detectable amount of a polynucleotide of this invention). A further aspect of this invention are polyclonal or monoclonal antibodies that bind a peptide or protein encoded by a sequence or a fragment of a sequence selected from the group consisting of SEQ ID NOs:1-12 and 43-44; another aspect of this invention are polyclonal or monoclonal antibodies that bind a peptide or protein encoded by a sequence or a fragment of a sequence selected from the group consisting of SEQ ID NOs:13-26, 28-29, 30-42, 45, and 46 or the complement thereof. Such antibodies are made by routine methods as known to one of ordinary skill in the art.

Other aspects and specific embodiments of this invention are disclosed in the following detailed description and working Examples.

DETAILED DESCRIPTION OF THE INVENTION

Figure 1:
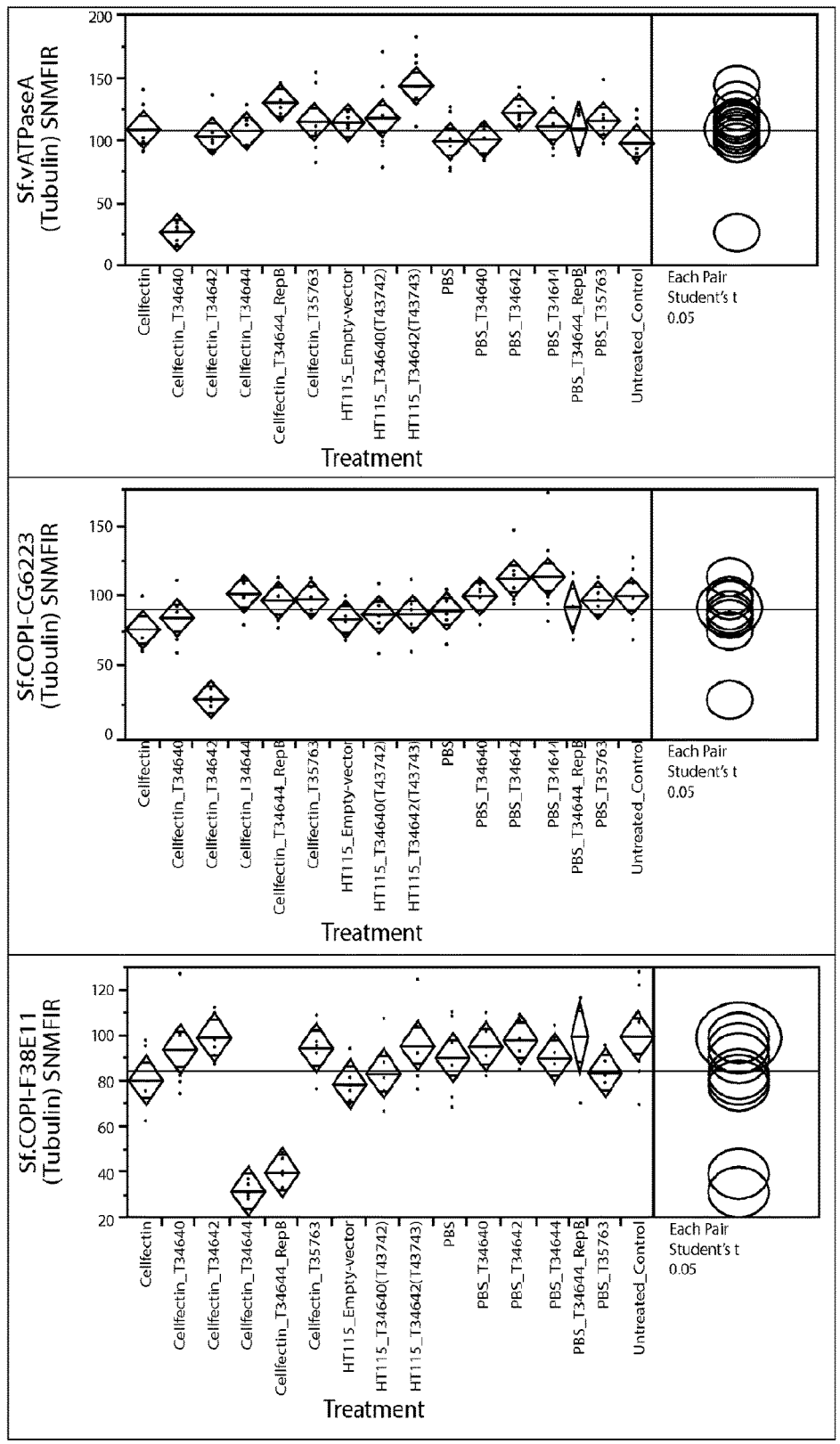
FIG. 1 depicts the results of the transfection experiments described in Example 2 for the dsRNA triggers (TOP PANEL) T34640 (SEQ ID NO:17, targetting V-ATPase A subunit), (MIDDLE PANEL) T34642 (SEQ ID NO:18, targetting COPI coatomer beta subunit), or (BOTTOM PANEL) T34644 (SEQ ID NO:19, targetting COPI coatomer beta prime subunit) in *Spodoptera frugiperda* (fall armyworm, FAW) SF9 cells.

Unless defined otherwise, all technical and scientific terms used have the same meaning as commonly understood by one of ordinary skill in the art to which this invention belongs. Generally, the nomenclature used and the manufacturing or laboratory procedures described below are well known and commonly employed in the art. Conventional methods are used for these procedures, such as those provided in the art and various general references. Where a term is provided in the singular, the inventors also contemplate aspects of the invention described by the plural of that term. Where there are discrepancies in terms and definitions used in references that are incorporated by reference, the terms used in this application shall have the definitions given. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6$^{th}$ edition, 2002, McGraw-Hill, New York), or the "Oxford Dictionary of Biology" (6$^{th}$ edition, 2008, Oxford University Press, Oxford and New York). The inventors do not intend to be limited to a mechanism or mode of action. Reference thereto is provided for illustrative purposes only.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotides of the DNA with uracil (U) nucleotides. Thus, providing a specific DNA sequence is understood to define the exact RNA equivalent. A given first polynucleotide sequence, whether DNA or RNA, further defines the sequence of its exact complement (which can be DNA or RNA), i. e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

The term "polynucleotide" commonly refers to a DNA or RNA molecule containing multiple nucleotides and generally refers both to "oligonucleotides" (a polynucleotide molecule of 18-25 nucleotides in length) and longer polynucleotides of 26 or more nucleotides. Polynucleotides also include molecules containing multiple nucleotides including non-canonical nucleotides or chemically modified nucleotides as commonly practiced in the art; see, e. g., chemical modifications disclosed in the technical manual "RNA Interference (RNAi) and DsiRNAs", 2011 (Integrated DNA Technologies Coralville, Iowa). Generally, polynucleotides or triggers of this invention, whether DNA or RNA or both, and whether single- or double-stranded, include at least one segment of 18 or more contiguous nucleotides (or, in the case of double-stranded polynucleotides, at least 18 contiguous base-pairs) that are essentially identical or complementary to a fragment of equivalent size of the DNA of a target gene or the target gene's RNA transcript. Throughout this disclosure, "at least 18 contiguous" means "from about 18 to about 10,000, including every whole number point in between". Thus, embodiments of this invention include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, such as the dsRNA triggers described in the working Examples, its length can be similarly described in terms of base pairs. Double-stranded polynucleotides, such as the dsRNA triggers described in the working examples, can further be described in terms of one or more of the single-stranded components.

The polynucleotides or triggers of this invention are generally designed to suppress or silence one or more genes ("target genes"). The term "gene" refers to any portion of a nucleic acid that provides for expression of a transcript or encodes a transcript. A "gene" can include, but is not limited to, a promoter region, 5' untranslated regions, transcript encoding regions that can include intronic regions, 3' untranslated regions, or combinations of these regions. In embodiments, the target genes can include coding or non-coding sequence or both. In other embodiments, the target gene has a sequence identical to or complementary to a messenger RNA, e. g., in embodiments the target gene is a cDNA.

Controlling Insect Infestations of a Plant by Contacting with a dsRNA

A first aspect of this invention provides a method for controlling an insect infestation of a plant including contacting with a double-stranded RNA (dsRNA) an insect that infests a plant, wherein the dsRNA includes at least one segment of 18 or more contiguous nucleotides with a sequence of about 95% to about 100% (e. g., about 95%, about 96%, about 97%, about 98%, about 99%, or about 100%) complementarity with a fragment of a target gene of the insect, and wherein the target gene has a DNA sequence selected from the group consisting of SEQ ID NOs:1-12 and 43-44. In this context "controlling" includes inducement of a physiological or behavioural change in an insect (adult or larvae or nymphs) such as, but not limited to, growth stunting, increased mortality, decrease in reproductive capacity, decrease in or cessation of feeding behavior or movement, or decrease in or cessation of metamorphosis stage development. "Double-stranded" refers to the base-pairing that occurs between sufficiently complementary, anti-parallel nucleic acid strands to form a double-stranded nucleic acid structure, generally under physiologically relevant conditions.

In various embodiments, the insect is selected from the group consisting of *Spodoptera* spp., *Lygus* spp., *Euschistus* spp., and *Plutella* spp. Insects of particular interest include *Spodoptera frugiperda* (fall armyworm), *Lygus hesperus* (western tarnished plant bug), *Euschistus heros* (neotropical brown stink bug), and *Plutella xylostella* (diamondback moth).

Various embodiments of the method include those wherein the insect is *Spodoptera frugiperda* (fall armyworm) and the target gene includes a DNA sequence selected from the group consisting of SEQ ID NOs:1-3; wherein the insect is *Lygus hesperus* (western tarnished plant bug) and the target gene includes a DNA sequence selected from the group consisting of SEQ ID NOs:4-7, 43, and 44; wherein the insect is *Euschistus heros* (neotropical brown stink bug) and the target gene includes a DNA sequence selected from the group consisting of SEQ ID NOs:8-9; and wherein the insect is *Plutella xylostella* (diamondback moth) and the target gene includes a DNA sequence selected from the group consisting of SEQ ID NOs:10-12. Other embodiments of the method include those wherein the insect is *Spodoptera frugiperda* (fall armyworm) and the dsRNA includes a sequence selected from the group consisting of SEQ ID NOs:17-19; wherein the insect is *Lygus hesperus* (western tarnished plant bug) and the dsRNA includes a sequence selected from the group consisting of SEQ ID NOs:14-16, 22, 26, 45, and 46; wherein the insect is *Euschistus heros* (neotropical brown stink bug) and the dsRNA includes a sequence selected from the group consisting of SEQ ID NOs:23-25; and wherein the insect is *Plutella xylostella* (diamondback moth) and the dsRNA includes a sequence selected from the group consisting of SEQ ID NOs:13, 20-21, and 28-29. Other embodiments include those where the dsRNA has a sequence modified as described in Example 5 to eliminate matches to non-target organisms, such as the modified sequences (SEQ ID NOs: 30-42) disclosed in Table 6.

The plant can be any plant that is subject to infestation by an insect that can be controlled by the polynucleotides disclosed herein. Plants of particular interest include commercially important plants, including row crop plants, vegetables, and fruits, and other plants of agricultural or decorative use. Examples of suitable plants are provided under the heading "Plants".

In embodiments of the method, the dsRNA includes multiple segments each of 18 or more contiguous nucleotides with a sequence of about 95% to about 100% (e. g., about 95%, about 96%, about 97%, about 98%, about 99%, or about 100%) complementarity with a fragment of a target gene of the insect. For example, the dsRNA can include segments corresponding to different regions of the target gene, or can include multiple copies of a segment. In other embodiments of the method, the dsRNA includes multiple segments, each of 18 or more contiguous nucleotides with a sequence of about 95% to about 100% (e. g., about 95%, about 96%, about 97%, about 98%, about 99%, or about 100%) complementarity with a fragment of a different target gene; in this way multiple target genes, or multiple insect species, can be suppressed.

In embodiments of the method, the dsRNA is blunt-ended. In other embodiments, the dsRNA has an overhang at one or both ends (termini); the overhang can be a single nucleotide or 2, 3, 4, 5, 6, or more nucleotides, and can be located on the 5' end or on the 3' end of a strand. The dsRNA can be chemically synthesized, or can be produced by expression in a microorganism, by expression in a plant cell, or by microbial fermentation. The dsRNA can be chemically modified, e. g., to improve stability or efficacy.

In some embodiments of the method, the contacting includes application of a composition including the dsRNA to a surface of the insect or to a surface of the plant infested by the insect. The composition can include or be in the form of a solid, liquid, powder, suspension, emulsion, spray, encapsulation, microbeads, carrier particulates, film, matrix, or seed treatment. In embodiments, the composition can be applied to a seed, e. g., by soaking the seed in a liquid composition including the dsRNA, wherein the seed imbibes or takes up the dsRNA into the seed interior or seed endosperm in an effective amount to provide improved resistance to the insect pest by the seed or a plant or seedling grown from the seed. In embodiments, the contacting includes providing the dsRNA in a composition that further includes one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator. In embodiments, the contacting includes providing the dsRNA in a composition that further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

In some embodiments of the method, the contacting includes providing the dsRNA in a composition that is ingested by the insect, such as in a liquid, emulsion, or powder applied to a plant on which the insect feeds, or in the form of bait. Such compositions can further includes one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator. Such compositions can further include at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the combination of the dsRNA and the pesticidal agent provides a level of insect control that is synergistic, i. e., greater than the sum of the effects of the dsRNA and the pesticidal agent components if tested separately.

Methods of Causing Mortality or Stunting in an Insect

Another aspect of this invention provides a method of causing mortality or stunting in an insect, including providing in the diet of an insect at least one recombinant RNA including at least one silencing element essentially identical or essentially complementary to a fragment of a target gene sequence of the insect, wherein the target gene sequence is selected from the group consisting of SEQ ID NOs:1-12 and 43-44, and wherein ingestion of the recombinant RNA by the insect results in mortality or stunting in the insect. The method is applicable to insects at various life stages. In embodiments, the method causes mortality or stunting in an insect larva or nymph. In other embodiments, the method causes mortality in adult insects.

In embodiments of the method the recombinant RNA includes at least one RNA strand having a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 30-42, 45, and 46. Embodiments of the method include those wherein the insect is *Spodoptera frugiperda* (fall armyworm) and the target gene includes a DNA sequence selected from the group consisting of SEQ ID NOs:1-3; wherein the insect is *Lygus hesperus* (western tarnished plant bug) and the target gene includes a DNA sequence selected from the group consisting of SEQ ID NOs:4-7, 43, and 44; wherein the insect is *Euschistus heros* (neotropical brown stink bug) and the target gene includes a DNA sequence selected from the group consisting of SEQ ID NOs:8-9; and wherein the insect is *Plutella xylostella* (diamondback moth) and the target gene includes a DNA sequence selected from the group consisting of SEQ ID NOs:10-12. Other embodiments of the method include those wherein the insect is *Spodoptera frugiperda* (fall armyworm) and the silencing element includes a sequence selected from the group consisting of SEQ ID NOs:17-19; wherein the insect is *Lygus hesperus* (western tarnished plant bug) and the silencing element includes a sequence selected from the group consisting of SEQ ID NOs:14-16, 22, 26, 45, and 46; wherein the insect is *Euschistus heros* (neotropical brown stink bug) and the silencing element includes a sequence selected from the group consisting of SEQ ID NOs:23-25; and wherein the insect is *Plutella xylostella* (diamondback moth) and the silencing element includes a sequence selected from the group consisting of SEQ ID NOs:13, 20-21, and 28-29. Other embodiments include those where the recombinant RNA has a sequence modified as described in Example 5 to eliminate matches to non-target organisms, such as the modified sequences (SEQ ID NOs:30-42) disclosed in Table 6.

In embodiments of the method, the recombinant RNA is dsRNA. In these embodiments, the dsRNA can be blunt-ended dsRNA, or can be dsRNA with an overhang at one or both ends (termini); the overhang can be a single nucleotide or 2, 3, 4, 5, 6, or more nucleotides, and can be located on the 5' end or on the 3' end of a strand. The dsRNA can be chemically synthesized, or can be produced by expression in a microorganism, by expression in a plant cell, or by microbial fermentation. The dsRNA can be chemically modified, e. g., to improve stability or efficacy. In embodiments of the method where the recombinant RNA is dsRNA, the dsRNA includes at least one RNA strand having a sequence of about 95% to about 100% identity or complementarity with a sequence selected from the group consisting of SEQ ID NOs:13-26, 28-29, 30-42, 45, and 46.

In some embodiments of the method, the recombinant RNA is provided in the insect's diet in the form of an ingestible composition, such as in a liquid, emulsion, or powder applied to a plant on which the insect feeds, or in the form of bait. Such ingestible compositions can further includes one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator. Such ingestible compositions can further include at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the combination of the recombinant RNA and the pesticidal agent provides a level of insect stunting or mortality that is synergistic, i. e., greater than the sum of the effects of the recombinant RNA and the pesticidal agent components if tested separately.

Insecticidal Compositions

Another aspect of the invention provides an insecticidal composition including an insecticidally effective amount of a recombinant RNA molecule, wherein the recombinant RNA molecule includes at least one segment of 18 or more contiguous nucleotides with a sequence of about 95% to about 100% (e. g., about 95%, about 96%, about 97%, about 98%, about 99%, or about 100%) complementarity with a fragment of a target gene of an insect that infests a plant, and wherein the target gene has a DNA sequence selected from the group consisting of SEQ ID NOs:1-12 and 43-44. By "insecticidally effective" is meant effective in inducing a physiological or behavioural change in an insect (adult or larvae or nymphs) that infests a plant such as, but not limited to, growth stunting, increased mortality, decrease in reproductive capacity or decreased fecundity, decrease in or cessation of feeding behavior or movement, or decrease in or cessation of metamorphosis stage development; in embodiments, application of an insecticidally effective amount of the recombinant RNA molecule to a plant improves the plant's resistance to infestation by the insect.

In embodiments of the insecticidal composition, the recombinant RNA molecule includes at least one RNA strand having a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 30-42, 45, and 46. In specific embodiments, the recombinant RNA molecule is a dsRNA including an RNA strand having a sequence selected from the group consisting of SEQ ID NOs:13-26, 28-29, 30-42, 45, and 46. In embodiments, the recombinant RNA molecule is a dsRNA of at least 50 base pairs in length. In embodiments of the method, the recombinant RNA molecule is dsRNA. In embodiments, the recombinant RNA molecule is a dsRNA which can be blunt-ended dsRNA, or can be dsRNA with an overhang at one or both ends (termini); the overhang can be a single nucleotide or 2, 3, 4, 5, 6, or more nucleotides, and can be located on the 5' end or on the 3' end of a strand. In embodiments, the recombinant RNA molecule is a dsRNA which can be chemically synthesized, or can be produced by expression in a microorganism, by expression in a plant cell, or by microbial fermentation. In embodiments, the recombinant RNA molecule is a dsRNA of a length greater than that which is typical of naturally occurring regulatory small RNAs (such as endogenously produced siRNAs and mature miRNAs), i. e., the polynucleotide is double-stranded RNA of at least about 30 contiguous base-pairs in length. In embodiments, the recombinant RNA molecule is a dsRNA with a length of between about 50 to about 500 base-pairs.

Embodiments of the insecticidal composition include those wherein the insect is *Spodoptera frugiperda* (fall armyworm) and the target gene includes a DNA sequence selected from the group consisting of SEQ ID NOs:1-3; wherein the insect is *Lygus hesperus* (western tarnished plant bug) and the target gene includes a DNA sequence selected from the group consisting of SEQ ID NOs:4-7, 43, and 44; wherein the insect is *Euschistus heros* (neotropical brown stink bug) and the target gene includes a DNA sequence selected from the group consisting of SEQ ID NOs:8-9; and wherein the insect is *Plutella xylostella* (diamondback moth) and the target gene includes a DNA sequence selected from the group consisting of SEQ ID NOs:10-12. Other embodiments of the insecticidal composition include those wherein the insect is *Spodoptera frugiperda* (fall armyworm) and the recombinant RNA molecule includes at least one RNA strand having a sequence of about 95% to about 100% (e. g., about 95%, about 96%, about 97%, about 98%, about 99%, or about 100%) identity or complementarity with a sequence selected from the group consisting of SEQ ID NOs:17-19; wherein the insect is *Lygus hesperus* (western tarnished plant bug) and the recombinant RNA molecule includes at least one RNA strand having a sequence of about 95% to about 100% (e. g., about 95%, about 96%, about 97%, about 98%, about 99%, or about 100%) identity or complementarity with a sequence selected from the group consisting of SEQ ID NOs:14-16, 22, 26, 45, and 46; wherein the insect is *Euschistus heros* (neotropical brown stink bug) and the recombinant RNA molecule includes at least one RNA strand having a sequence of about 95% to about 100% identity or complementarity with a sequence selected from the group consisting of SEQ ID NOs:23-25; and wherein the insect is *Plutella xylostella* (diamondback moth) and the recombinant RNA molecule includes at least one RNA strand having a sequence of about 95% to about 100% (e. g., about 95%, about 96%, about 97%, about 98%, about 99%, or about 100%) identity or complementarity with a sequence selected from the group consisting of SEQ ID NOs:13, 20-21, and 28-29. Specific embodiments of the insecticidal composition include those wherein the insect is *Spodoptera frugiperda* (fall armyworm) and the recombinant RNA molecule is a dsRNA including an RNA strand having a sequence selected from the group consisting of SEQ ID NOs:17-19; wherein the insect is *Lygus hesperus* (western tarnished plant bug) and recombinant RNA molecule is a dsRNA including an RNA strand having a sequence selected from the group consisting of SEQ ID NOs:14-16, 22, 26, 45, and 46; wherein the insect is *Euschistus heros* (neotropical brown stink bug) and recombinant RNA molecule is a dsRNA including an RNA strand having a sequence selected from the group consisting of SEQ ID NOs:23-25; and wherein the insect is *Plutella xylostella* (diamondback moth) and recombinant RNA molecule is a dsRNA including an RNA strand having a sequence selected from the group consisting of SEQ ID NOs:13, 20-21, and 28-29. Other embodiments of the insecticidal composition include those where the recombinant RNA molecule has a sequence modified as described in Example 5 to eliminate matches to non-target organisms, such as the modified sequences (SEQ ID NOs:30-42) disclosed in Table 6.

In various embodiments the insecticidal composition includes an insecticidally effective amount of a recombinant RNA molecule that consists of naturally occurring ribonucleotides, such as those found in naturally occurring RNA. In certain embodiments, the polynucleotide is a combination of ribonucleotides and deoxyribonucleotides, for example, synthetic polynucleotides consisting mainly of ribonucleotides but with one or more terminal deoxyribonucleotides or one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g., fluorescein or rhodamine) or other label (e. g., biotin).

The recombinant RNA molecule of is provided by suitable means known to one in the art. Embodiments include those wherein the recombinant RNA molecule is chemically synthesized (e. g., by in vitro transcription, such as transcription using a T7 polymerase or other polymerase), produced by expression in a microorganism or in cell culture (such as plant or insect cells grown in culture), produced by expression in a plant cell, or produced by microbial fermentation.

In embodiments the recombinant RNA molecule of use in this method is provided as an isolated RNA fragment (not part of an expression construct, i. e., lacking additional elements such as a promoter or terminator sequences). Such recombinant RNA molecules can be relatively short, such as single- or double-stranded RNA molecules of between about 18 to about 300 or between about 50 to about 500 nucleotides (for single-stranded polynucleotides) or between about 18 to about 300 or between about 50 to about 500 base-pairs (for double-stranded polynucleotides). Embodiments include those in which the polynucleotide is a dsRNA including a segment having a sequence selected from the group consisting of SEQ ID NOs:13-26, 28-29, 30-42, 45, and 46.

In embodiments, the insecticidal composition is in a form selected from the group consisting of a solid, liquid, powder, suspension, emulsion, spray, encapsulation, microbeads, carrier particulates, film, matrix, soil drench, insect diet or insect bait, and seed treatment. In embodiments, the insecticidal composition can be applied to a seed, e. g., by soaking the seed in a liquid insecticidal composition including the dsRNA, wherein the seed imbibes or takes up the dsRNA into the seed interior or seed endosperm in an effective amount to provide improved resistance to the insect pest by the seed or a plant or seedling grown from the seed. In some embodiments, the insecticidal composition is provided in a form that is ingested by the insect, such as in a liquid, emulsion, or powder applied to a plant on which the insect feeds, or in the form of bait. The insecticidal compositions can further include one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator. The insecticidal compositions can further include at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, the combination of the recombinant RNA molecule and the pesticidal agent provides a level of insect control that is synergistic, i. e., greater than the sum of the effects of the recombinant RNA molecule and the pesticidal agent components if tested separately.

A related aspect of the invention is a plant treated with an insecticidal composition as described herein, or a seed of the treated plant, wherein the plant exhibits improved resistance to the insect. In embodiments, the plant exhibiting improved resistance to the insect is characterized by improved yield, when compared to a plant not treated with the insecticidal composition.

Methods of Providing Plants with Improved Insect Resistance

Another aspect of the invention provides a method of providing a plant having improved resistance to an insect, including expressing in the plant a recombinant DNA construct including DNA encoding RNA that includes at least one silencing element essentially identical or essentially complementary to a fragment of a target gene sequence of the insect, wherein the target gene sequence is selected from the group consisting of SEQ ID NOs:1-12 and 43-44, and wherein ingestion of the RNA by the insect results in mortality or stunting in the insect.

In embodiments of the method, the silencing element has a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 45, and 46. In specific embodiments, the silencing element is RNA that forms double-stranded RNA from two separate, essentially complementary strands, wherein at least one RNA strand includes a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 45, and 46. In other embodiments, the silencing element is RNA that forms double-stranded RNA from a single self-hybridizing hairpin transcript, wherein one "arm" of the hairpin includes a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 45, and 46. Other embodiments include those where the silencing element has a sequence modified as described in Example 5 to eliminate matches to non-target organisms, such as the modified sequences (SEQ ID NOs:30-42) disclosed in Table 6.

In embodiments of the method, the recombinant DNA construct further includes a heterologous promoter operably linked to the DNA encoding RNA that includes at least one silencing element, wherein the heterologous promoter is functional in a plant cell. Promoters functional in a plant cell include those listed under the heading "Promoters".

In embodiments of the method, the recombinant DNA construct is expressed in the plant by means of transgenic expression or transient expression. In some embodiments, the method further includes expression in the plant of at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. The pesticidal agent can be expressed from the same recombinant DNA construct that includes the DNA encoding at least one silencing element, or from a different recombinant DNA construct.

A related aspect of the invention is a plant having improved resistance to an insect, or the seed of such a plant, wherein the plant is provided by the method including expressing in the plant a recombinant DNA construct including DNA encoding RNA that includes at least one silencing element essentially identical or essentially complementary to a fragment of a target gene sequence of the insect, wherein the target gene sequence is selected from the group consisting of SEQ ID NOs:1-12 and 43-44, and wherein ingestion of the RNA by the insect results in mortality or stunting in the insect. In embodiments, the plant exhibiting improved resistance to the insect is characterized by improved yield, when compared to a plant not treated with the insecticidal composition. Also encompassed by the invention are fruit, seed, or propagatable parts of the plant provided by this method and exhibiting improved resistance to the insect.

A related aspect of the invention is a plant or seedling having improved resistance to an insect, wherein the plant or seedling is grown from a seed treated with a recombinant DNA construct including DNA encoding RNA that includes at least one silencing element essentially identical or essentially complementary to a fragment of a target gene sequence of the insect, wherein the target gene sequence is selected from the group consisting of SEQ ID NOs:1-12 and 43-44; alternatively the plant is grown from a seed directly treated with the RNA that includes at least one silencing element essentially identical or essentially complementary to a fragment of a target gene sequence of the insect, wherein the target gene sequence is selected from the group consisting of SEQ ID NOs:1-12 and 43-44. In embodiments, the recombinant DNA construct (or the encoded RNA that includes at least one silencing element) is applied by soaking the seed in a liquid composition including the recombinant DNA construct (or the encoded RNA that includes at least one silencing element), wherein the seed imbibes or takes up the DNA or encoded RNA into the seed interior or seed endosperm in an effective amount to provide improved resistance to the insect pest by a plant or seedling grown from the seed.

Recombinant DNA Constructs Encoding RNA for Insect Control

Another aspect of the invention provides a recombinant DNA construct including a heterologous promoter operably linked to DNA encoding an RNA transcript including a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 30-42, 45, and 46.

In specific embodiments, the RNA transcript forms double-stranded RNA from two separate, essentially complementary strands (e. g., where one strand is encoded on a separate DNA construct or where the two strands are encoded on separate sections of the DNA encoding an RNA transcript, and which are separately transcribed or made separate, for example, by the action of a recombinase or nuclease), wherein at least one RNA strand includes a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 30-42, 45, and 46. In other embodiments, the RNA transcript forms double-stranded RNA from a single self-hybridizing hairpin transcript, wherein one "arm" of the hairpin includes a sequence of about 95% to about 100% (e. g., about 95%, about 96%, about 97%, about 98%, about 99%, or about 100%) identity or complementarity with a sequence selected from the group consisting of SEQ ID NOs:13-26, 28-29, 30-42, 45, and 46.

Embodiments of the recombinant DNA construct include those wherein the heterologous promoter is functional for expression of the RNA transcript in a bacterium. In embodiments where the recombinant DNA construct is to be expressed in a bacterium, the bacterium is selected from the group consisting of *Escherichia coli*, *Bacillus* species, *Pseudomonas* species, *Xenorhabdus* species, or *Photorhabdus* species. In other embodiments, the recombinant DNA construct includes a heterologous promoter that is functional in a plant cell. In embodiments, the recombinant DNA construct is contained in a recombinant vector, such as a recombinant plant virus vector or a recombinant baculovirus vector. In embodiments, the recombinant DNA construct is integrated into a plant chromosome or plastid, e. g., by stable transformation.

Related aspects of the invention include a transgenic plant cell having in its genome the recombinant DNA construct, and a transgenic plant including such a transgenic plant cell. Transgenic plant cells and plants are made by methods known in the art, such as those described under the heading "Making and Using Transgenic Plant Cells and Transgenic Plants". Further aspects of the invention include a commodity product produced from such a transgenic plant, and transgenic progeny seed or propagatable plant part of the transgenic plant.

Related Information and Techniques

Plants

The methods and compositions described herein for treating and protecting plants from insect infestations are useful across a broad range of plants. Suitable plants in which the methods and compositions disclosed herein can be used include, but are not limited to, cereals and forage grasses (rice, maize, wheat, barley, oat, sorghum, pearl millet, finger millet, cool-season forage grasses, and bahiagrass), oilseed crops (soybean, oilseed brassicas including canola and oilseed rape, sunflower, peanut, flax, sesame, and safflower), legume grains and forages (common bean, cowpea, pea, faba bean, lentil, tepary bean, Asiatic beans, pigeonpea, vetch, chickpea, lupine, alfalfa, and clovers), temperate fruits and nuts (apple, pear, peach, plums, berry crops, cherries, grapes, olive, almond, and Persian walnut), tropical and subtropical fruits and nuts (citrus including limes, oranges, and grapefruit; banana and plantain, pineapple, papaya, mango, avocado, kiwifruit, passionfruit, and persimmon), vegetable crops (solanaceous plants including tomato, eggplant, and peppers; vegetable brassicas; radish, carrot, cucurbits, alliums, asparagus, and leafy vegetables), sugar, tuber, and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species.

Additional Construct Elements

Embodiments of the polynucleotides and nucleic acid molecules of this invention can include additional elements, such as promoters, small RNA recognition sites, aptamers or ribozymes, additional and additional expression cassettes for expressing coding sequences (e. g., to express a transgene such as an insecticidal protein or selectable marker) or non-coding sequences (e. g., to express additional suppression elements). For example, an aspect of this invention provides a recombinant DNA construct including a heterologous promoter operably linked to DNA encoding an RNA transcript that includes a sequence of about 95% to about 100% identity or complementarity with a sequence selected from the group consisting of SEQ ID NOs:13-26, 28-29, 30-42, 45, and 46. In another embodiment, a recombinant DNA construct including a promoter operably linked to DNA encoding: (a) an RNA transcript that includes a sequence of about 95% to about 100% identity or complementarity with a sequence selected from the group consisting of SEQ ID NOs:13-26, 28-29, 30-42, 45, and 46, and (b) an aptamer, is stably integrated into the plant's genome from where RNA transcripts including the RNA aptamer and the RNA silencing element are expressed in cells of the plant; the aptamer serves to guide the RNA silencing element to a desired location in the cell. In another embodiment, inclusion of one or more recognition sites for binding and cleavage by a small RNA (e. g., by a miRNA or an siRNA that is expressed only in a particular cell or tissue) allows for more precise expression patterns in a plant, wherein the expression of the recombinant DNA construct is suppressed where the small RNA is expressed. Such additional elements are described below.

Promoters

Promoters of use in the invention are functional in the cell in which the construct is intended to be transcribed. Generally these promoters are heterologous promoters, as used in recombinant constructs, i. e., they are not in nature found to be operably linked to the other nucleic elements used in the constructs of this invention. In various embodiments, the promoter is selected from the group consisting of a constitutive promoter, a spatially specific promoter, a temporally specific promoter, a developmentally specific promoter, and an inducible promoter. In many embodiments the promoter is a promoter functional in a plant, for example, a pol II promoter, a pol III promoter, a pol IV promoter, or a pol V promoter.

Non-constitutive promoters suitable for use with the recombinant DNA constructs of this invention include spatially specific promoters, temporally specific promoters, and inducible promoters. Spatially specific promoters can include organelle-, cell-, tissue-, or organ-specific promoters (e. g., a plastid-specific, a root-specific, a pollen-specific, or a seed-specific promoter for expression in plastids, roots, pollen, or seeds, respectively). In many cases a seed-specific, embryo-specific, aleurone-specific, or endosperm-specific promoter is especially useful. Temporally specific promoters can include promoters that tend to promote expression during certain developmental stages in a plant's growth cycle, or during different times of day or night, or at different seasons in a year. Inducible promoters include promoters induced by chemicals or by environmental conditions such as, but not limited to, biotic or abiotic stress (e. g., water deficit or drought, heat, cold, high or low nutrient or salt levels, high or low light levels, or pest or pathogen infection). MicroRNA promoters are useful, especially those having a temporally specific, spatially specific, or inducible expression pattern; examples of miRNA promoters, as well as methods for identifying miRNA promoters having specific expression patterns, are provided in U.S. Patent Application Publications 2006/0200878, 2007/0199095, and 2007/0300329, which are specifically incorporated herein by reference. An expression-specific promoter can also include promoters that are generally constitutively expressed but at differing degrees or "strengths" of expression, including promoters commonly regarded as "strong promoters" or as "weak promoters".

Promoters of particular interest include the following examples: an opaline synthase promoter isolated from T-DNA of *Agrobacterium*; a cauliflower mosaic virus 35S promoter; enhanced promoter elements or chimeric promoter elements such as an enhanced cauliflower mosaic virus (CaMV) 35S promoter linked to an enhancer element (an intron from heat shock protein 70 of *Zea mays*); root specific promoters such as those disclosed in U.S. Pat. Nos. 5,837,848; 6,437,217 and 6,426,446; a maize L3 oleosin promoter disclosed in U.S. Pat. No. 6,433,252; a promoter for a plant nuclear gene encoding a plastid-localized aldolase disclosed in U.S. Patent Application Publication 2004/0216189; cold-inducible promoters disclosed in U.S. Pat. No. 6,084,089; salt-inducible promoters disclosed in U.S. Pat. No. 6,140,078; light-inducible promoters disclosed in U.S. Pat. No. 6,294,714; pathogen-inducible promoters disclosed in U.S. Pat. No. 6,252,138; and water deficit-inducible promoters disclosed in U.S. Patent Application Publication 2004/0123347 A1. All of the above-described patents and patent publications disclosing promoters and their use, especially in recombinant DNA constructs functional in plants are incorporated herein by reference.

Plant vascular- or phloem-specific promoters of interest include a rolC or rolA promoter of *Agrobacterium rhizogenes*, a promoter of a *Agrobacterium tumefaciens* T-DNA gene 5, the rice sucrose synthase RSs1 gene promoter, a *Commelina* yellow mottle badnavirus promoter, a coconut foliar decay virus promoter, a rice tungro bacilliform virus promoter, the promoter of a pea glutamine synthase GS3A gene, a invCD111 and invCD141 promoters of a potato invertase genes, a promoter isolated from *Arabidopsis* shown to have phloem-specific expression in tobacco by Kertbundit et al. (1991) *Proc. Natl. Acad. Sci. US A.,* 88:5212-5216, a VAHOX1 promoter region, a pea cell wall invertase gene promoter, an acid invertase gene promoter from carrot, a promoter of a sulfate transporter gene Sultr1; 3, a promoter of a plant sucrose synthase gene, and a promoter of a plant sucrose transporter gene.

Promoters suitable for use with a recombinant DNA construct or polynucleotide of this invention include polymerase II ("pol II") promoters and polymerase III ("pol III") promoters. RNA polymerase II transcribes structural or catalytic RNAs that are usually shorter than 400 nucleotides in length, and recognizes a simple run of T residues as a termination signal; it has been used to transcribe siRNA duplexes (see, e. g., Lu et al. (2004) *Nucleic Acids Res.,* 32:e171). Pol II promoters are therefore preferred in certain embodiments where a short RNA transcript is to be produced from a recombinant DNA construct of this invention. In one embodiment, the recombinant DNA construct includes a pol II promoter to express an RNA transcript flanked by self-cleaving ribozyme sequences (e. g., self-cleaving hammerhead ribozymes), resulting in a processed RNA, such as a single-stranded RNA that binds to the transcript of the *Leptinotarsa* target gene, with defined 5' and 3' ends, free of potentially interfering flanking sequences. An alternative approach uses pol III promoters to generate transcripts with relatively defined 5' and 3' ends, i. e., to transcribe an RNA with minimal 5' and 3' flanking sequences. In some embodiments, Pol III promoters (e. g., U6 or H1 promoters) are preferred for adding a short AT-rich transcription termination site that results in 2 base-pair overhangs (UU) in the transcribed RNA; this is useful, e. g., for expression of siRNA-type constructs. Use of pol III promoters for driving expression of siRNA constructs has been reported; see van de Wetering et al. (2003) *EMBO Rep.,* 4: 609-615, and Tuschl (2002) *Nature Biotechnol.,* 20: 446-448. Baculovirus promoters such as baculovirus polyhedrin and p10 promoters are known in the art and commercially available; see, e. g., Invitrogen's "Guide to Baculovirus Expression Vector Systems (BEVS) and Insect Cell Culture Techniques", 2002 (Life Technologies, Carlsbad, Calif.) and F. J. Haines et al. "Baculovirus Expression Vectors", undated (Oxford Expression Technologies, Oxford, UK).

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer (see "Aptamers", below) and a regulatory region (which can be cis-acting). See, for example, Isaacs et al. (2004) *Nat. Biotechnol.,* 22:841-847, Bayer and Smolke (2005) *Nature Biotechnol.,* 23:337-343, Mandal and Breaker (2004) *Nature Rev. Mol. Cell Biol.,* 5:451-463, Davidson and Ellington (2005) *Trends Biotechnol.,* 23:109-112, Winkler et al. (2002) *Nature,* 419:952-956, Sudarsan et al. (2003) *RNA,* 9:644-647, and Mandal and Breaker (2004) *Nature Struct. Mol. Biol.,* 11:29-35. Such "riboregulators" could be selected or designed for specific spatial or temporal specificity, for example, to regulate translation of DNA that encodes a silencing element for suppressing a target gene only in the presence (or absence) of a given concentration of the appropriate ligand. One example is a riboregulator that is responsive to an endogenous ligand (e. g., jasmonic acid or salicylic acid) produced by the plant when under stress (e. g., abiotic stress such as water, temperature, or nutrient stress, or biotic stress such as attach by pests or pathogens); under stress, the level of endogenous ligand increases to a level sufficient for the riboregulator to begin transcription of the DNA that encodes a silencing element for suppressing a target gene.

Recombinase Sites

In some embodiments, the recombinant DNA construct or polynucleotide of this invention includes DNA encoding one or more site-specific recombinase recognition sites. In one embodiment, the recombinant DNA construct includes at least a pair of loxP sites, wherein site-specific recombination of DNA between the loxP sites is mediated by a Cre recombinase. The position and relative orientation of the loxP sites is selected to achieve the desired recombination; for example, when the loxP sites are in the same orientation, the DNA between the loxP sites is excised in circular form. In another embodiment, the recombinant DNA construct includes DNA encoding one loxP site; in the presence of Cre recombinase and another DNA with a loxP site, the two DNAs are recombined.

Aptamers

In some embodiments, the recombinant DNA construct or polynucleotide of this invention includes DNA that is processed to an RNA aptamer, that is, an RNA that binds to a ligand through binding mechanism that is not primarily based on Watson-Crick base-pairing (in contrast, for example, to the base-pairing that occurs between complementary, anti-parallel nucleic acid strands to form a double-stranded nucleic acid structure). See, for example, Ellington and Szostak (1990) *Nature*, 346:818-822. Examples of aptamers can be found, for example, in the public Aptamer Database, available on line at aptamer.icmb.utexas.edu (Lee et al. (2004) *Nucleic Acids Res.*, 32(1):D95-100). Aptamers useful in the invention can, however, be monovalent (binding a single ligand) or multivalent (binding more than one individual ligand, e. g., binding one unit of two or more different ligands).

Ligands useful in the invention include any molecule (or part of a molecule) that can be recognized and be bound by a nucleic acid secondary structure by a mechanism not primarily based on Watson-Crick base pairing. In this way, the recognition and binding of ligand and aptamer is analogous to that of antigen and antibody, or of biological effector and receptor. Ligands can include single molecules (or part of a molecule), or a combination of two or more molecules (or parts of a molecule), and can include one or more macromolecular complexes (e. g., polymers, lipid bilayers, liposomes, cellular membranes or other cellular structures, or cell surfaces). Examples of specific ligands include vitamins such as coenzyme $B_{12}$ and thiamine pyrophosphate, flavin mononucleotide, guanine, adenosine, S-adenosylmethionine, S-adenosylhomocysteine, coenzyme A, lysine, tyrosine, dopamine, glucosamine-6-phosphate, caffeine, theophylline, antibiotics such as chloramphenicol and neomycin, herbicides such as glyphosate and dicamba, proteins including viral or phage coat proteins and invertebrate epidermal or digestive tract surface proteins, and RNAs including viral RNA, transfer-RNAs (t-RNAs), ribosomal RNA (rRNA), and RNA polymerases such as RNA-dependent RNA polymerase (RdRP). One class of RNA aptamers useful in the invention are "thermoswitches" that do not bind a ligand but are thermally responsive, that is to say, the aptamer's conformation is determined by temperature; see, for example, Box 3 in Mandal and Breaker (2004) *Nature Rev. Mol. Cell Biol.*, 5:451-463.

Transgene Transcription Units

In some embodiments, the recombinant DNA construct or polynucleotide of this invention includes a transgene transcription unit. A transgene transcription unit includes DNA sequence encoding a gene of interest, e. g., a natural protein or a heterologous protein. A gene of interest can be any coding or non-coding sequence from any species (including, but not limited to, non-eukaryotes such as bacteria, and viruses; fungi, protists, plants, invertebrates, and vertebrates. Particular genes of interest are genes encoding at least one pesticidal agent selected from the group consisting of a patatin, a plant lectin, a phytoecdysteroid, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. The transgene transcription unit can further include 5' or 3' sequence or both as required for transcription of the transgene.

Introns

In some embodiments, the recombinant DNA construct or polynucleotide of this invention includes DNA encoding a spliceable intron. By "intron" is generally meant a segment of DNA (or the RNA transcribed from such a segment) that is located between exons (protein-encoding segments of the DNA or corresponding transcribed RNA), wherein, during maturation of the messenger RNA, the intron present is enzymatically "spliced out" or removed from the RNA strand by a cleavage/ligation process that occurs in the nucleus in eukaryotes. The term "intron" is also applied to non-coding DNA sequences that are transcribed to RNA segments that can be spliced out of a maturing RNA transcript, but are not introns found between protein-coding exons. One example of these are spliceable sequences that have the ability to enhance expression in plants (in some cases, especially in monocots) of a downstream coding sequence; these spliceable sequences are naturally located in the 5' untranslated region of some plant genes, as well as in some viral genes (e. g., the tobacco mosaic virus 5' leader sequence or "omega" leader described as enhancing expression in plant genes by Gallie and Walbot (1992) *Nucleic Acids Res.*, 20:4631-4638). These spliceable sequences or "expression-enhancing introns" can be artificially inserted in the 5' untranslated region of a plant gene between the promoter and any protein-coding exons. Examples of such expression-enhancing introns include, but are not limited to, a maize alcohol dehydrogenase (Zm-Adh1), a maize Bronze-1 expression-enhancing intron, a rice actin 1 (Os-Act1) intron, a Shrunken-1 (Sh-1) intron, a maize sucrose synthase intron, a heat shock protein 18 (hsp18) intron, and an 82 kilodalton heat shock protein (hsp82) intron. U.S. Pat. Nos. 5,593,874 and 5,859,347, specifically incorporated by reference herein, describe methods of improving recombinant DNA constructs for use in plants by inclusion of an expression-enhancing intron derived from the 70 kilodalton maize heat shock protein (hsp70) in the non-translated leader positioned 3' from the gene promoter and 5' from the first protein-coding exon.

Ribozymes

In some embodiments, the recombinant DNA construct or polynucleotide of this invention includes DNA encoding one or more ribozymes. Ribozymes of particular interest include a self-cleaving ribozyme, a hammerhead ribozyme, or a hairpin ribozyme. In one embodiment, the recombinant DNA construct includes DNA encoding one or more ribozymes that serve to cleave the transcribed RNA to provide defined segments of RNA, such as silencing elements for suppressing a *Leptinotarsa* target gene.

Gene Suppression Elements

In some embodiments, the recombinant DNA construct or polynucleotide of this invention includes DNA encoding additional gene suppression element for suppressing a target gene other than a *Leptinotarsa* target gene. The target gene to be suppressed can include coding or non-coding sequence or both.

Suitable gene suppression elements are described in detail in U.S. Patent Application Publication 2006/0200878, which disclosure is specifically incorporated herein by reference, and include one or more of:

(a) DNA that includes at least one anti-sense DNA segment that is anti-sense to at least one segment of the gene to be suppressed;
(b) DNA that includes multiple copies of at least one anti-sense DNA segment that is anti-sense to at least one segment of the gene to be suppressed;
(c) DNA that includes at least one sense DNA segment that is at least one segment of the gene to be suppressed;
(d) DNA that includes multiple copies of at least one sense DNA segment that is at least one segment of the gene to be suppressed;
(e) DNA that transcribes to RNA for suppressing the gene to be suppressed by forming double-stranded RNA and includes at least one anti-sense DNA segment that is anti-sense to at least one segment of the gene to be suppressed and at least one sense DNA segment that is at least one segment of the gene to be suppressed;
(f) DNA that transcribes to RNA for suppressing the gene to be suppressed by forming a single double-stranded RNA and includes multiple serial anti-sense DNA segments that are anti-sense to at least one segment of the gene to be suppressed and multiple serial sense DNA segments that are at least one segment of the gene to be suppressed;
(g) DNA that transcribes to RNA for suppressing the gene to be suppressed by forming multiple double strands of RNA and includes multiple anti-sense DNA segments that are anti-sense to at least one segment of the gene to be suppressed and multiple sense DNA segments that are at least one segment of the gene to be suppressed, and wherein the multiple anti-sense DNA segments and the multiple sense DNA segments are arranged in a series of inverted repeats;
(h) DNA that includes nucleotides derived from a plant miRNA;
(i) DNA that includes nucleotides of a siRNA;
(j) DNA that transcribes to an RNA aptamer capable of binding to a ligand; and
(k) DNA that transcribes to an RNA aptamer capable of binding to a ligand, and DNA that transcribes to regulatory RNA capable of regulating expression of the gene to be suppressed, wherein the regulation is dependent on the conformation of the regulatory RNA, and the conformation of the regulatory RNA is allosterically affected by the binding state of the RNA aptamer.

In some embodiments, an intron is used to deliver a gene suppression element in the absence of any protein-coding exons (coding sequence). In one example, an intron, such as an expression-enhancing intron (preferred in certain embodiments), is interrupted by embedding within the intron a gene suppression element, wherein, upon transcription, the gene suppression element is excised from the intron. Thus, protein-coding exons are not required to provide the gene suppressing function of the recombinant DNA constructs disclosed herein.

Transcription Regulatory Elements

In some embodiments, the recombinant DNA construct or polynucleotide of this invention includes DNA encoding a transcription regulatory element. Transcription regulatory elements include elements that regulate the expression level of the recombinant DNA construct of this invention (relative to its expression in the absence of such regulatory elements). Examples of suitable transcription regulatory elements include riboswitches (cis- or trans-acting), transcript stabilizing sequences, and miRNA recognition sites, as described in detail in U.S. Patent Application Publication 2006/0200878, specifically incorporated herein by reference.

Making and Using Transgenic Plant Cells and Transgenic Plants

Transformation of a plant can include any of several well-known methods and compositions. Suitable methods for plant transformation include virtually any method by which DNA can be introduced into a cell. One method of plant transformation is microprojectile bombardment, for example, as illustrated in U.S. Pat. No. 5,015,580 (soybean), U.S. Pat. No. 5,538,880 (maize), U.S. Pat. No. 5,550,318 (maize), U.S. Pat. No. 5,914,451 (soybean), U.S. Pat. No. 6,153,812 (wheat), U.S. Pat. No. 6,160,208 (maize), U.S. Pat. No. 6,288,312 (rice), U.S. Pat. No. 6,365,807 (rice), and U.S. Pat. No. 6,399,861 (maize), and U.S. Pat. No. 6,403,865 (maize), all of which are incorporated by reference for enabling the production of transgenic plants.

Another useful method of plant transformation is *Agrobacterium*-mediated transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a polynucleotide or recombinant DNA construct of this invention. See, for example, the binary system described in U.S. Pat. No. 5,159,135, incorporated by reference. Also see De Framond (1983) *Biotechnology,* 1:262-269; and Hoekema et al., (1983) *Nature,* 303:179. In such a binary system, the smaller plasmid, containing the T-DNA border or borders, can be conveniently constructed and manipulated in a suitable alternative host, such as *E. coli*, and then transferred into *Agrobacterium.*

Detailed procedures for *Agrobacterium*-mediated transformation of plants, especially crop plants, include procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soybean); U.S. Pat. Nos. 5,591,616 and 5,981,840 (maize); U.S. Pat. No. 5,463,174 (brassicas including canola), U.S. Pat. No. 7,026,528 (wheat), and U.S. Pat. No. 6,329,571 (rice), and in U.S. Patent Application Publications 2004/0244075 (maize) and 2001/0042257 A1 (sugar beet), all of which are specifically incorporated by reference for enabling the production of transgenic plants. U.S. Patent Application Publication 2011/0296555 discloses in Example 5 the transformation vectors (including the vector sequences) and detailed protocols for transforming maize, soybean, canola, cotton, and sugarcane) and is specifically incorporated by reference for enabling the production of transgenic plants. Similar methods have been reported for many plant species, both dicots and monocots, including, among others, peanut (Cheng et al. (1996) *Plant Cell Rep.,* 15: 653); asparagus (Bytebier et al. (1987) *Proc. Natl. Acad. Sci. U.S.A.,* 84:5345); barley (Wan and Lemaux (1994) *Plant Physiol.,* 104:37); rice (Toriyama et al. (1988) *Bio/Technology,* 6:10; Zhang et al. (1988) *Plant Cell Rep.,* 7:379; wheat (Vasil et al. (1992) *Bio/Technology,* 10:667; Becker et al. (1994) *Plant J.,* 5:299), alfalfa (Masoud et al. (1996) *Transgen. Res.,* 5:313); and tomato (Sun et al. (2006) *Plant Cell Physiol.,* 47:426-431). See also a description of vectors, transformation methods, and production of transformed *Arabidopsis thaliana* plants where transcription factors are constitutively expressed by a CaMV35S promoter, in U.S. Patent Application Publication 2003/0167537 A1, incorporated by reference. Transformation methods specifically useful for solanaceous plants are well known in the art. See, for example, publicly described transformation methods for tomato (Sharma et al. (2009), *J. Biosci.,* 34:423-433), eggplant (Arpaia et al. (1997) *Theor. Appl. Genet.,* 95:329-334), potato (Bannerjee et al. (2006) *Plant Sci.,* 170:732-738; Chakravarty et al. (2007) *Amer. J. Potato Res.,* 84:301-311; S. Millam "*Agrobacterium*-mediated transformation of potato." Chapter 19 (pp. 257-270), "Transgenic Crops of the World: Essential Protocols", Ian S. Curtis (editor), Springer, 2004), and peppers (Li et al. (2003) *Plant Cell Reports,* 21: 785-788). Stably transgenic potato, tomato, and eggplant have been commercially introduced in various regions; see, e. g., K. Redenbaugh et al. "Safety Assessment of Genetically Engineered Fruits and Vegetables: A Case Study of the FLAVR SAVR™ Tomato", CRC Press, Boca Raton, 1992, and the extensive publicly available documentation of commercial genetically modified crops in the GM Crop Database; see: CERA. (2012). GM Crop Database. Center for Environmental Risk Assessment (CERA), ILSI Research Foundation, Washington D.C., available electronically at www.cera-gmc.org/?action=gm_crop_database. Various methods of transformation of other plant species are well known in the art, see, for example, the encyclopedic reference, "Compendium of Transgenic Crop Plants", edited by Chittaranjan Kole and Timothy C. Hall, Blackwell Publishing Ltd., 2008; ISBN 978-1-405-16924-0 (available electronically at mrw.interscience.wiley.com/emrw/9781405181099/hpt/toc), which describes transformation procedures for cereals and forage grasses (rice, maize, wheat, barley, oat, sorghum, pearl millet, finger millet, cool-season forage grasses, and bahiagrass), oilseed crops (soybean, oilseed brassicas, sunflower, peanut, flax, sesame, and safflower), legume grains and forages (common bean, cowpea, pea, faba bean, lentil, tepary bean, Asiatic beans, pigeonpea, vetch, chickpea, lupine, alfalfa, and clovers), temperate fruits and nuts (apple, pear, peach, plums, berry crops, cherries, grapes, olive, almond, and Persian walnut), tropical and subtropical fruits and nuts (citrus, grapefruit, banana and plantain, pineapple, papaya, mango, avocado, kiwifruit, passionfruit, and persimmon), vegetable crops (tomato, eggplant, peppers, vegetable brassicas, radish, carrot, cucurbits, alliums, asparagus, and leafy vegetables), sugar, tuber, and fiber crops (sugarcane, sugar beet, stevia, potato, sweet potato, cassava, and cotton), plantation crops, ornamentals, and turf grasses (tobacco, coffee, cocoa, tea, rubber tree, medicinal plants, ornamentals, and turf grasses), and forest tree species.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of this invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e. g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, which are specifically incorporated by reference.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell is resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047, all of which are specifically incorporated by reference. Screenable markers or reporters, such as markers that provide an ability to visually identify transformants can also be employed. Examples of useful screenable markers include, for example, a gene expressing a protein that produces a detectable color by acting on a chromogenic substrate (e. g., beta glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

Detecting or measuring transcription of a recombinant DNA construct in a transgenic plant cell can be achieved by any suitable method, including protein detection methods (e. g., western blots, ELISAs, and other immunochemical methods), measurements of enzymatic activity, or nucleic acid detection methods (e. g., Southern blots, northern blots, PCR, RT-PCR, fluorescent in situ hybridization).

Other suitable methods for detecting or measuring transcription in a plant cell of a recombinant polynucleotide of this invention targetting an insect target gene include measurement of any other trait that is a direct or proxy indication of the level of expression of the target gene in the insect, relative to the level of expression observed in the absence of the recombinant polynucleotide, e. g., growth rates, mortality rates, or reproductive or recruitment rates of the insect, or measurements of injury (e. g., root injury) or yield loss in a plant or field of plants infested by the insect. In general, suitable methods for detecting or measuring transcription in a plant cell of a recombinant polynucleotide of interest include, e. g., gross or microscopic morphological traits, growth rates, yield, reproductive or recruitment rates, resistance to pests or pathogens, or resistance to biotic or abiotic stress (e. g., water deficit stress, salt stress, nutrient stress, heat or cold stress). Such methods can use direct measurements of a phenotypic trait or proxy assays (e. g., in plants, these assays include plant part assays such as leaf or root assays to determine tolerance of abiotic stress). Such methods include direct measurements of resistance to an invertebrate pest or pathogen (e. g., damage to plant tissues) or proxy assays (e. g., plant yield assays, or invertebrate pest bioassays such as the Western corn rootworm (*Diabrotica virgifera virgifera* LeConte) larval bioassay described in International Patent Application Publication WO2005/110068 A2 and U.S. Patent Application Publication US 2006/0021087 A1, specifically incorporated by reference, or the soybean cyst nematode bioassay described by Steeves et al. (2006) *Funct. Plant Biol.*, 33:991-999, wherein cysts per plant, cysts per gram root, eggs per plant, eggs per gram root, and eggs per cyst are measured, or the bioassays described herein in the working Examples.

The recombinant DNA constructs of this invention can be stacked with other recombinant DNA for imparting additional traits (e. g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, specifically incorporated by reference.

Seeds of fertile transgenic plants can be harvested and used to grow progeny generations, including hybrid generations, of transgenic plants of this invention that include the recombinant DNA construct in their genome. Thus, in addition to direct transformation of a plant with a recombinant DNA construct of this invention, transgenic plants of this invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of this invention can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

In such breeding for combining traits the transgenic plant donating the additional trait can be a male line (pollinator) and the transgenic plant carrying the base traits can be the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e. g., usually 6 to 8 generations, to produce a homozygous progeny plant with substantially the same genotype as one original transgenic parental line as well as the recombinant DNA of the other transgenic parental line.

Yet another aspect of this invention is a transgenic plant grown from the transgenic seed of this invention. This invention contemplates transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed. Crossing can include, for example, the following steps:

(a) plant seeds of the first parent plant (e. g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e. g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny can be essentially hemizygous for loci controlling the characteristic being transferred, but are like the superior parent for most or almost all other genes. The last backcross generation would be selfed to give progeny which are pure breeding for the gene(s) being transferred, i. e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

In certain transgenic plant cells and transgenic plants of this invention, it is sometimes desirable to concurrently express a gene of interest while also modulating expression of a *Leptinotarsa* target gene. Thus, in some embodiments, the transgenic plant contains recombinant DNA further including a gene expression element for expressing at least one gene of interest, and transcription of the recombinant DNA construct of this invention is preferably effected with concurrent transcription of the gene expression element.

In some embodiments, the recombinant DNA constructs of this invention can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; plants grown for biomass or biofuel (for example, *Miscanthus* grasses, switchgrass, jatropha, oil palm, eukaryotic microalgae such as *Botryococcus braunii*, *Chlorella* spp., and *Dunaliella* spp., and eukaryotic macroalgae such as *Gracilaria* spp., and *Sargassum* spp.); and ornamental plants including ornamental flowering plants, ornamental trees and shrubs, ornamental groundcovers, and ornamental grasses.

This invention also provides commodity products produced from a transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a transgenic plant cell, plant, or seed of this invention.

Generally a transgenic plant having in its genome a recombinant DNA construct of this invention exhibits increased resistance to an insect infestation. In various embodiments, for example, where the transgenic plant expresses a recombinant DNA construct of this invention that is stacked with other recombinant DNA for imparting additional traits, the transgenic plant has at least one additional altered trait, relative to a plant lacking the recombinant DNA construct, selected from the group of traits consisting of:

(a) improved abiotic stress tolerance;
(b) improved biotic stress tolerance;
(c) modified primary metabolite composition;
(d) modified secondary metabolite composition;
(e) modified trace element, carotenoid, or vitamin composition;
(f) improved yield;
(g) improved ability to use nitrogen, phosphate, or other nutrients;
(h) modified agronomic characteristics;
(i) modified growth or reproductive characteristics; and
(j) improved harvest, storage, or processing quality.

In some embodiments, the transgenic plant is characterized by: improved tolerance of abiotic stress (e. g., tolerance of water deficit or drought, heat, cold, non-optimal nutrient or salt levels, non-optimal light levels) or of biotic stress (e. g., crowding, allelopathy, or wounding); by a modified primary metabolite (e. g., fatty acid, oil, amino acid, protein, sugar, or carbohydrate) composition; a modified secondary metabolite (e. g., alkaloids, terpenoids, polyketides, non-ribosomal peptides, and secondary metabolites of mixed biosynthetic origin) composition; a modified trace element (e. g., iron, zinc), carotenoid (e. g., beta-carotene, lycopene, lutein, zeaxanthin, or other carotenoids and xanthophylls), or vitamin (e. g., tocopherols) composition; improved yield (e. g., improved yield under non-stress conditions or improved yield under biotic or abiotic stress); improved ability to use nitrogen, phosphate, or other nutrients; modified agronomic characteristics (e. g., delayed ripening; delayed senescence; earlier or later maturity; improved shade tolerance; improved resistance to root or stalk lodging; improved resistance to "green snap" of stems; modified photoperiod response); modified growth or reproductive characteristics (e. g., intentional dwarfing; intentional male sterility, useful, e. g., in improved hybridization procedures; improved vegetative growth rate; improved germination; improved male or female fertility); improved harvest, storage, or processing quality (e. g., improved resistance to pests during storage, improved resistance to breakage, improved appeal to consumers); or any combination of these traits.

In another embodiment, transgenic seed, or seed produced by the transgenic plant, has modified primary metabolite (e. g., fatty acid, oil, amino acid, protein, sugar, or carbohydrate) composition, a modified secondary metabolite composition, a modified trace element, carotenoid, or vitamin composition, an improved harvest, storage, or processing quality, or a combination of these. In another embodiment, it can be desirable to change levels of native components of the transgenic plant or seed of a transgenic plant, for example, to decrease levels of an allergenic protein or glycoprotein or of a toxic metabolite.

Generally, screening a population of transgenic plants each regenerated from a transgenic plant cell is performed to identify transgenic plant cells that develop into transgenic plants having the desired trait. The transgenic plants are assayed to detect an enhanced trait, e. g., enhanced water use efficiency, enhanced cold tolerance, increased yield, enhanced nitrogen use efficiency, enhanced seed protein, and enhanced seed oil. Screening methods include direct screening for the trait in a greenhouse or field trial or screening for a surrogate trait. Such analyses are directed to detecting changes in the chemical composition, biomass, physiological properties, or morphology of the plant. Changes in chemical compositions such as nutritional composition of grain are detected by analysis of the seed composition and content of protein, free amino acids, oil, free fatty acids, starch, tocopherols, or other nutrients. Changes in growth or biomass characteristics are detected by measuring plant height, stem diameter, internode length, root and shoot dry weights, and (for grain-producing plants such as maize, rice, or wheat) ear or seed head length and diameter. Changes in physiological properties are identified by evaluating responses to stress conditions, e. g., assays under imposed stress conditions such as water deficit, nitrogen or phosphate deficiency, cold or hot growing conditions, pathogen or insect attack, light deficiency, or increased plant density. Other selection properties include days to flowering, days to pollen shed, days to fruit maturation, fruit or tuber quality or amount produced, days to silking in maize, leaf extension rate, chlorophyll content, leaf temperature, stand, seedling vigor, internode length, plant height, leaf number, leaf area, tillering, brace roots, staying green, stalk lodging, root lodging, plant health, fertility, green snap, and pest resistance. In addition, phenotypic characteristics of harvested fruit, seeds, or tubers can be evaluated.

EXAMPLES

Example 1

This example illustrates non-limiting embodiments of coding DNA sequences useful as target genes for controlling insect species and for making compositions and plants of this invention, and identifies dsRNA trigger sequences useful for controlling insect species. Orthologues to genes previously demonstrated to be efficacious targets for RNAi-mediated mortality in western corn rootworm were identified from insect species that have not previously been reported to be susceptible to orally delivered RNA. These orthologous target genes and examples of dsRNA trigger sequences are provided in Table 1.

TABLE 1

| Target Gene SEQ ID NO. | Target Gene ID | Target Gene Source Species (common name) | Target Gene Annotation | Trigger ID | Trigger SEQ ID NO.* | Trigger size (bp) |
|---|---|---|---|---|---|---|

Figure 2:
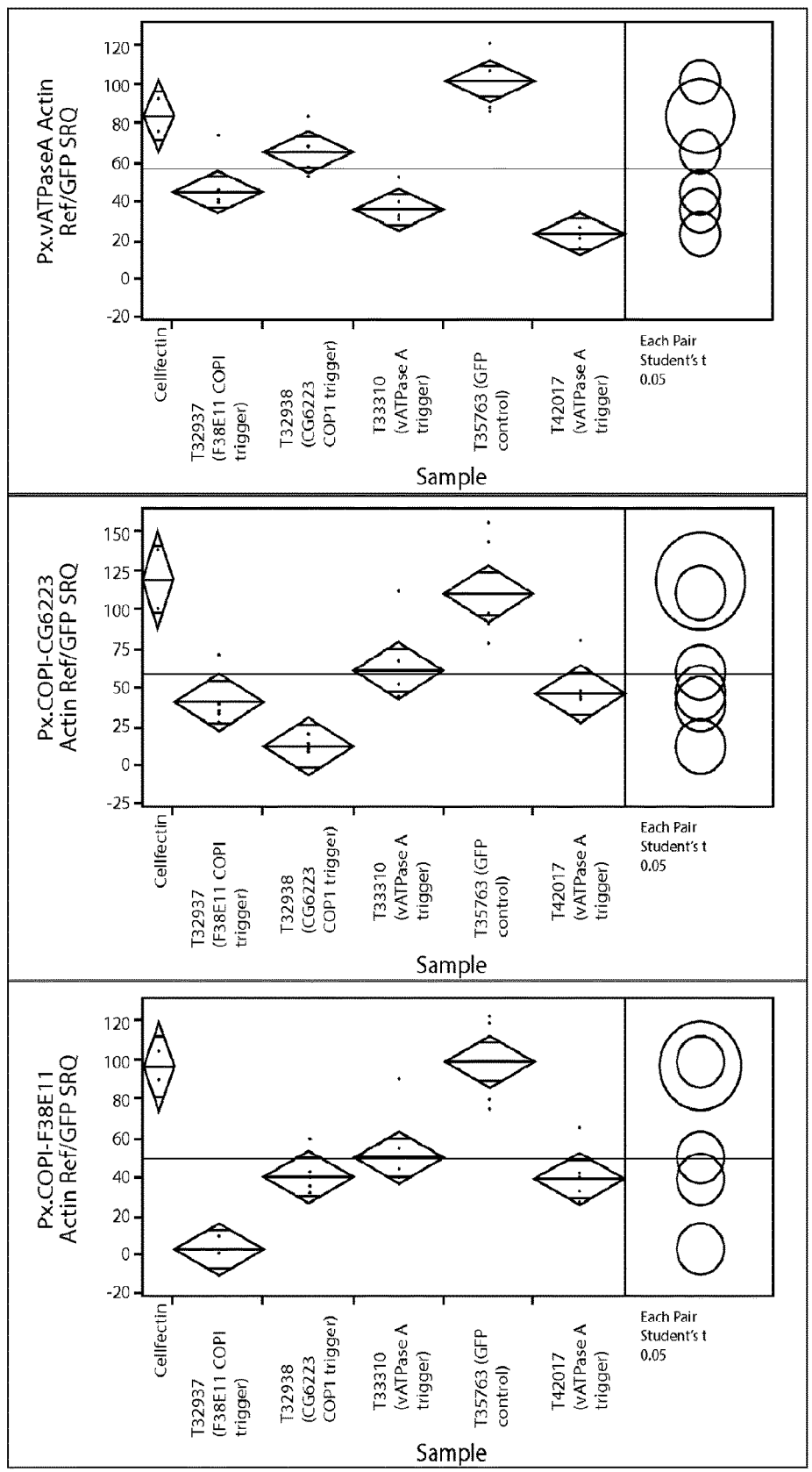
FIG. 2 depicts the results of the transfection experiments described in Example 2 for the dsRNA triggers (TOP PANEL) T42017 (SEQ ID NO:21, targetting V-ATPase subunit A), (TOP PANEL) T33310 (SEQ ID NO:29, targetting V-ATPase subunit A), (MIDDLE PANEL) T32938 (SEQ ID NO:28, targetting COPI coatomer beta subunit), and (BOTTOM PANEL) T32937 (SEQ ID NO:13, targetting COPI coatomer beta prime subunit) in *Plutella xylostella* (diamondback moth, DBM) cells.

| 1 | CG3762 | *Spodoptera frugiperda* (fall armyworm) | V-ATPase subunit A | T34640 | 17 | 300 |
| 2 | F38E11 | *Spodoptera frugiperda* (fall armyworm) | COPI coatomer beta prime subunit | T34644 | 19 | 301 |
| 3 | CG6223 | *Spodoptera frugiperda* (fall armyworm) | COPI coatomer beta subunit | T34642 | 18 | 301 |
| 4 | CG3762 | *Lygus hesperus* (western tarnished plant bug) | V-ATPase subunit A | T34617 | 15 | 300 |
| 5 | CG2746 | *Lygus hesperus* (western tarnished plant bug) | ribosomal protein L19 | T34616 | 14 | 298 |
| 6 | F38E11 | *Lygus hesperus* (western tarnished plant bug) | COPI coatomer beta prime subunit | T34622 | 16 | 300 |
| 7 | AT20865p | *Lygus hesperus* (western tarnished plant bug) | ubiquitin C | T42772 | 22 | 257 |
| 7 | AT20865p | *Lygus hesperus* (western tarnished plant bug) | ubiquitin C | T44045 | 26 | 302 |
| 8 | CG10370 | *Euschistus heros* (neotropical brown stink bug) | TAT binding protein | T43718 | 23 | 300 |
| 9 | AT20865p | *Euschistus heros* (neotropical brown stink bug) | ubiquitin C | T43720 | 24 | 300 |
| 9 | AT20865p | *Euschistus heros* (neotropical brown stink bug) | ubiquitin C | T44042 | 25 | 302 |
| 10 | CG3762 | *Plutella xylostella* (diamondback moth) | V-ATPase subunit A | T42014 | 20 | 302 |
| 10 | CG3762 | *Plutella xylostella* (diamondback moth) | V-ATPase subunit A | T42017 | 21 | 301 |
| 10 | CG3762 | *Plutella xylostella* (diamondback moth) | V-ATPase subunit A | T33310 | 29 | 300 |
| 11 | F38E11.5 | *Plutella xylostella* (diamondback moth) | COPI coatomer beta prime subunit | T32937 | 13 | 302 |
| 12 | CG6223 | *Plutella xylostella* (diamondback moth) | COPI coatomer beta subunit | T32938 | 28 | 302 |
| 43 | CG6223 | *Lygus hesperus* (western tarnished plant bug) | COPI coatomer beta subunit | T34619 | 45 | 301 |
| 44 | AT20865p | *Lygus hesperus* (western tarnished plant bug) | ubiquitin C variant (fragment) | T42768 | 46 | 255 |

*Trigger sequences are provided for the sense strand of the dsRNA trigger in 5' to 3' direction.

The dsRNA trigger sequences that are confirmed to be effective in suppressing a target gene in a sequence-specific manner are useful for identifying efficacious RNA delivery agents and formulations. The insecticidal activity of formulations containing the dsRNA triggers can be optimized by various techniques, such as modifying the chemical entities in the formulation or modifying the ratio of the chemical components in the formulation. Non-limiting examples of delivery agents and formulations are provided in Examples 6 and 8.

Example 2

This example illustrates non-limiting embodiments of dsRNA trigger sequences useful for suppressing or silencing a target gene in an insect cell or causing stunting or mortality in an insect, and methods for validating dsRNA trigger efficacy or for causing stunting or mortality in an insect. More specifically this example illustrates use of dsRNA triggers for sequence-specific reduction of target gene mRNA transcript level in insect cells.

Cultured *Spodoptera frugiperda* (fall armyworm, FAW) SF9 cells were incubated with the dsRNA triggers T34640 (SEQ ID NO:17, targetting V-ATPase A subunit), T34642 (SEQ ID NO:18, targetting COPI coatomer B (beta) subunit), or T34644 (SEQ ID NO:19, targetting COPI coatomer B' (beta prime) subunit), or with a control trigger T35763 (SEQ ID NO:27, a 300 bp dsRNA trigger targetting green fluorescent protein); see Table 1. The dsRNA triggers were formulated with the commercial transfection agent Cellfectin® II (Life Technologies, Inc., Grand Island, N.Y. 14072). FIG. 1 depicts the results of the transfection experiments, demonstrating target-gene-specific suppression (reduction of target gene mRNA levels measured by Quantigene assays) by the dsRNA triggers in the insect cells. The control dsRNA trigger T35763 had no effect on the targetted insect gene mRNA levels.

Similar experiments were carried out with *Plutella xylostella* (diamondback moth, DBM) cells. The results demonstrate a similar target-gene-specific cytotoxic response to the DBM triggers but not to a non-specific trigger targetting green fluorescent protein. Cultured *Plutella xylostella* (diamondback moth) PxE-PO#5A3 cells were incubated with the dsRNA triggers T42017 (SEQ ID NO:21, targetting V-ATPase subunit A), T33310 (SEQ ID NO:29, targetting V-ATPase subunit A), T32938 (SEQ ID NO:28, targetting COPI coatomer beta subunit), and T32937 (SEQ ID NO:13, targetting COPI coatomer beta prime subunit), or with a control trigger T35763 (SEQ ID NO:27, a 300 bp dsRNA trigger targetting green fluorescent protein); see Table 1. The dsRNA triggers were formulated with the commercial transfection agent Cellfectin® II (Life Technologies, Inc., Grand Island, N.Y. 14072). FIG. 2 depicts the results of the transfection experiments, demonstrating target-gene-specific suppression (reduction of target gene mRNA levels measured by Quantigene assays) by the dsRNA triggers in the insect cells. The control dsRNA trigger T35763 had no effect on the targetted insect gene mRNA levels. In this particular experiment, some reduction of mRNA levels was observed in all DBM-specific trigger treatments compared to cellfectin II or cellfectin II+T35763 (SEQ ID NO:27) treatments. Visual pathology was apparent for T32937 (SEQ ID NO:13, targetting COPI coatomer beta prime subunit) and T32938 (SEQ ID NO:28, targetting COPI coatomer beta subunit) treatments with some cell death, rounding, and dislodging occurring in transfected wells at 48 hours post-transfection. Treatments with T42017 (SEQ ID NO:21) and T33310 (SEQ ID NO:29) showed knockdown of the target gene, V-ATPase subunit A mRNA, but no visual pathology was apparent in cells transfected with those triggers.

Example 3

This example illustrates non-limiting embodiments of dsRNA trigger sequences useful for suppressing or silencing a target gene in an insect cell or causing stunting or mortality in an insect, and methods for validating dsRNA trigger efficacy or for causing stunting or mortality in an insect. More specifically this example illustrates oral delivery of dsRNA triggers for causing stunting or mortality in insects.

An assay using *Euschistus heros* (neotropical brown stink bug, NBSB) nymphs fed on an artificial diet was used for testing the efficacy of dsRNA triggers designed specifically to target *Euschistus heros* genes. Using this assay, a ~500 base pair dsRNA trigger, T33199, which targets the *E. heros* ubiquitin C gene, was observed to effect a dose-dependent stunting and mortality response in *E. heros* nymphs. A shorter (302 bp) dsRNA trigger, T44042 (SEQ ID NO:26) was designed, based on the sequence of T33199, for formulating for oral or topical delivery.

Example 4

This example illustrates non-limiting embodiments of dsRNA trigger sequences useful for suppressing or silencing a target gene in an insect cell or causing stunting or mortality in an insect, and methods for validating dsRNA trigger efficacy or for causing stunting or mortality in an insect. More specifically this example illustrates embodiments of dsRNA triggers for causing stunting or mortality in insects, and demonstrates systemic RNAi efficacy of these triggers.

Table 2 provides dsRNA triggers tested by microinjection delivery in *Lygus hesperus* (Western tarnished plant bug) nymphs. The non-*Lygus*-specific trigger T35763 (SEQ ID NO:27, a 300 bp dsRNA trigger targetting green fluorescent protein) was used as a control.

TABLE 2

| Trigger SEQ ID NO.* | Trigger ID | *Lygus hesperus* Target Gene | Amount injected per insect (micrograms) |
|---|---|---|---|
| 14 | T34616 | ribosomal protein rpL19 | 1-2 |
| 15 | T34617 | V-ATPase subunit A | 1-2 |
| 16 | T34622 | COPI coatomer B' (beta prime) subunit | 1-2 |
| 22 | T42772 | ubiquitin C | 1-2 |

Table 3 presents mortality results for dsRNA triggers, T34617 (SEQ ID NO:15, targetting *Lygus hesperus* V-ATPase subunit A), and T34622 (SEQ ID NO:16, targetting *Lygus hesperus* COPI coatomer beta prime subunit) tested by microinjection delivery in *Lygus hesperus* (Western tarnished plant bug) nymphs. Control nymphs were microinjected with T35763 (targetting green fluorescent protein) or with deionized water. Increased percent mortality by day was observed for *Lygus*-target-gene-specific treatment groups (T34617 and T34622) compared to negative control treatment groups over the 5-day observation period.

TABLE 3

| Trigger ID | Trigger SEQ ID NO: | *Lygus hesperus* Target gene | Percent mortality, shown by days after injection | | | | | | Total *Lygus hesperus* nymphs injected |
|---|---|---|---|---|---|---|---|---|---|
| | | | 0 | 1 | 2 | 3 | 4 | 5 | |
| T34617 | 15 | V-ATPase subunit A | 12 | 25 | 58 | 75 | 88 | 100 | 24 |
| T34622 | 16 | COPI coatomer beta prime subunit | 8 | 12 | 67 | 96 | 96 | 100 | 24 |
| T35763 | 27 | GFP | 12 | 12 | 29 | 50 | 58 | 67 | 24 |
| dH$_2$O | (none) | (none) | 0 | 5 | 20 | 45 | 55 | 75 | 20 |

Table 4 presents mortality results for dsRNA triggers, T34616 (SEQ ID NO:14, targetting *Lygus hesperus* ribosomal protein rpL19), T34622 (SEQ ID NO:16, targetting *Lygus hesperus* COPI coatomer beta prime subunit), and T42772 (SEQ ID NO:22, targetting *Lygus hesperus* ubiquitin C), tested by microinjection delivery in *Lygus hesperus* (Western tarnished plant bug) nymphs. Control nymphs were microinjected with T35763 (targetting green fluorescent protein). Increased percent mortality by day was observed for *Lygus*-target-gene-specific treatment groups (T34616, T34622, and T42772) compared to the negative control (T35763) treatment group over the 6-day observation period. Repeat activity of T34622 confirmed activity of this trigger observed in the earlier trial (Table 3).

TABLE 4

| Trigger ID | Trigger SEQ ID NO: | *Lygus hesperus* Target gene | Percent mortality, shown by days after injection | | | | | | | Total *Lygus hesperus* nymphs injected |
|---|---|---|---|---|---|---|---|---|---|---|
| | | | 0 | 1 | 2 | 3 | 4 | 5 | 6 | |
| T34616 | 14 | ribosomal protein rpL19 | 18 | 77 | 77 | 91 | 100 | 100 | 100 | 22 |
| T34622 | 16 | COPI coatomer beta prime subunit | 12 | 50 | 83 | 88 | 100 | 100 | 100 | 24 |
| T42772 | 22 | ubiquitin C | 17 | 61 | 100 | 100 | 100 | 100 | 100 | 23 |
| T35763 | 27 | GFP | 8 | 22 | 44 | 48 | 56 | 56 | 61 | 23 |

Example 5

This example discloses embodiments related to polynucleotide molecules having a nucleotide sequence containing specific modifications such as nucleotide substitutions. Embodiments of such modifications include modified dsRNA triggers that provide improved sequence discrimination between the intended target gene of the insect pest of interest, and genetic sequences of other, non-target species.

Table 5 identifies examples of matches between the sequence of a target gene provided in Table 1 and a sequence identified in a non-target organism (NTO), where the match is a segment of at least 19 contiguous nucleotides. Table 5 further provides examples of sequence modifications (e. g., nucleotide changes at a specified location in the original target gene sequence) to eliminate the sequence match to a non-target organism.

TABLE 5

| Target Gene SEQ ID NO: | Target Species | Non-Target Organism (NTO) species | Length (in nucleotides) of contiguous segment matching the NTO sequence | Nucleotide position of beginning of matching segment | Nucleotide position where change is made to eliminate match to NTO sequence | Nucleotide change made to eliminate match to NTO sequence |
|---|---|---|---|---|---|---|
| 1 | *Spodoptera frugiperda* | *Danaus plexippus* | 19 | 398 | 408 | G-A |
| | | *Danaus plexippus* | 23 | 562 | 575 | C-T |
| | | *Danaus plexippus* | 26 | 604 | 617 | A-T |
| | | *Danaus plexippus* | 20 | 631 | 642 | C-T |
| | | *Danaus plexippus* | 20 | 661 | 671 | A-T |
| | | *Danaus plexippus* | 28 | 695 | 710 | T-A |
| | | *Danaus plexippus* | 20 | 727 | 737 | T-A |
| | | *Danaus plexippus* | 20 | 793 | 802 | A-G |
| | | *Danaus plexippus* | 20 | 847 | 858 | C-T |
| | | *Apis mellifera* | 19 | 891 | 900 | T-A |
| | | *Homo sapiens* | 21 | 905 | 900 | T-A |
| | | *Danaus plexippus* | 19 | 968 | 977 | T-C |
| | | *Danaus plexippus* | 23 | 1024 | 1035 | G-A |
| | | *Danaus plexippus* | 48 | 1078 | 1092 | C-T |
| | | | | | 1110 | G-A |
| 2 | *Spodoptera frugiperda* | *Danaus plexippus* | 20 | 241 | 250 | T-C |
| | | *Danaus plexippus* | 26 | 274 | 289 | G-A |
| | | *Homo sapiens* | 19 | 516 | 526 | A-G |
| | | *Danaus plexippus* | 26 | 1615 | 1628 | A-G |
| | | *Danaus plexippus* | 20 | 1771 | 1780 | C-T |
| | | *Danaus plexippus* | 20 | 1810 | 1820 | T-C |
| | | *Apis mellifera* | 19 | 1870 | 1879 | G-A |
| | | *Homo sapiens* | 20 | 1933 | 1945 | G-A |
| | | *Apis mellifera* | 19 | 1934 | 1946 | C-T |
| | | *Homo sapiens* | 21 | 1935 | 1946 | C-T |
| | | *Apis mellifera* | 20 | 1936 | 1946 | C-T |
| | | *Homo sapiens* | 20 | 1936 | 1946 | C-T |
| | | *Homo sapiens* | 19 | 1936 | 1946 | C-T |
| | | *Homo sapiens* | 19 | 1937 | 1946 | C-T |
| | | *Homo sapiens* | 19 | 1939 | 1946 | C-T |
| | | *Homo sapiens* | 19 | 1942 | 1946 | C-T |
| | | *Apis mellifera* | 19 | 2681 | 2690 | T-C |
| 3 | *Spodoptera frugiperda* | *Danaus plexippus* | 19 | 62 | 72 | C-T |
| | | *Homo sapiens* | 19 | 503 | 512 | C-G |
| | | *Homo sapiens* | 19 | 544 | 553 | A-G |
| | | *Bombus impatiens* | 22 | 659 | 669 | G-A |
| | | *Bombus terrestris* | 22 | 659 | 669 | G-A |
| | | *Danaus plexippus* | 26 | 859 | 873 | C-T |
| | | *Danaus plexippus* | 19 | 925 | 934 | G-A |

TABLE 5-continued

| Target Gene SEQ ID NO: | Target Species | Non-Target Organism (NTO) species | Length (in nucleotides) of contiguous segment matching the NTO sequence | Nucleotide position of beginning of matching segment | Nucleotide position where change is made to eliminate match to NTO sequence | Nucleotide change made to eliminate match to NTO sequence |
|---|---|---|---|---|---|---|
| | | Homo sapiens | 19 | 927 | 934 | G-A |
| | | Homo sapiens | 19 | 934 | 945 | G-A |
| | | Danaus plexippus | 19 | 935 | 945 | G-A |
| | | Danaus plexippus | 20 | 936 | 945 | G-A |
| | | Danaus plexippus | 26 | 952 | 964 | G-A |
| | | Homo sapiens | 19 | 974 | 983 | T-A |
| | | Homo sapiens | 19 | 1461 | 1470 | G-T |
| | | Homo sapiens | 19 | 1712 | 1722 | G-A |
| | | Homo sapiens | 20 | 1713 | 1722 | G-A |
| | | Homo sapiens | 20 | 2223 | 2232 | G-A |
| | | Homo sapiens | 19 | 2242 | 2256 | G-A |
| | | Danaus plexippus | 20 | 2245 | 2256 | G-A |
| | | Danaus plexippus | 24 | 2307 | 2319 | G-C |
| | | Danaus plexippus | 20 | 2332 | 2340 | C-T |
| | | Danaus plexippus | 29 | 2503 | 2517 | C-T |
| | | Danaus plexippus | 41 | 2626 | 2633 | T-C |
| 4 | Lygus hesperus | Danaus plexippus | 20 | 323 | 333 | G-A |
| | | Bombus impatiens | 20 | 1010 | 1020 | T-A |
| | | Bombus terrestris | 20 | 1010 | 1020 | T-A |
| | | Danaus plexippus | 20 | 1400 | 1410 | G-A |
| | | Homo sapiens | 19 | 1603 | 1612 | C-T |
| | | Bombus impatiens | 26 | 1607 | 1622 | C-T |
| | | Bombus terrestris | 26 | 1607 | 1622 | C-T |
| | | Homo sapiens | 19 | 1968 | 1977 | C-T |
| | | Apis mellifera | 19 | 2001 | 2010 | C-G |
| | | Apis mellifera | 20 | 2041 | 2050 | A-T |
| 5 | Lygus hesperus | Homo sapiens | 22 | 9 | 19 | T-C |
| | | Homo sapiens | 20 | 11 | 20 | T-A |
| | | Homo sapiens | 20 | 211 | 220 | A-T |
| 6 | Lygus hesperus | Bombus terrestris | 19 | 37 | 47 | A-G |
| | | Danaus plexippus | 20 | 367 | 383 | G-A |
| | | Homo sapiens | 19 | 374 | 383 | G-A |
| | | Danaus plexippus | 20 | 637 | 647 | A-T |
| | | Danaus plexippus | 26 | 802 | 815 | A-T |
| | | Apis mellifera | 21 | 927 | 938 | A-T |
| | | Danaus plexippus | 19 | 1529 | 1538 | A-T |
| | | Homo sapiens | 19 | 2492 | 2501 | T-C |
| | | Homo sapiens | 19 | 2493 | 2501 | T-C |
| 10 | Plutella xylostella | Danaus plexippus | 20 | 1390 | 1399 | T-A |
| | | Danaus plexippus | 19 | 1427 | 1437 | C-T |
| | | Danaus plexippus | 23 | 1471 | 1482 | G-A |
| | | Danaus plexippus | 20 | 1543 | 1553 | T-C |
| | | Homo sapiens | 20 | 1645 | 1654 | G-A |
| | | Danaus plexippus | 35 | 1654 | 1671 | G-A |
| | | Danaus plexippus | 23 | 1726 | 1736 | C-T |
| | | Danaus plexippus | 35 | 1942 | 1959 | G-A |
| | | Danaus plexippus | 20 | 2005 | 2016 | C-T |
| | | Danaus plexippus | 20 | 2038 | 2048 | C-T |
| | | Danaus plexippus | 20 | 2181 | 2190 | G-A |
| 11 | Plutella xylostella | Homo sapiens | 19 | 235 | 244 | C-T |
| | | Danaus plexippus | 22 | 404 | 414 | A-G |
| | | Homo sapiens | 19 | 517 | 526 | T-A |
| | | Apis mellifera | 19 | 690 | 699 | T-C |
| | | Danaus plexippus | 20 | 1771 | 1780 | C-T |
| | | Danaus plexippus | 20 | 1891 | 1899 | C-T |
| | | Homo sapiens | 20 | 1900 | 1910 | A-T |
| | | Danaus plexippus | 23 | 1942 | 1953 | C-T |
| 12 | Plutella xylostella | Danaus plexippus | 21 | 184 | 194 | T-C |
| | | Danaus plexippus | 19 | 384 | 393 | G-A |
| | | Danaus plexippus | 20 | 613 | 622 | C-T |
| | | Danaus plexippus | 32 | 916 | 931 | A-T |
| | | Homo sapiens | 19 | 916 | 931 | A-T |
| | | Homo sapiens | 21 | 935 | 931 | A-T |
| | | Homo sapiens | 19 | 1066 | 1078 | C-T |
| | | Danaus plexippus | 19 | 1067 | 1078 | C-T |
| | | Danaus plexippus | 20 | 1068 | 1078 | C-T |
| | | Homo sapiens | 19 | 1207 | 1219 | T-C |
| | | Danaus plexippus | 19 | 1208 | 1219 | T-C |
| | | Danaus plexippus | 20 | 1209 | 1219 | T-C |
| | | Danaus plexippus | 19 | 1355 | 1365 | G-A |

TABLE 5-continued

| Target Gene SEQ ID NO: | Target Species | Non-Target Organism (NTO) species | Length (in nucleotides) of contiguous segment matching the NTO sequence | Nucleotide position of beginning of matching segment | Nucleotide position where change is made to eliminate match to NTO sequence | Nucleotide change made to eliminate match to NTO sequence |
|---|---|---|---|---|---|---|
| | | Homo sapiens | 19 | 1474 | 1483 | C-T |
| | | Homo sapiens | 20 | 1884 | 1894 | G-A |
| | | | | | 1895 | C-T |
| | | Homo sapiens | 19 | 2142 | 2151 | C-T |
| | | Bombus terrestris | 19 | 2203 | 2213 | G-A |
| | | Homo sapiens | 19 | 2391 | 2401 | G-A |
| | | Homo sapiens | 19 | 2808 | 2817 | A-G |
| | | Danaus plexippus | 21 | 3172 | 3182 | C-T |
| | | Danaus plexippus | 20 | 3236 | 3245 | C-T |
| | | Homo sapiens | 19 | 3249 | 3258 | A-G |
| | | Danaus plexippus | 21 | 3270 | 3280 | G-A |
| | | Homo sapiens | 19 | 3402 | 3411 | C-T |
| | | Danaus plexippus | 27 | 3550 | 3564 | C-T |

Table 6 identifies examples of matches between the sequence of a dsRNA trigger provided in Table 1 and a sequence identified in a non-target organism (NTO), where the match is a segment of at least 19 contiguous nucleotides. Table 6 provides examples of sequence modifications (e. g., nucleotide changes at a specified location in the original dsRNA trigger sequence) which eliminate a specific sequence match of at least 19 contiguous nucleotides to a non-target organism. Table 6 further provides non-limiting embodiments of a modified trigger sequence in which all of the nucleotide changes recited in Table 6 for a given original trigger sequence have been made to eliminate the all of the recited match(es) of at least 19 contiguous nucleotides to a non-target organism sequence. For example, the modified dsRNA trigger having SEQ ID NO:31 has one nucleotide change (A→U) at position 213, when compared to the original dsRNA trigger having SEQ ID NO:15; this single change eliminates matches of at least 19 contiguous nucleotides to two non-target organisms, Bombus impatiens and Bombus terrestris. In another example, the modified dsRNA trigger having SEQ ID NO:35 has four nucleotide changes (at positions 42, 79, 124, and 194), when compared to the original dsRNA trigger having SEQ ID NO:20; these changes eliminate four matches of at least 19 contiguous nucleotides to the NTO Danaus plexippus. In another example, the modified dsRNA trigger having SEQ ID NO:37 has four nucleotide changes (at positions 64, 72, 131, and 280), when compared to the original dsRNA trigger having SEQ ID NO:20; these changes eliminate four matches of at least 19 contiguous nucleotides to the NTOs Bombus impatiens, Bombus terrestris, Homo sapiens, and Danaus plexippus.

TABLE 6

| Original Trigger SEQ ID NO: | Non-Target Organism (NTO) species | Length (in contiguous nucleotides) of segment matching the NTO sequence | Nucleotide position of beginning of matching segment | Nucleotide position where change is made to eliminate match to NTO sequence | Nucleotide change made to eliminate match to NTO sequence | Modified trigger sequence SEQ ID NO: |
|---|---|---|---|---|---|---|
| 13 | Homo sapiens | 19 | 229 | 238 | C-U | 30 |
| 15 | Bombus impatiens | 20 | 202 | 213 | A-U | 31 |
| | Bombus terrestris | 20 | 202 | 213 | A-U | |
| 16 | Bombus terrestris | 19 | 22 | 32 | A-G | 32 |
| 17 | Danaus plexippus | 19 | 131 | 140 | A-U | 33 |
| 18 | Homo sapiens | 19 | 162 | 171 | G-A | 34 |
| 20 | Danaus plexippus | 20 | 33 | 42 | U-A | 35 |
| | Danaus plexippus | 19 | 70 | 79 | A-U | |
| | Danaus plexippus | 23 | 114 | 124 | G-A | |
| | Danaus plexippus | 20 | 186 | 196 | U-A | |
| 22 | Homo sapiens | 23 | 12 | 24 | U-C | 36 |
| | Homo sapiens | 26 | 12 | 24 | U-C | |
| | Homo sapiens | 20 | 15 | 26 | G-A | |
| | Homo sapiens | 23 | 15 | 26 | G-A | |
| | Danaus plexippus | 20 | 27 | 36 | G-A | |
| | Homo sapiens | 23 | 54 | 71 | C-U | |
| | Homo sapiens | 19 | 64 | 71 | C-U | |
| | Homo sapiens | 23 | 126 | 138 | G-A | |
| | Homo sapiens | 20 | 126 | 138 | G-A | |
| | Apis mellifera | 20 | 210 | 220 | A-G | |
| | Bombus terrestris | 20 | 210 | 220 | A-G | |

TABLE 6-continued

| Original Trigger SEQ ID NO: | Non-Target Organism (NTO) species | Length (in contiguous nucleotides) of segment matching the NTO sequence | Nucleotide position of beginning of matching segment | Nucleotide position where change is made to eliminate match to NTO sequence | Nucleotide change made to eliminate match to NTO sequence | Modified trigger sequence SEQ ID NO: |
|---|---|---|---|---|---|---|
| | *Danaus plexippus* | 20 | 216 | 220 | A-G | |
| | *Apis mellifera* | 20 | 225 | 220 | A-G | |
| | *Apis mellifera* | 29 | 228 | 220 | A-G | |
| | *Apis mellifera* | 23 | 234 | 243 | C-U | |
| 23 | *Bombus impatiens* | 29 | 53 | 64 | A-G | 37 |
| | *Bombus terrestris* | 20 | 62 | 72 | U-A | |
| | *Homo sapiens* | 19 | 122 | 131 | G-A | |
| | *Danaus plexippus* | 20 | 271 | 280 | A-G | |
| 24 | *Bombus impatiens* | 27 | 98 | 99 | G-C | 38 |
| | *Danaus plexippus* | 19 | 102 | 112 | U-A | |
| | *Bombus impatiens* | 20 | 164 | 176 | A-U | |
| | *Apis mellifera* | 20 | 167 | 176 | A-U | |
| | *Apis mellifera* | 29 | 167 | 176 | A-U | |
| | *Danaus plexippus* | 20 | 167 | 176 | A-U | |
| | *Apis mellifera* | 19 | 186 | 192 | U-C | |
| | *Bombus impatiens* | 26 | 188 | 196 | A-G | |
| | *Apis mellifera* | 26 | 200 | 204 | A-U | |
| | *Apis mellifera* | 20 | 203 | 213 | U-C | |
| | *Bombus impatiens* | 20 | 203 | 213 | U-C | |
| | *Bombus terrestris* | 20 | 203 | 213 | U-C | |
| | *Danaus plexippus* | 26 | 209 | 224 | G-U | |
| | *Apis mellifera* | 24 | 227 | 224 | G-U | |
| | *Apis mellifera* | 22 | 228 | 224 | G-U | |
| | *Bombus impatiens* | 19 | 228 | 224 | G-U | |
| | *Homo sapiens* | 20 | 231 | 242 | G-A | |
| | *Apis mellifera* | 23 | 251 | 264 | G-A | |
| | *Bombus impatiens* | 20 | 281 | 291 | A-U | |
| | *Bombus impatiens* | 23 | 47 | 63 | A-U | |
| | *Bombus impatiens* | 20 | 47 | 63 | A-U | |
| | *Bombus terrestris* | 20 | 50 | 63 | A-U | |
| | *Danaus plexippus* | 20 | 53 | 63 | A-U | |
| | *Bombus impatiens* | 39 | 86 | 99 | G-C | |
| | *Bombus impatiens* | 29 | 86 | 99 | G-C | |
| | *Bombus terrestris* | 39 | 86 | 99 | G-C | |
| | *Bombus impatiens* | 30 | 95 | 99 | G-C | |
| | *Apis mellifera* | 19 | 96 | 99 | G-C | |
| | *Apis mellifera* | 22 | 96 | 99 | G-C | |
| 25 | *Apis mellifera* | 23 | 53 | 66 | C-U | 39 |
| | *Apis mellifera* | 26 | 68 | 66 | C-U | |
| | *Bombus impatiens* | 26 | 68 | 66 | C-U | |
| | *Apis mellifera* | 26 | 71 | 84 | A-U | |
| | *Apis mellifera* | 23 | 71 | 84 | A-U | |
| | *Bombus impatiens* | 20 | 80 | 84 | A-U | |
| | *Apis mellifera* | 20 | 89 | 99 | A-U | |
| | *Bombus impatiens* | 23 | 155 | 168 | A-U | |
| | *Bombus impatiens* | 20 | 155 | 168 | A-U | |
| | *Bombus terrestris* | 20 | 158 | 168 | A-U | |
| | *Danaus plexippus* | 20 | 161 | 168 | A-U | |
| | *Bombus impatiens* | 39 | 194 | 206 | G-A | |
| | *Bombus impatiens* | 29 | 194 | 206 | G-A | |
| | *Bombus terrestris* | 39 | 194 | 206 | G-A | |
| | *Bombus impatiens* | 30 | 203 | 206 | G-A | |
| | *Apis mellifera* | 19 | 204 | 206 | G-A | |
| | *Apis mellifera* | 22 | 204 | 206 | G-A | |
| | *Bombus impatiens* | 27 | 206 | 221 | U-G | |
| | *Danaus plexippus* | 19 | 210 | 221 | U-G | |
| | *Bombus impatiens* | 20 | 272 | 285 | A-U | |
| | *Apis mellifera* | 20 | 275 | 285 | A-U | |
| | *Apis mellifera* | 28 | 275 | 285 | A-U | |
| | *Danaus plexippus* | 20 | 275 | 285 | A-U | |
| 26 | *Homo sapiens* | 19 | 62 | 77 | G-A | 40 |
| | *Danaus plexippus* | 20 | 68 | 77 | G-A | |
| | *Homo sapiens* | 20 | 68 | 77 | G-A | |
| | *Homo sapiens* | 20 | 98 | 113 | A-G | |
| | *Bombus terrestris* | 20 | 104 | 113 | A-G | |
| | *Danaus plexippus* | 20 | 155 | 167 | C-U | |
| | *Danaus plexippus* | 23 | 155 | 167 | C-U | |
| | *Homo sapiens* | 23 | 155 | 167 | C-U | |
| | *Danaus plexippus* | 23 | 197 | 211 | U-C | |
| | *Danaus plexippus* | 19 | 201 | 211 | U-C | |

TABLE 6-continued

| Original Trigger SEQ ID NO: | Non-Target Organism (NTO) species | Length (in contiguous nucleotides) of segment matching the NTO sequence | Nucleotide position of beginning of matching segment | Nucleotide position where change is made to eliminate match to NTO sequence | Nucleotide change made to eliminate match to NTO sequence | Modified trigger sequence SEQ ID NO: |
|---|---|---|---|---|---|---|
|  | Danaus plexippus | 23 | 221 | 231 | U-C |  |
|  | Homo sapiens | 30 | 271 | 285 | A-G |  |
|  | Homo sapiens | 21 | 271 | 285 | A-G |  |
| 27 | Homo sapiens | 19 | 75 | 84 | A-U | 41 |

TABLE 7-continued

Insect mortality (as percent of total insects in treatment),
dsRNA triggers tested at 500 ppm in presence of 5 mg/mL yeast tRNA

| Treatment | Trigger SEQ ID NO: | Total insects in treatment | Days since start of assay | | | | | |
|---|---|---|---|---|---|---|---|---|
| | | | 0 | 3 | 4 | 5 | 6 | 7 |
| T35763 GFP (control) | 27 | 45 | 0 | 16 | 31 | 38 | 60 | 69 |
| T34616 rpL19 | 14 | 58 | 0 | 31 | 50 | 72 | 86 | 97 |
| T34617 V-ATPase subunit A | 15 | 62 | 0 | 34 | 52 | 73 | 87 | 92 |
| T34619 COPI coatomer beta subunit | 45 | 56 | 0 | 36 | 43 | 68 | 71 | 89 |
| T34622 COPI coatomer beta prime subunit | 16 | 69 | 0 | 43 | 58 | 78 | 90 | 93 |
| T42772 ubiquitin C | 22 | 75 | 0 | 61 | 81 | 93 | 97 | 99 |

TABLE 8

Insect mortality (as percent of total insects in treatment),
dsRNA triggers tested at 500 ppm (without yeast tRNA)

| Treatment | Trigger SEQ ID NO: | Total insects in treatment | Days since start of assay | | | | | |
|---|---|---|---|---|---|---|---|---|
| | | | 0 | 3 | 4 | 5 | 6 | 7 |
| 15% sucrose | — | 65 | 0 | 26 | 42 | 63 | 71 | 78 |
| T35763 GFP (control) | 27 | 38 | 0 | 29 | 55 | 68 | 76 | 76 |
| T34616 rpL19 | 14 | 62 | 0 | 24 | 47 | 71 | 87 | 94 |
| T34617 V-ATPase subunit A | 15 | 71 | 0 | 35 | 68 | 83 | 89 | 92 |
| T34619 COPI coatomer beta subunit | 45 | 56 | 0 | 38 | 86 | 91 | 95 | 95 |
| T34622 COPI coatomer beta prime subunit | 16 | 64 | 0 | 62 | 95 | 100 | 100 | 100 |
| T42772 ubiquitin C | 22 | 30 | 0 | 63 | 80 | 90 | 93 | 100 |

TABLE 9A

*Lygus hesperus* mortality (as percent of total insects in treatment),
dsRNA triggers tested at 500 ppm in presence of 5 mg/mL yeast tRNA

| Treatment | Trigger SEQ ID NO: | Total insects in treatment | Days since start of assay | | | | | |
|---|---|---|---|---|---|---|---|---|
| | | | 0 | 3 | 4 | 5 | 6 | 7 |
| 15% sucrose | — | 28 | 0 | 36 | 50 | 57 | 64 | 64 |
| 15% sucrose + 5 mg/mL tRNA | — | 43 | 0 | 44 | 56 | 70 | 77 | 79 |
| T35763 GFP (control) | 27 | 32 | 0 | 50 | 66 | 78 | 88 | 91 |
| T34622 COPI coatomer beta prime subunit | 16 | 54 | 0 | 52 | 72 | 82 | 94 | 98 |
| T42772 ubiquitin C | 22 | 58 | 0 | 69 | 95 | 97 | 100 | 100 |
| T44045 ubiquitin C | 26 | 80 | 0 | 66 | 85 | 94 | 99 | 100 |

TABLE 9B

*Lygus lineolaris* mortality (as percent of total insects in treatment),
dsRNA triggers tested at 500 ppm in presence of 5 mg/mL yeast tRNA

| Treatment | Trigger SEQ ID NO: | Total insects in treatment | Days since start of assay | | | | | |
|---|---|---|---|---|---|---|---|---|
| | | | 0 | 3 | 4 | 5 | 6 | 7 |
| 15% sucrose + 5 mg/mL tRNA | — | 10 | 0 | 20 | 40 | 40 | 40 | 40 |
| T35763 GFP (control) | 27 | 16 | 0 | 19 | 44 | 50 | 56 | 69 |
| T42772 ubiquitin C | 22 | 20 | 0 | 30 | 45 | 60 | 75 | 95 |
| T44045 ubiquitin C | 26 | 21 | 0 | 29 | 43 | 67 | 86 | 90 |

TABLE 10

*Lygus hesperus* mortality (as percent of total insects in treatment),
dsRNA triggers tested at 1000 ppm

| Treatment | Trigger SEQ ID NO: | Replicate | Total insects in treatment | Days since start of assay | | | | |
|---|---|---|---|---|---|---|---|---|
| | | | | 0 | 3 | 4 | 5 | 6 | 7 |
| 15% sucrose | — | 1 | 29 | 0 | 45 | 45 | 48 | 48 | 52 |
| | | 2 | 30 | 0 | 23 | 33 | 57 | 67 | 70 |
| | | 3 | 30 | 0 | 21 | 28 | 34 | 41 | 41 |
| 15% sucrose - mortality, mean (sd*) | | | | 0 (0) | 30 (13) | 35 (9) | 46 (11) | 52 (13) | 54 (14) |
| T35763 GFP (control) | 27 | 1 | 30 | 0 | 20 | 30 | 53 | 53 | 53 |
| | | 2 | 30 | 0 | 13 | 17 | 53 | 63 | 67 |
| | | 3 | 30 | 0 | 30 | 40 | 50 | 57 | 60 |
| T35763 - mortality, mean (sd*) | | | | 0 (0) | 21 (8) | 29 (12) | 52 (2) | 58 (5) | 60 (7) |
| T44045 ubiquitin C | 26 | 1 | 30 | 0 | 37 | 53 | 63 | 77 | 87 |
| | | 2 | 29 | 0 | 24 | 38 | 59 | 76 | 86 |
| | | 3 | 30 | 0 | 43 | 47 | 57 | 70 | 73 |
| T44045 - mortality, mean (sd*) | | | | 0 (0) | 35 (10) | 46 (8) | 60 (3) | 74 (4) | 82 (8) |
| T42768 ubiquitin C | 46 | 1 | 29 | 0 | 17 | 55 | 90 | 97 | 97 |
| | | 2 | 30 | 0 | 50 | 60 | 80 | 83 | 87 |
| | | 3 | 30 | 0 | 40 | 60 | 70 | 77 | 80 |
| T42769 - mortality, mean (sd*) | | | | 0 (0) | 36 (17) | 58 (3) | 80 (10) | 86 (10) | 88 (8) |

*sd = standard deviation of the mean, given in percentage

Target gene suppression was assessed in *Lygus hesperus* by Quantigene analysis of three target genes (COPI coatomer beta prime subunit, V-ATPase subunit A, and COPI coatomer beta subunit). Sucrose feeding assays were carried out using the dsRNA triggers T34616 (SEQ ID NO:14), T34617 (SEQ ID NO:15), T34619 (SEQ ID NO:45), T34622 (SEQ ID NO:16), T42772 (SEQ ID NO:22), and T44045 (SEQ ID NO:26) tested at 500 or 100 ppm in 15% sucrose as described above. Immediately following the end of the 72-hour sucrose-feeding stage, the nymphs were individually frozen and subjected to Quantigene analysis. All values were normalized against the expression levels of two reference genes (EF1alpha and actin). The results (Tables 11A-C) demonstrated that each of the three tested target genes was specifically suppressed by the corresponding dsRNA trigger, coincident with observed increased mortality when compared to treatment with sucrose only or with the control GFP trigger T35763 (SEQ ID NO:27). The observed target gene suppression (reduction in target gene expression) was significant (p=0.05) compared to sucrose controls for five of six trigger experiments; in the sixth trigger experiment (T34622 at 1000 ppm, see Table 11A) visual suppression was observed just below the significance level. These results support the conclusion that the mortality observed in 15% sucrose feeding assays is mediated by RNAi.

TABLE 11A

Target gene: *L. hesperus* COPI coatomer beta prime subunit (F38E11), SEQ ID NO: 6

| Trigger concentration | Treatment | Target gene | % change from control | Significant @ p = 0.05 from control? |
|---|---|---|---|---|
| n/a | sucrose only | n/a | n/a | n/a |
| 1000 ppm | T34617 (SEQ ID NO: 15) | V-ATPase subunit A | −4% | no |
| 1000 ppm | T34619 (SEQ ID NO: 45) | COPI coatomer beta subunit | 33% | no |
| 1000 ppm | T34622 (SEQ ID NO: 16) | COPI coatomer beta prime subunit | −34% | no |
| 1000 ppm | T35763 (SEQ ID NO: 27) | GFP | 4% | no |
| 1000 ppm | T44045 (SEQ ID NO: 26) | ubiquitin C | 19% | no |
| n/a | sucrose only | n/a | n/a | n/a |
| 500 ppm | T34617 (SEQ ID NO: 15) | V-ATPase subunit A | −15% | no |
| 500 ppm | T34619 (SEQ ID NO: 45) | COPI coatomer beta subunit | −31% | no |
| 500 ppm | T34622 (SEQ ID NO: 16) | COPI coatomer beta prime subunit | −71% | yes |
| 500 ppm | T35763 (SEQ ID NO: 27) | GFP | −24% | no |
| n/a | untreated (artificial diet fed) | n/a | 3% | no |

TABLE 11B

Target gene: *L. hesperus* V-ATPase A subunit (CG3762), SEQ ID NO: 4

| Trigger concentration | Treatment | Target gene | % change from control | Significant @ p = 0.05 from control? |
|---|---|---|---|---|
| n/a | sucrose only | n/a | n/a | n/a |
| 1000 ppm | T34617 (SEQ ID NO: 15) | V-ATPase subunit A | −77% | yes |
| 1000 ppm | T34619 (SEQ ID NO: 45) | COPI coatomer beta subunit | −21% | no |
| 1000 ppm | T34622 (SEQ ID NO: 16) | COPI coatomer beta prime subunit | −23% | no |
| 1000 ppm | T35763 (SEQ ID NO: 27) | GFP | −23% | no |
| 1000 ppm | T44045 (SEQ ID NO: 26) | ubiquitin C | −25% | no |
| n/a | sucrose only | n/a | n/a | n/a |
| 500 ppm | T34617 (SEQ ID NO: 15) | V-ATPase subunit A | −63% | yes |
| 500 ppm | T34619 (SEQ ID NO: 45) | COPI coatomer beta subunit | −25% | no |
| 500 ppm | T34622 (SEQ ID NO: 16) | COPI coatomer beta prime subunit | 7% | no |
| 500 ppm | T35763 (SEQ ID NO: 27) | GFP | −35% | no |
| n/a | untreated (artificial diet fed) | n/a | 20% | no |

TABLE 11C

Target gene: *L. hesperus* COPI coatomer beta subunit (CG6223), SEQ ID NO: 43

| Trigger concentration | Treatment | Target gene | % change from control | Significant @ p = 0.05 from control? |
|---|---|---|---|---|
| n/a | sucrose only | n/a | n/a | n/a |
| 1000 ppm | T34617 (SEQ ID NO: 15) | V-ATPase subunit A | 6% | no |
| 1000 ppm | T34619 (SEQ ID NO: 45) | COPI coatomer beta subunit | −49% | yes |

TABLE 11C-continued

Target gene: *L. hesperus* COPI coatomer beta subunit (CG6223), SEQ ID NO: 43

| Trigger concentration | Treatment | Target gene | % change from control | Significant @ p = 0.05 from control? |
|---|---|---|---|---|
| 1000 ppm | T34622 (SEQ ID NO: 16) | COPI coatomer beta prime subunit | 28% | no |
| 1000 ppm | T35763 (SEQ ID NO: 27) | GFP | 18% | no |
| 1000 ppm | T44045 (SEQ ID NO: 26) | ubiquitin C | 21% | no |
| n/a | sucrose only | n/a | n/a | n/a |
| 500 ppm | T34617 (SEQ ID NO: 15) | V-ATPase subunit A | −22% | no |
| 500 ppm | T34619 (SEQ ID NO: 45) | COPI coatomer beta subunit | −54% | yes |
| 500 ppm | T34622 (SEQ ID NO: 16) | COPI coatomer beta prime subunit | −21% | no |
| 500 ppm | T35763 (SEQ ID NO: 27) | GFP | −34% | no |
| n/a | untreated (artificial diet fed) | n/a | 18% | no | n/a = not applicable

Example 7

The polynucleotides of this invention are generally designed to modulate expression by inducing regulation or suppression of an insect target gene and are designed to have a nucleotide sequence essentially identical or essentially complementary to the nucleotide sequence an insect target gene or cDNA (e. g., SEQ ID NOs:1-12 and 43-44) or to the sequence of RNA transcribed from an insect target gene, which can be coding sequence or non-coding sequence. These effective polynucleotide molecules that modulate expression are referred to herein as a "trigger", or "triggers". This example describes non-limiting techniques useful in the design and selection of polynucleotides as "triggers" to modulate expression of an insect target gene.

Selection of Polynucleotide Triggers by "Tiling"

Polynucleotides of use in the invention need not be of the full length of a target gene, and in many embodiments are of much shorter length in comparison to the target gene. An example of a technique that is useful for selecting effective triggers is "tiling", or evaluation of polynucleotides corresponding to adjacent or partially overlapping segments of a target gene.

Effective polynucleotide "triggers" can be identified by "tiling" gene targets in selected length fragments, e. g., fragments of 200-300 nucleotides in length, with partially overlapping regions, e. g., of about 25 nucleotides, along the length of the target gene. To suppress a single gene, trigger sequences are designed to correspond to (have a nucleotide identity or complementarity with) regions that are unique to the target gene; the selected region of the target gene can include coding sequence or non-coding sequence (e. g., promoter regions, 3' untranslated regions, introns and the like) or a combination of both.

Where it is of interest to design a target effective in suppressing multiple target genes, the multiple target gene sequences are aligned and polynucleotide triggers designed to correspond to regions with high sequence homology in common among the multiple targets. Conversely, where it is of interest to design a target effective in selectively suppressing one among multiple target sequences, the multiple target gene sequences are aligned and polynucleotide triggers designed to correspond to regions with no or low sequence homology in common among the multiple targets.

In a non-limiting example, anti-sense single-stranded RNA triggers are designed for each of the target genes listed in Table 1 as follows. Multiple anti-sense single-stranded RNA triggers, each of 200-300 nucleotides in length and with a sequence corresponding to (i. e., for anti-sense triggers, complementary to) a fragment of a target gene having a sequence selected from SEQ ID NOs:1-12 and 43-44 are designed so that each trigger's sequence overlaps about 25 nucleotides of the next adjacent trigger's sequence, in such a way that the multiple triggers in combination cover the full length of the target gene. (Sense triggers are designed in an analogous fashion, where the trigger sequence is identical to a fragment of the target gene. Similarly, double-stranded triggers can be designed by providing pairs of sense and anti-sense triggers, each pair of triggers overlapping the next adjacent pair of triggers.)

The polynucleotide triggers are tested by any convenient means for efficacy in silencing the insect target gene. Examples of a suitable test include the bioassays described herein in the working Examples. Another test involves the topical application of the polynucleotide triggers either directly to individual insects or to the surface of a plant to be protected from an insect infestation. One desired result of treatment with a polynucleotide of this invention is prevention or control of an insect infestation, e. g., by inducing in an insect a physiological or behavioural change such as, but not limited to, growth stunting, increased mortality, decrease in reproductive capacity, decrease in or cessation of feeding behavior or movement, or decrease in or cessation of metamorphosis stage development. Another desired result of treatment with a polynucleotide of this invention is provision of a plant that exhibits improved resistance to an insect infestation.

The tiling procedure can be repeated, if desired. A polynucleotide trigger found to provide desired activity can itself be subjected to a tiling procedure. For example, multiple overlapping anti-sense single-stranded RNA triggers are designed, each of 50-60 nucleotides in length and with a sequence corresponding to (i. e., for anti-sense triggers, complementary to) the fragment of a target gene having a sequence selected from SEQ ID NOs:1-12 and 43-44 for which a single polynucleotide trigger of 300 nucleotides was found to be effective. Additional rounds of tiling analysis can be carried out, where triggers as short as 18 or 19 nucleotides are tested.

Effective polynucleotide triggers of any size can be used, alone or in combination, in the various methods of this invention. In some embodiments, a single polynucleotide trigger is used to make a composition of this invention (e. g., a composition for topical application, or a recombinant DNA construct useful for making a transgenic plant). In other embodiments, a mixture or pool of different polynucleotide triggers is used; in such cases the polynucleotide triggers can be for a single target gene or for multiple target genes. In some embodiments, a polynucleotide trigger is designed to target different regions of the target gene, e. g., a trigger can include multiple segments that correspond to different exon regions of the target gene, and "spacer" nucleotides which do not correspond to a target gene can optionally be used in between or adjacent to the segments.

Thermodynamic Considerations in Selecting Polynucleotide Triggers

Polynucleotide triggers can be designed or their sequence optimised using thermodynamic considerations. For example, polynucleotide triggers can be selected based on the thermodynamics controlling hybridization between one nucleic acid strand (e. g., a polynucleotide trigger or an individual siRNA) and another (e. g., a target gene transcript)

Methods and algorithms to predict nucleotide sequences that are likely to be effective at RNAi-mediated silencing of a target gene are known in the art. Non-limiting examples of such methods and algorithms include "i-score", described by Ichihara et al. (2007) *Nucleic Acids Res.*, 35(18): 123e; "Oligowalk", publicly available at rna.urmc.rochester.edu/servers/oligowalk and described by Lu et al. (2008) *Nucleic Acids Res.*, 36:W104-108; and "Reynolds score", described by Khovorova et al. (2004) *Nature Biotechnol.*, 22:326-330.

Permitted Mismatches

By "essentially identical" or "essentially complementary" is meant that the trigger polynucleotide (or at least one strand of a double-stranded polynucleotide) has sufficient identity or complementarity to the target gene or to the RNA transcribed from a target gene (e. g., the transcript) to suppress expression of a target gene (e. g., to effect a reduction in levels or activity of the target gene transcript and/or encoded protein). Polynucleotides of this invention need not have 100 percent identity or complementarity to a target gene or to the RNA transcribed from a target gene to suppress expression of the target gene (e. g., to effect a reduction in levels or activity of the target gene transcript or encoded protein, or to provide control of an insect species). In some embodiments, the polynucleotide or a portion thereof is designed to be essentially identical to, or essentially complementary to, a sequence of at least 18 or 19 contiguous nucleotides in either the target gene or the RNA transcribed from the target gene. In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene. In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

Polynucleotides containing mismatches to the target gene or transcript can be used in certain embodiments of the compositions and methods of this invention. In some embodiments, the polynucleotide includes at least 18 or at least 19 contiguous nucleotides that are essentially identical or essentially complementary to a segment of equivalent length in the target gene or target gene's transcript. In certain embodiments, a polynucleotide of 19 contiguous nucleotides that is essentially identical or essentially complementary to a segment of equivalent length in the target gene or target gene's transcript can have 1 or 2 mismatches to the target gene or transcript (i. e., 1 or 2 mismatches between the polynucleotide's 19 contiguous nucleotides and the segment of equivalent length in the target gene or target gene's transcript). In certain embodiments, a polynucleotide of 20 or more nucleotides that contains a contiguous 19 nucleotide span of identity or complementarity to a segment of equivalent length in the target gene or target gene's transcript can have 1 or 2 mismatches to the target gene or transcript. In certain embodiments, a polynucleotide of 21 continuous nucleotides that is essentially identical or essentially complementary to a segment of equivalent length in the target gene or target gene's transcript can have 1, 2, or 3 mismatches to the target gene or transcript. In certain embodiments, a polynucleotide of 22 or more nucleotides that contains a contiguous 21 nucleotide span of identity or complementarity to a segment of equivalent length in the target gene or target gene's transcript can have 1, 2, or 3 mismatches to the target gene or transcript.

In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. (2005) *Nucleic Acids Res.*, 33:1671-1677. In some embodiments, mismatches in 19 base-pair overlap regions are located at the low tolerance positions 5, 7, 8 or 11 (from the 5' end of a 19-nucleotide target), at medium tolerance positions 3, 4, and 12-17 (from the 5' end of a 19-nucleotide target), and/or at the high tolerance positions at either end of the region of complementarity, i. e., positions 1, 2, 18, and 19 (from the 5' end of a 19-nucleotide target) as described by Du et al. (2005) *Nucleic Acids Res.*, 33:1671-1677. Tolerated mismatches can be empirically determined in routine assays such as those described herein in the working Examples.

In some embodiments, the polynucleotides include additional nucleotides for reasons of stability or for convenience in cloning or synthesis. In one embodiment, the polynucleotide is a dsRNA including an RNA strand with a segment of at least 21 contiguous nucleotides of a sequence selected from the group consisting of SEQ ID NOs:13-26, 28-29, 30-42, 45, and 46 and further including an additional 5' G or an additional 3' C or both, adjacent to the segment. In another embodiment, the polynucleotide is a double-stranded RNA including additional nucleotides to form an overhang, for example, a dsRNA including 2 deoxyribonucleotides to form a 3' overhang.

Embedding Active Triggers in Neutral Sequence

In an embodiment, a bioactive trigger (i. e., a polynucleotide with a sequence corresponding to the target gene and which is responsible for an observed suppression of the target gene) is embedded in "neutral" sequence, i. e., inserted into additional nucleotides that have no sequence identity or complementarity to the target gene. Neutral sequence can be desirable, e. g., to increase the overall length of a polynucleotide. For example, it can be desirable for a polynucleotide to be of a particular size for reasons of stability, cost-effectiveness in manufacturing, or biological activity.

It has been reported that in another coleopteran species, *Diabrotica virgifera*, dsRNAs greater than or equal to approximately 60 base-pairs (bp) are required for biological activity in artificial diet bioassays; see Bolognesi et al. (2012) PLoS ONE 7(10): e47534. doi:10.1371/journal.pone.0047534. Thus, in one embodiment, a 21-base-pair dsRNA trigger corresponding to a target gene in Table 1 and found to provide control of an insect infestation is embedded in neutral sequence of an additional 39 base pairs, thus forming a polynucleotide of about 60 base pairs. In another embodiment, a single 21-base-pair trigger is found to be efficacious when embedded in larger sections of neutral sequence, e. g., where the total polynucleotide length is from about 60 to about 300 base pairs. In another embodiment, at least one segment of at least 21 contiguous nucleotides of a sequence selected from the group consisting of SEQ ID NOs:13-26, 28-29, 30-42, 45, and 46 is embedded in larger sections of neutral sequence to provide an efficacious trigger. In another embodiment, segments from multiple sequences selected from the group consisting of SEQ ID NOs:13-26, 28-29, 30-42, 45, and 46 are embedded in larger sections of neutral sequence to provide an efficacious trigger.

It is anticipated that the combination of certain recombinant RNAs of this invention (e. g., the dsRNA triggers having a sequence selected from the group consisting of SEQ ID NOs:13-26, 28-29, 30-42, 45, and 46, or active fragments of these triggers) with one or more non-polynucleotide pesticidal agents will result in a synergetic improvement in prevention or control of insect infestations, when compared to the effect obtained with the recombinant RNA alone or the non-polynucleotide pesticidal agent alone. Routine insect bioassays such as the bioassays described herein in the working Examples are useful for defining dose-responses for larval mortality or growth inhibition using combinations of the polynucleotides of this invention and one or more non-polynucleotide pesticidal agents (e. g., a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein). One of skill in the art can test combinations of polynucleotides and non-polynucleotide pesticidal agents in routine bioassays to identify combinations of bioactives that are synergistic and desirable for use in protecting plants from insect infestations.

Example 8

This example illustrates non-limiting embodiments of the use of polynucleotides of this invention in topically applied compositions for preventing or controlling insect infestations.

Compositions containing one or more polynucleotides of this invention are useful as topical treatments of plants, animals, or environments wherein prevention or control of a *Leptinotarsa* species infestation is desired. In embodiments, a polynucleotide trigger for a target gene with a sequence selected from SEQ ID NOs:1-12 and 43-44, i. e., the target genes identified in Table 1, as described in the preceding examples, is included in an effective amount in a composition designed to be provided directly (e. g., by contact or ingestion) to an insect species, or a plant or environment wherein prevention or control of infestation by that insect is desired. In embodiments, a polynucleotide trigger for a target gene with a sequence selected from SEQ ID NOs:13-26, 28-29, 30-42, 45, and 46 is included in an effective amount in such compositions. In embodiments, a dsRNA trigger with a strand having a sequence selected from the group consisting of SEQ ID NOs:13-26, 28-29, 30-42, 45, and 46, or active fragments of these triggers, is included in an effective amount in such compositions. Such compositions are formulated and manufactured according to the art and can be in any convenient form, e. g., a solution or mixture of solutions, an emulsion, a suspension, a dispersible powder, a solid or liquid bait, a seed coating, or a soil drench. Embodiments of such compositions include those where the polynucleotide of this invention is provided in a living or dead microorganism such as a bacterium or fungal or yeast cell, or provided as a microbial fermentation product, or provided in a living or dead plant cell, or provided as a synthetic recombinant polynucleotide. In an embodiment the composition includes a non-pathogenic strain of a microorganism that contains a polynucleotide of this invention; ingestion or intake of the microorganism results in stunting or mortality of the insect pest; non-limiting examples of suitable microorganisms include *E. coli*, *B. thuringiensis*, *Pseudomonas* sp., *Photorhabdus* sp., *Xenorhabdus* sp., *Serratia entomophila* and related *Serratia* sp., *B. sphaericus*, *B. cereus*, *B. laterosporus*, *B. popilliae*, *Clostridium bifermentans* and other *Clostridium* species, or other spore-forming gram-positive bacteria. In an embodiment, the composition includes a plant virus vector including a polynucleotide of this invention; feeding by an insect on a plant treated with the plant virus vector results in stunting or mortality of the insect. In an embodiment, the composition includes a baculovirus vector including a polynucleotide of this invention; ingestion or intake of the vector results in stunting or mortality of the insect. In an embodiment, a polynucleotide of this invention is encapsulated in a synthetic matrix such as a polymer or attached to particulates and topically applied to the surface of a plant; feeding by an insect on the topically treated plant results in stunting or mortality of the insect. In an embodiment, a polynucleotide of this invention is provided in the form of a plant cell (e. g., a transgenic plant cell of this invention) expressing the polynucleotide; ingestion of the plant cell or contents of the plant cell by an insect results in stunting or mortality of the insect.

Embodiments of the compositions optionally include the appropriate stickers and wetters required for efficient foliar coverage as well as UV protectants to protect polynucleotides such as dsRNAs from UV damage. Such additives are commonly used in the bioinsecticide industry and are known to those skilled in the art. Compositions for soil application can include granular formulations that serve as bait for insect larvae. Embodiments include a carrier agent, a surfactant, an organosilicone, a polynucleotide herbicidal molecule, a non-polynucleotide herbicidal molecule, a non-polynucleotide pesticide, a safener, an insect attractant, and an insect growth regulator. In embodiments, the composition further includes at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

Such compositions are applied in any convenient manner, e. g., by spraying or dusting the insect directly, or spraying or dusting a plant or environment wherein prevention or control of infestation by that insect is desired, or by applying a coating to a surface of a plant, or by applying a coating to a seed (or seed potato) in preparation for the seed's planting, or by applying a soil drench around roots of a plant for which prevention or control of infestation by that insect is desired.

An effective amount of a polynucleotide of this invention is an amount sufficient to provide control of the insect, or to prevent infestation by the insect; determination of effective amounts of a polynucleotide of this invention are made using routine assays such as those described in the working Examples herein. While there is no upper limit on the concentrations and dosages of a polynucleotide of this invention that can be useful in the methods and compositions provided herein, lower effective concentrations and dosages will generally be sought for efficiency and economy. Non-limiting embodiments of effective amounts of a polynucleotide include a range from about 10 nanograms per milliliter to about 100 micrograms per milliliter of a polynucleotide in a liquid form sprayed on a plant, or from about 10 milligrams per acre to about 100 grams per acre of polynucleotide applied to a field of plants, or from about 0.001 to about 0.1 microgram per milliliter of polynucleotide in an artificial diet for feeding the insect. Where compositions of this invention are topically applied to a plant, the concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotides of this invention is about 1 nanomole (nmol) of polynucleotides per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide of this invention are applied. In certain embodiments, about 0.5 nmol to about 2 nmol of a dsRNA of this invention is applied. In certain embodiments, a composition containing about 0.5 to about 2.0 milligrams per milliliter, or about 0.14 milligrams per milliliter of a dsRNA or an ssDNA (21-mer) of this invention is applied. In certain embodiments, a composition of about 0.5 to about 1.5 milligrams per milliliter of a dsRNA polynucleotide of this invention of about 50 to about 200 or more nucleotides is applied. In certain embodiments, about 1 nmol to about 5 nmol of a dsRNA of this invention is applied to a plant. In certain embodiments, the polynucleotide composition as topically applied to the plant contains at least one polynucleotide of this invention at a concentration of about 0.01 to about 10 milligrams per milliliter, or about 0.05 to about 2 milligrams per milliliter, or about 0.1 to about 2 milligrams per milliliter. Very large plants, trees, or vines can require correspondingly larger amounts of polynucleotides. When using long dsRNA molecules of this invention that can be processed into multiple oligonucleotides (e. g., multiple triggers encoded by a single recombinant DNA molecule of this invention), lower concentrations can be used. Non-limiting examples of effective polynucleotide treatment regimes include a treatment of between about 0.1 to about 1 nmol of polynucleotide molecule per plant, or between about 1 nmol to about 10 nmol of polynucleotide molecule per plant, or between about 10 nmol to about 100 nmol of polynucleotide molecule per plant.

Embodiments of compositions of this invention include a "transfer agent", i. e., an agent that, when combined with a composition including a polynucleotide of this invention that is topically applied to the surface of an organism, enables the polynucleotide to enter the cells of that organism. Such transfer agents can be incorporated as part of the composition including a polynucleotide of this invention, or can be applied prior to, contemporaneously with, or following application of the composition including a polynucleotide of this invention. In embodiments, a transfer agent is an agent that improves the uptake of a polynucleotide of this invention by an insect. In embodiments, a transfer agent is an agent that conditions the surface of plant tissue, e. g., seeds, leaves, stems, roots, flowers, or fruits, to permeation by a polynucleotide of this invention into plant cells. In embodiments, the transfer agent enables a pathway for a polynucleotide of this invention through cuticle wax barriers, stomata, and/or cell wall or membrane barriers into plant cells.

Suitable transfer agents include agents that increase permeability of the exterior of the organism or that increase permeability of cells of the organism to polynucleotides of this invention. Suitable transfer agents include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. In embodiments, application of a composition of this invention and a transfer agent optionally includes an incubation step, a neutralization step (e. g., to neutralize an acid, base, or oxidizing agent, or to inactivate an enzyme), a rinsing step, or combinations thereof. Suitable transfer agents can be in the form of an emulsion, a reverse emulsion, a liposome, or other micellar-like composition, or can cause the polynucleotide composition to take the form of an emulsion, a reverse emulsion, a liposome, or other micellar-like composition. Embodiments of transfer agents include counter-ions or other molecules that are known to associate with nucleic acid molecules, e. g., inorganic ammonium ions, alkyl ammonium ions, lithium ions, polyamines such as spermine, spermidine, or putrescine, and other cations. Embodiments of transfer agents include organic solvents such as DMSO, DMF, pyridine, N-pyrrolidine, hexamethylphosphoramide, acetonitrile, dioxane, polypropylene glycol, or other solvents miscible with water or that dissolve phosphonucleotides in non-aqueous systems (such as is used in synthetic reactions). Embodiments of transfer agents include naturally derived or synthetic oils with or without surfactants or emulsifiers, e. g., plant-sourced oils, crop oils (such as those listed in the $9^{th}$ Compendium of Herbicide Adjuvants, publicly available on-line at herbicide.adjuvants-.com), paraffinic oils, polyol fatty acid esters, or oils with short-chain molecules modified with amides or polyamines such as polyethyleneimine or N-pyrrolidine.

Embodiments of transfer agents include organosilicone preparations. For example, a suitable transfer agent is an organosilicone preparation that is commercially available as SILWET L-77® brand surfactant having CAS Number 27306-78-1 and EPA Number: CAL.REG.NO. 5905-50073-AA, and currently available from Momentive Performance Materials, Albany, N.Y. In embodiments where a SILWET L-77® brand surfactant organosilicone preparation is used as transfer agent in the form of a spray treatment (applied prior to, contemporaneously with, or following application of the composition including a polynucleotide of this invention) of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of a polynucleotide of this invention into plant cells from a topical application on the surface. One embodiment includes a composition that comprises a polynucleotide of this invention and a transfer agent including an organosilicone preparation such as Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent). One embodiment includes a composition that comprises a polynucleotide of this invention and a transfer agent including SILWET L-77® brand surfactant in the range of about 0.3 to about 1 percent by weight (wt percent) or about 0.5 to about 1%, by weight (wt percent).

Organosilicone compounds useful as transfer agents for use in this invention include, but are not limited to, compounds that include: (a) a trisiloxane head group that is covalently linked to, (b) an alkyl linker including, but not limited to, an n-propyl linker, that is covalently linked to, (c) a polyglycol chain, that is covalently linked to, (d) a terminal group. Trisiloxane head groups of such organosilicone compounds include, but are not limited to, heptamethyltrisiloxane. Alkyl linkers can include, but are not limited to, an n-propyl linker. Polyglycol chains include, but are not limited to, polyethylene glycol or polypropylene glycol. Polyglycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Organosilicone compounds useful as transfer agents for use in this invention include, but are not limited to, trisiloxane ethoxylate surfactants or polyalkylene oxide modified heptamethyl trisiloxane. An example of a transfer agent for use in this invention is Compound I:

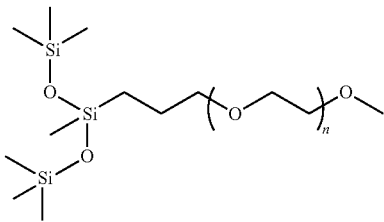

(Compound I: polyalkyleneoxide heptamethyltrisiloxane, average n = 7.5).

Organosilicone compounds useful as transfer agents for use in this invention are used, e. g., as freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent).

Embodiments of transfer agents include one or more salts such as ammonium chloride, tetrabutylphosphonium bromide, and ammonium sulfate, provided in or used with a composition including a polynucleotide of this invention. In embodiments, ammonium chloride, tetrabutylphosphonium bromide, and/or ammonium sulfate are used at a concentration of about 0.5% to about 5% (w/v), or about 1% to about 3% (w/v), or about 2% (w/v). In certain embodiments, the composition including a polynucleotide of this invention includes an ammonium salt at a concentration greater or equal to 300 millimolar. In certain embodiments, the composition including a polynucleotide of this invention includes an organosilicone transfer agent in a concentration of about 0.015 to about 2 percent by weight (wt percent) as well as ammonium sulfate at concentrations from about 80 to about 1200 mM or about 150 mM to about 600 mM.

Embodiments of transfer agents include a phosphate salt. Phosphate salts useful in a composition including a polynucleotide of this invention include, but are not limited to, calcium, magnesium, potassium, or sodium phosphate salts. In certain embodiments, the composition including a polynucleotide of this invention includes a phosphate salt at a concentration of at least about 5 millimolar, at least about 10 millimolar, or at least about 20 millimolar. In certain embodiments, the composition including a polynucleotide of this invention includes a phosphate salt in a range of about 1 mM to about 25 mM or in a range of about 5 mM to about 25 mM. In certain embodiments, the composition including a polynucleotide of this invention includes sodium phosphate at a concentration of at least about 5 millimolar, at least about 10 millimolar, or at least about 20 millimolar. In certain embodiments, the composition including a polynucleotide of this invention includes sodium phosphate at a concentration of about 5 millimolar, about 10 millimolar, or about 20 millimolar. In certain embodiments, the composition including a polynucleotide of this invention includes a sodium phosphate salt in a range of about 1 mM to about 25 mM or in a range of about 5 mM to about 25 mM. In certain embodiments, the composition including a polynucleotide of this invention includes a sodium phosphate salt in a range of about 10 mM to about 160 mM or in a range of about 20 mM to about 40 mM. In certain embodiments, the composition including a polynucleotide of this invention includes a sodium phosphate buffer at a pH of about 6.8.

Embodiments of transfer agents include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the composition including a polynucleotide of this invention is formulated with counter-ions or other molecules that are known to associate with nucleic acid molecules. Non-limiting examples include, tetraalkyl ammonium ions, trialkyl ammonium ions, sulfonium ions, lithium ions, and polyamines such as spermine, spermidine, or putrescine. In certain embodiments, the composition including a polynucleotide of this invention is formulated with a non-polynucleotide herbicide e. g., glyphosate, auxin-like benzoic acid herbicides including dicamba, chloramben, and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrinogen oxidase inhibitors, and 4-hydroxyphenyl-pyruvate-dioxygenase inhibiting herbicides. In certain embodiments, the composition including a polynucleotide of this invention is formulated with a non-polynucleotide pesticide, e. g., a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of this invention. All such similar substitutes and modifications apparent to those skilled in the art are deemed to be within the spirit, scope and concept of this invention as defined by the appended claims.

What is claimed is:

1. A method for controlling an insect infestation of a plant comprising contacting with a dsRNA an insect that infests a plant, wherein the insect is *Euschistus* spp., wherein the dsRNA comprises a sequence complementary to 21 or more contiguous nucleotides of an insect target gene that has a DNA sequence of SEQ ID NO: 9, and the complement thereof, wherein the contacting comprises application of a composition comprising the dsRNA to a surface of the *Euschistus* spp. insect or to a surface of the plant infested by the *Euschistus* spp. insect, and wherein the contacting results in mortality or stunting in the *Euschistus* spp. insect.

2. The method of claim 1, wherein the dsRNA comprises a sequence identical or complementary to 21 or more contiguous nucleotides of SEQ ID NO: 24 or 25.

3. The method of claim 1, wherein the dsRNA:
   (a) is (i) blunt-ended, or (ii) has an overhang at at least one terminus; or
   (b) is (i) chemically synthesized, or (ii) produced by expression in a microorganism, or (iii) produced by expression in a plant cell.

4. The method of claim 1, wherein the contacting:
   (a) comprises application of a composition comprising the dsRNA to a surface of the insect or to a surface of the plant infested by the insect;
   (b) comprises application of a composition comprising the dsRNA to a surface of the insect or to a surface of the plant infested by the insect, wherein the composition comprises a solid, liquid, powder, suspension, emulsion, spray, encapsulation, microbeads, carrier particulates, film, matrix, or seed treatment;
   (c) comprises providing the dsRNA in a composition that further comprises one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator;
   (d) comprises providing the dsRNA in a composition that further comprises at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein;
   (e) comprises providing the dsRNA in a composition that is ingested by the insect;
   (f) comprises providing the dsRNA in a composition that is ingested by the insect, wherein the composition that is ingested further comprises one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator;
   (g) comprises providing the dsRNA in a composition that is ingested by the insect, wherein the composition that is ingested further comprises at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein;
   (h) is of an insect in a larval or nymph stage, of an adult insect, or of an insect egg; or
   (i) results in mortality or stunting in the insect.

5. An insecticidal composition comprising an insecticidally effective amount of a recombinant dsRNA molecule, wherein the recombinant dsRNA molecule comprises a sequence complementary to 21 or more contiguous nucleotides of a target gene of an insect that infests a plant, and the complement thereof, wherein the insect is *Euschistus* spp., and wherein the target gene has a DNA sequence of SEQ ID NO: 9.

6. The insecticidal composition of claim 5, wherein the recombinant dsRNA molecule:
   (a) comprises at least one RNA strand having a sequence identical or complementary to 21 or more contiguous nucleotides of SEQ ID NO: 24 or 25;
   (b) is a dsRNA comprising an RNA strand having a sequence of SEQ ID NO: 24 or 25; or
   (c) is a dsRNA comprising an RNA strand having a sequence of SEQ ID NO: 24 or 25, wherein the dsRNA is at least 50 base pairs in length.

7. The insecticidal composition of claim 5, wherein the composition:
   (a) further comprises one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator;
   (b) further comprises at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein; or
   (c) is in a form selected from the group consisting of a solid, liquid, powder, suspension, emulsion, spray, encapsulation, microbeads, carrier particulates, film, matrix, soil drench, insect diet or insect bait, and seed treatment.

8. A plant treated with the insecticidal composition of claim 5, or seed of the plant, wherein the plant exhibits improved resistance to the insect.

9. A method of providing a plant having improved resistance to an insect, comprising expressing in the plant a recombinant DNA construct comprising DNA encoding a dsRNA that includes at least one silencing element comprising an RNA strand identical or complementary to 21 or more contiguous nucleotides of a target insect gene sequence that has the sequence of SEQ ID NO: 9, and the complement thereof, wherein the insect is *Euschistus* spp., and wherein ingestion of the dsRNA by the insect results in mortality or stunting in the insect.

10. The method of claim 9, wherein the silencing element has a sequence identical or complementary to 21 or more contiguous nucleotides of SEQ ID NO: 24 or 25.

11. The method of claim 9, wherein the recombinant DNA construct further comprises a heterologous promoter operably linked to the DNA encoding a dsRNA that includes at least one silencing element, wherein the heterologous promoter is functional in a plant cell.

12. The method of claim 9, wherein the recombinant DNA construct is provided to the plant by *Agrobacterium*-mediated transformation or by introduction in a recombinant plant virus vector or a recombinant baculovirus vector.

13. The method of claim 9, wherein the expressing is by means of transgenic expression or transient expression.

14. The method of claim 9, further comprising expression in the plant of at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

15. A plant having improved resistance to a *Euschistus* spp. insect, provided by the method of claim 9, or fruit, seed, or propagatable parts of the plant, wherein the fruit, seed, or propagatable parts of the plant comprises the recombinant DNA construct.

\* \* \* \* \*

SEQUENCE LISTING

<160> NUMBER OF SEQ ID NOS: 49

<210> SEQ ID NO 1
<211> LENGTH: 1125
<212> TYPE: DNA
<213> ORGANISM: Spodoptera frugiperda

<400> SEQUENCE: 1

```
ggtgacatgg ccaccatcca ggtatacgaa gaaacatcag gtgtaactgt aggtgacccc      60
gtgctgcgta ccggcaagcc cctgtccgta gagctgggtc ctggtatcct cggctccatc     120
tttgacggta tccagcggcc actgaaggac atcaacgagc tcacacagtc catctacatc     180
cccaagggtg tcaacgtacc ctgccttgga cgtgatgtca cctgggaatt caacccttg      240 aatgttaagg tcggctccca catcaccgga ggagacttgt acggtatcgt acacgagaac     300
acattggtta agcataagat gttgatccca cccaaggcca agggtaccgt cacctacatc     360
gcgccctccg gcaactacaa agtcactgac gtagtgttgg agacggagtt cgacggcgag     420
aaggagaagt acaccatgtt gcaagtatgg ccggtgcgcc agccccgccc cgtcactgag     480
aagctgcccg ccaaccaccc cctgctcacc ggacagagag tgctcgactc tctcttccct     540
tgtgtccagg gtggtaccac ggccatcccc ggcgccttcg gttgtggcaa gactgtcgtc     600
tcacaggctc tgtccaagta ctccaactct gacgtcatca tctacgtcgg atgcggtgaa     660
cgtggtaacg agatgtctga ggtactgcgt gacctccccg agctgacggt ggagatcgag     720
ggcatgaccg agtccatcat gaagcgtacc gcgctcgtcg ccaacacctc caacatgcct     780
gtagccgccc gagaggcttc catctacacc ggtatcaccc tctccgagta cttccgtgat     840
atgggttaca acgtgtccat gatggctgac tccacctctc gttgggccga agctcttcgt     900
gagatctcag gtcgtctggc tgagatgcct gccgactccg gttaccccgc ctacctggga     960
gcccgtctgg cctccttcta cgagcgtgcc ggacgtgtga agtgcctggg taaccccgac    1020
agggagggct ccgtgtccat cgtgggcgcc gtgtcgccgc ccggaggtga cttctccgac    1080
cccgtgacgg ccgccacgct gggtatcgtg caggtgttct ggggt               1125
```

<210> SEQ ID NO 2
<211> LENGTH: 2724
<212> TYPE: DNA
<213> ORGANISM: Spodoptera frugiperda

<400> SEQUENCE: 2

```
aactatgaaa cacattcgca gatcaagaga ttcgaggtat gcgacctacc ggtgcgcgcc      60
gctaagttcg tgcctcgcaa gaactgggtg attactggct ccgatgacat gcagattcgc     120
gtgttcaact acaacacgct tgagagagtg cacgcctttg aggcgcattc tgactacgtc     180
aggtgcatcg cgatacatcc cacacagcca tacatcctca ccagcagcga tgacctattg     240
atcaagctgt ggaactggga acgcaactgg gcatgccagc aagtgttcga gggccacaca     300
cattatgtga tgcagatcgt catcaaccct aaagacaaca acacattcgc tagtgctagt     360
ctcgacacca ccgtcaaagt atggcagctt ggctcttcaa tttccaactt cacattagaa     420
ggccacgaga aaggcgtgaa ctgcgtcgac tactaccacg gcggcgacaa gccttacctc     480
ataagtggtg ccgacgatcg cctcgtcaaa atatgggact accagaataa aacatgtgtc     540
```

```
cagacattgg agagtcacac gcagaatgtg acagccgtgt cgttccaccc ggagctgccg      600
atcctgatga ctggctcaga ggacggcacc atcagaatat ggcacgcagg cacttacaga      660
cttgaatcct cgctcaacta tggcttcgag agagtctgga ccatttcctc catgcacggc      720
tctaacaacg tagctattgg ttacgacgag ggcacgatca tgatcaaggt gggccgcgaa      780
gagccggcca tttccatgga cgtcaatgga ggcaagatta tttgggcgaa gcattctgag      840
atgcagcaag tcaacctgaa ggcgttgcca gaaggcacag agataaaaga tggagagcgg      900
gttccagtta tggcgaagga catgggatcc tgtgagattt atccacaaac tatagcacac      960
aacccgaacg tcggttcgt ggtagtgtgc ggggacggcg agtacattat ttacacggcc     1020
atggcactta ggaacaaggc gttcggcact gcacaggagt cgtctgggc gtttgatagc      1080 tcagagtatg cgacacttga gaactccagc accatcaagg tgttcaagaa cttcaaagag      1140
agaaagagtt caagcctga gtatggtgct gaaggaatat acggcggttt catgttgggc      1200
gtgaagtcca tcagcggtgt ggcgttctcc ttctatgatt gggagaactt ggagttgatc      1260
agacggattg agatccagcc gcggcacgtg tactggtcgg agagcggcaa cctggtgtgc      1320
ctggcggctg atgactcgta ctacgtgctc aagtataatg cagctgttgt gacgcgagct      1380
cgcgaaacca actccaacat cacagaagac ggcatcgaag acgcttttga ggtcgtgggt      1440
gcagtgaacg aggtggtaaa gacaggacta tgggtgggcg actgcttcat ctacacgaat      1500
tccttgaaca gaataaacta ctacgtcggc ggagagatcg tcaccatatc ccacctggac      1560
cacaccatgt acatcctcgg atacgtcgct aaggagaaca gactgtacct aaatgacaag      1620
gagttgaaca tagtgtcgta ctcgctgctg ctgtcggtac tggagtacca gacggcggtg      1680
atgcgcgcag acttcgagac agcagaccgg gtgctcccca ccataccgca agagcatcgc      1740
accagagtcg ctcacttcct agagaaacaa ggcttcaaac aacaagctct agcagtctct      1800
acggagcctg aacaccagtt cgagctggct ctctcactgg gagaacttag aagagcaaag      1860
cagttggccg aggaggcggc attggccgag ggttccacct cccgatcctc agcggcacgg      1920
tggtctcggc tgggagcggc cgccgccgcc gctgcagaca cggaactcac caaggcctgc      1980
tatcagagcg ctaaggacta cagtgccctc cttctattcg cagctagtac tggtgacaaa      2040
gaactgttga agagtgtagc acagatgtcc tcggaggaaa acgcggagaa tatctcattc      2100
gtggcctact ttatgctgaa tgatctcgaa tcctgtctga agctgctcat acagcgggac      2160
aagctgcctg aagccgcctt cttttgccaga tcatacattc catcgaaaat gtcggaagtg      2220
gtgaagttat ggcgcgagtc caccagcgcc accaacacga agctcggcca gtcgctcgcc      2280
gaccccggag cagtatgagaa tttgttcccc gagtttgcgc aatcattgga gttggagaga      2340
tttcagcgcg agtatgggta cgagcagagt tgcttgctag cgaacttgcc ggtcgactcg      2400
aagacttgca accttgagcg taaccttgcc accgagaagg aggaggccga gcaacgcggc      2460
tttaagctga gctccgctgc agtggcgcgg tctcctgcac acagctcaaa tgatcttggt      2520
cctgacgacc gagtcacaaa caatgatagt ccttcccacc cggtgccgga gagcacggtg      2580
gcgaccgcgg cgcagcagga tctgaagaaa cggcgcgact ctctcgacat catggaggaa      2640
ctggagcgcg agatcgaaga catcgtcctg gacggcacgg tcgagagcgt ggatctgtcg      2700
gacgatgtag atttcatgga ctaa                                            2724
```

<210> SEQ ID NO 3
<211> LENGTH: 2838
<212> TYPE: DNA
<213> ORGANISM: Spodoptera frugiperda

<400> SEQUENCE: 3

```
atgtgtataa gagacagcta tactctgatc aacttcccga ctgattcaga gccttacaat        60
gagatgcagc tcaagctgga tcttgagaaa ggygacacaa agaagaaaat agaagcatta       120
aagaaggtaa taggtatyat cytktctggk gagaagatwc cyggtctatt gatgatcatc       180
atccgattyg tgctgcccct gcaagaccac accatcaaga agctgttgct katcttctgg       240
gaaatagtgc caaagaccac tcctgatggc aagctcatgc aggagatgat ccttgtctgt       300
gatgcttaca gaaaggatct gcaacacccc aatgagttca tccgtggctc caccctgcgc       360
ttcctctgta aactgaagga gcctgaactc ctcgagcctt tgatgcccgc catcagagct       420
tgtcttgacc accgccactc atatgtcagg aggaatgctg ttcttgccat atttactatc       480
tacaggaact ttgaattcct gatccctgat gctccagagc tagtagcaaa cttcttggag       540
acagagcagg acatgtcctg caagaggaat gcatttctta tgctgctcca tgctgaccag       600
gagcgggcac tgtcctacct ctcatccagg ctggataatg tacagggctt tggagatatc       660
cttcagttgg ttattgtaga acttatttac aaggtttgcc acgcgaatcc atcagagagg       720
tctcgtttca tccgtacagt atacggctta ctgaacgcga ccagtgccgc cgtgcggtac       780
gaggctgccg gtactctcgt tacactgtct aacgcgcctg ctgctatcaa ggcggcggca       840
gcatgctaca tcgacctaat agtgaaggag agcgacaaca acgtgaagct gatagtggtg       900
ggtcggctgg gagcgctgcg cgcggaggcg ggcgaggcgg cggcgcgcgc gctgcccgag       960
ctggccatgg acgtgctgcg cgtgctggcc gcctccgacc tggacgtgcg ccgacacacg      1020
ctggcgctgg cgctcgacct cgtgtcctcc cgccacgccg aggacctcgt gcaggtgctg      1080
cggaaggagg ccgccgggc taccaacgca gaccacgatg atgctgccaa gtacaggcag      1140
ctacttgtta gagctctgca ccgagctgca ctcaagttcc ccgaagtagc cggcagtgta      1200
gccccggcgc tgctggagtt gctgggcgac ggcagtgagc cggccgcgca ggatgtcatg      1260
ctgttcctac ggtccgctct acataccttc gtgacctacg gatcatatct accagaaact      1320
gttggaggcg tgcccggta tcaaagtggt aagatagcgc ggtctgcgct gtggctgctg      1380
gcccagttcg ctgagactcc ggaacgcgcc aaggatgcct ggatgtact cgccaacgtc      1440
ataccttccc ttagcggaca agaggataag gaagaatccg agtcggcagc taaggcccag      1500
gacacttcag ctccacgaca gcttgtcacc agtgatggaa cttatgcttc gcagtctgct      1560
tttaacttgc cagttagcca agcggctcca acccacgcgg gtctatgggc ggcactaggc      1620
gagggcgaga gcttcacggc ggcgtgcgcg tgctcggcgc tgtgcaagct ggcgctgaag      1680
ctgtcgggcc gggccgcgac cgccgcgctg cagctggccg cgcgcctgct ggccgcccac      1740
aagctggccg ccgcctcac cgccgacgac gccgagcacg gcgcgcgatg tatactggcc      1800
gcgagacacc gcccgcccgt cgtacaggaa gcgctgctgc aacgctcctc tgctgcgctc      1860
gccgcgctgc tagcgctgcc tgaccgagct actaatctgc ttgatgatgc tgataaggaa      1920
cgtgagccaa agaagcaaga caacaaggtg gaggtggaac aaggcatcgt gttcgcccag      1980
ttggctggga actccgccgc ctccacacac cacgacatgt tcgagctatc gctcactaag      2040
gcactgcaag gccgcagtac cggcgtgagc gaggagcgcg gcaagctgtg gaaggtgacg      2100
cagctgaccg ggttctccga ccccgtgtac gccgaggcca tcgtcgccgt caaccagtac      2160
gacatcgtgc tcgacgtact cgtcgtcaac cagaccgacg acacgctgca gaactgctgc      2220
gtggagctgg cgacgctggg cgacctgcgg ctggtggagc ggcccggggc cgtggtgctg      2280
```

-continued

```
gcccccaggg actacgccac catcaaggcg cacgtcaagg tcgcctccac cgagaacggc    2340
atcatcttcg ggaacattgt gtacgaggta tcgggcgcgt cgatggaccg cggcgtggtg    2400
gtcctgaacg acatccacat cgacatcgtg gactacatcc agcccgccgt ctgcaccgac    2460
gcagacttca ggcagatgtg ggccgagttc gagtgggaga taaggtgtc cgtgaacacg     2520 aacatcacgg acctgcgcga gtacttacaa catttactag cttccacaaa catgaagtgt    2580
ttgacgcctg aaaaggcatt atcgggtcaa tgcgggttca tggcagccaa cctgtacgcg    2640
cggtccatat tcggcgagga cgcgctggcc aacctgagca tcgagacccc gctgcacaaa    2700
cccaactcgc ccgtcgtcgg acatgtcagg atcagggcca agagccaggg tatgcgcctg    2760
tctctaggcg acaaaatcaa catgatgcac aagacgccgc aacagaagac ccctccaac    2820 cccatccccg ccgcgtaa                                                   2838
```

<210> SEQ ID NO 4
<211> LENGTH: 2097
<212> TYPE: DNA
<213> ORGANISM: Lygus hesperus

<400> SEQUENCE: 4

```
ggttggtggt ttggttggac tggacgacat tctgcgaagt taactttgtc tacaaataac     60
agattcaacc atggctttac ccagaatccg tgatgaggag aaagaatcca gatttggata   120
tgtattcgcc gtttctggcc ctgtcgtcac tgccgagaag atgtcggggg ccgctatgta   180
cgagctggtg cgcgtcgggt acttcgagtt ggtcggcgaa atcattcgtc ttgaaggaga   240
catggccacc attcaggtct acgaagaaac atccggtgta acagttggag atcccgtgtt   300
gagaactggg aaaccacttt cggtggagct cggtccgggt attatgagca gcattttga    360 cggtattcag cgacctttga agacatttg cgagctgact cagagcatct acatccccaa    420
gggagtcaac gttccagctc tgtccaggtc tattgcatgg gacttcactc cgtccaacaa   480
tatcaaggtg ggagcacaca tcactggtgg tgatttgtat gccgtcgttc acgaaaacac    540
gcttgtcaag caaaaaatga tcatgccggc cagaggaagg ggtaccgtga atacatcgc     600 tccccctggc aactacactg ttgatgacgt cgtaatggaa actgaattcg acggagagaa    660
aactgaaatc aagatgttgc aagtttggcc tgtccgacag ccccgtccag ttgccgaaaa    720
actgcctgct aactatccac tcttgactgg tcaacgagtt ttggatgccc tcttcccgtg    780
tgtccaaggt ggtaccaccg ccattcccgg tgccttcggc tgtggaaaaa ctgtcatctc    840
acaagctctg tccaaatact caaactctga cgtcatcatt tacgtcggat gcggtgaacg    900
tggtaacgaa atgtctgagg tattgagaga tttccccgaa ctcacagttg agattgacgg   960
tgtaactgag tccatcatga gcgtactgc tctggtcgcc aacacatcca acatgcctgt    1020
agctgctcga gaagcttcca tttatactgg tatcacattg tccgaatact tccgtgacat    1080
gggttacaac gtgtcgatga tggctgactc cacctctcga tgggccgaag ccttgagaga   1140
aatttcaggt cgtctcgctg aaatgcctgc tgacagtggt taccctgcct acttgggagc    1200
ccgtttggct tccttctacg agcgagctgg tcgtgtcaaa tgtcttggaa gtcccgacag   1260
agagggctca gtcagtatcg tcggtgccgt gtcgcctcct ggtggtgact tttcggatcc   1320
tgtcacttca gccacccttg gtatcgtaca ggtcttctgg ggtctcgaca gaaaattggc    1380
acaaaggaaa cacttccct ccatcaactg gctcatctct acagtaagt acatgagagc      1440 tttggacgac ttctatgaca aacggtaccc tgaattcgtg cccctgagga ccaaggtcaa    1500
ggagatcctc caggaggaag aagatttggc tgaaattgtg cagctcgtcg gtaaaggttc    1560
```

```
gctggccgag tctgataaga tcacattgga aatcgctaag atcttgaaag acgatttctt    1620
gcaacaaaac agctactcgc cctacgacag attctgtccg ttctacaaga cggtcggtat    1680
gttgaagaac atgatctctt tctatgatct tgcgaggcac acggtggaat caacagcaca    1740
aagcgacaac aagatcactt ggactgtcat caaagaaagc atgggcaaca tcctctacca    1800
gctgtcctca atgaaattca aggaccccgt caaagacgga gaagccaaga tcaaaggcga    1860
cttcgaacag ctccacgaag acatgcaaca agctttccgc aacctcgaag actaaacagt    1920
tttctcgttc gctaccttat tgttgacaat agtggcacta cagattaact tcagtgcaat    1980
ttttaacagc aaccgcaaat atcctcctcc tcccccccct gaaactcata ctatcgttac    2040
acaatttgta catataaaaa cacgtctgtt gtaattacac ataattattg tatatct      2097

<210> SEQ ID NO 5
<211> LENGTH: 701
<212> TYPE: DNA
<213> ORGANISM: Lygus hesperus

<400> SEQUENCE: 5
ggtggttctc ttcgtccgac catgagttcg ctcaaactgc agaagaggct cgccgcctcg      60
gtgatgagat gcggcaagaa gaaagtgtgg ttggacccta atgaaatcaa cgaaatcgcc     120
aacaccaact ctaggcaaaa catccgtaag ctgatcaagg atggtttgat catcaaaaag     180
cctgtggctg tccactccag agcccgcgtc cgtaaaaaca cagaagccag acggaagggt     240
cgtcactgtg gcttcggtaa gaggaagggt accgccaacg ccagaatgcc tgtgaaggtc     300
ctgtgggtca acagaatgag agtcctgcga cggctcctta aaaatacag agaagccaag      360 aagatcgata ggcaaatgta ccacgacctt tacatgaaag ccaaaggtaa cgtcttcaaa     420
aacaagaggg tactgatgga cttcattcac aagaagaagg ctgaaaaggc gagatcaaag     480
atgttgaagg accaggcaga ggcgagacgt ctcaaggtca aggaggcgaa gaagaggcgc     540
gaggagagga tcgccaccaa gaagcaagag atcatgcagg cgtacgcccg agaagacgag     600
gctgccgtca aaagtgatc tcgcccctc cgttttaa ttttaaacaa aaacgtatt         660 ttgtacaaaa atctacaaaa aaattacaaa agagaaaact t                       701

<210> SEQ ID NO 6
<211> LENGTH: 2817
<212> TYPE: DNA
<213> ORGANISM: Lygus hesperus

<400> SEQUENCE: 6
atgcctctca aattggacat caagagaaag ctgtctgctc gatcagaccg tgtgaaatgt      60
gtcgatctgc acccaactga gccctggatg ttggcttctc tctacaacgg aaacgttcac     120
atttggaacc acgaaactca acagcttctg aaatccttcg aagtatgcga gcttccaatc     180
agggctgcag ttttcgtacc gaggaagaac tgggtggtca caggctcgga cgacatgcac     240
gttcgtgtct tcaactacaa cactctcgag cgtgtacatt ccttcgaggc ccattctgat     300
tatttgagat gcatcatcgt acatcctaca cagccttaca tattgacgtg cagcgatgac     360
atgctgatca agctgtggaa ctgggaaaaa actggctgt ccagcaagt cttcgaaagc       420 cacacccatt acgtcatgca gatcgtgctg aacccgaagg ataacaacac tttcgcctct     480
gcctcgctcg accacacgct caagtgtgg cagtgggct cagcagcggc caacttcact       540
ttggacggac acgaaaaagg agtgaactgc gtcgactact accacggagg agataagcct     600
```

```
tatctcatct ctggcgcgga cgatcacatg gtcaaaatat gggattacca gaacaaaacg    660
tgcgtccaga ctttggaggg acacgctcaa aatataactg cagtttgctt ccacactgaa    720
ctaccaatcg caattactgg ctcggaagat ggaaccgttc gcttgtggca ctcagccacc    780
tatcggttgg aatcgtcctt gaactacggc tttgaaagag tatggaccat acgctgtctc    840
aaaggctcaa accacattgc tcttgggtac gacgagggtt ccattatggt caaagttggt    900
cgagaagaac cggccatttc catggatgta aatggagaaa aaattgtttg gctcgacat     960 tctgaaatcc agcaggtcaa tttgaagtct ctcatgactg acgagagtga aattcgcgat   1020
ggggagaaac tcccagtagc agctaaagac atgggtccct gcgaagtttt cccgcaaagc   1080
atcgcccaca accccaatgg aagatttgtg gttgtttgcg gtgatggaga atacatcatc   1140
tacactgcca tggctttgcg taataaaagt ttcggttccg cgcaagagtt cgtctgggcg   1200
caggactcgt ccgactacgc catccgcgaa gggacgtcta cggtccgact tttcaggcag   1260
ttcaaggaaa ggaagaactt caagcctgaa tttggagctg aaggtatttt tgggggacag   1320
cttctcggag ttaggactgt aactggactg tccctctacg actgggaaac tttggagttg   1380
atcagaagca tcgacattca agcgaaagcg ctgtactggt ccgaagcagg gcatctcttg   1440
gcaatcgtta ctgacgacag ttactatctc ttgaaattcg accagagcgc catctcgacg   1500
tccacccctg aactgacgg ctacgaagat gcctttgagc tcgtcggtga agtcaatgat   1560
actgtcaaga ccgattgtg ggttggtgac tgtttcatct acacaaacgc cgtttgtcgg   1620
atcaactact acgtaggtgg tgagatcgtc accgtggctc acctcgacac tacaatgtac   1680
ctcctaggat acgtggcccg tcagaacctg ctgtacctgt gcgacaagca tcataacatc   1740
atttgttaca cgttgcttct gtctgtcctc gaatatcaga ctgctgtgat gaggagagac   1800
tttgaaactg ctgaccgagt tttgcccact attcctgttc agcatcgctc aagagttgct   1860
catttcctgg agaaacaggg cttcaaaagg caagctctgg ctgtgtccac ggatgccgag   1920
cacaagtttg aacttgcgct tcagctcagt gatttggaag cagcagtcgg cctagcgagg   1980
gaaatcggca gcaaagccaa gtgggttcag gtcgccgagt tggcgatgtc agaggccaag   2040
ctcggactcg ctcagatgtg cttgcatcag gcacagcact acggaggact tctgctcctg   2100
tcaacttctg ccggaaatgt ggacatgatg gagaaactgg ccgaaagctc gctgtccgat   2160
ggcaaaaaca acgtctcgtt cctcacttac ttcctgatgg gtaacgtgga aaagtgtctc   2220
caaatcctca tcgatactgg aagaattccg gaagcagctt tcttcgcccg gacctatatg   2280
cctaaagaag tgtcccgcgt ggtcgacatg tggaaaactc tttctaagga caagacgggg   2340
caatcgctcg ctgacccagc ccaataccg aatctattcc ccaagcacac cgaggctctg   2400
aaagccgaac agttcatgaa gaaggaattg actcaaagga ttcccgcctc gtcgcacaag   2460
gatataaaac ccaactacga aaggaatgcc attgaagaaa tgaaagaagc cgaagcaaac   2520
ggtctgttca cgtatgatcc tccagtggct cctgccagta tcaacaatct aattgatgtt   2580
tctgaaccgg cgaatcgatc tgagcccagc ccgtccgaaa tcttctccga agcgcccgcc   2640
gtgtccaaga tgaccagcga cgctcggccg ctggtcgcgc cagttccgcc tgccgcgaga   2700
cctcaaaaac ggccgtcggc cttcgatgat gacgacctcg aattggaaat cgaaaatatg   2760
aatttggatg acatcgatgc tagtgatttg aacgaagaag acctccttat agattag    2817
```

<210> SEQ ID NO 7
<211> LENGTH: 5621
<212> TYPE: DNA
<213> ORGANISM: Lygus hesperus

<400> SEQUENCE: 7

```
actcgttcta gatcgcgacg gacgcgtgga cgagaaacga gaacgagcta cgttgagcat      60
caagagcttt tgtactattg aaattgtgaa aaatgcagat cttcgttaaa actttgactg     120
ggaagaccat caccctcgag gtcgagcctt ctgataccat tgaaaacgtg aaggcgaaaa     180
ttcaggataa agaaggcatc cccccagatc agcagaggtt gatctttgcc ggcaagcagt     240
tggaagacgg acgtactttg tctgactaca acatccaaaa agaatccact ctccacctgg     300
tcttgagatt gagaggtggc atgcagatct tcgtgaagac cctcacagga agaccatca     360
ctcttgaggt cgagccttct gacaccatcg aaaacgtcaa ggctaaaatt caagacaagg     420
aaggtattcc tccagatcag cagagattga tcttcgccgg caaacaactc gaagatggcc     480
gtaccctctc tgactacaat attcaaaaag agtccaccct tcacttggtg ttgagattgc     540
gtggaggtat gcaaatcttt gtcaaaacat tgactggaaa gaccatcacc cttgaagtcg     600
aaccctccga caccatcgaa aatgtcaagg ccaagatcca ggacaaggaa ggcatccccc     660
cagatcagca gaggttgatt tcgctggca aacaacttga agacggacgt accctctcgg     720
actacaacat ccagaaggag tcgacccctcc atcttgtcct ccgtctgcgt ggtggtatgc     780
agattttgt caaaactctg actggcaaga caatcaccct tgaagtagag ccctctgaca     840
ccatcgaaaa tgtcaaggcg aaaatccagg acaaagaagg catccccca gatcagcaga     900
ggttgatctt tgccggtaag cagcttgaag acggccgcac cctctcggac tacaacatcc     960
agaaggagtc cacccttcat cttgtcctac gtctgcgtgg tggtatgcag attttcgtaa    1020
agaccttgac tggcaagacc atcactcttg aggttgagcc ctctgacacc atcgaaaacg    1080
tcaaggccaa gatccaggac aaggaaggta tcccccaga tcagcagagg ttgatcttcg    1140
ctggcaagca gctcgaagat ggtcgtaccc tctcggacta caacatccag aaagagtcca    1200
cccttcatct tgtcctccgt ctgcgtggtg gtatgcagat tttcgtaaag accttgactg    1260
gcaagaccat cactcttgag gtcgagccct ctgacaccat tgaaaacgtc aaggccaaga    1320
tccaggacaa ggaaggtatc ccccagatc agcagaggtt gatcttcgcc ggtaagcaac    1380
ttgaagacgg ccgtaccctc tcggactaca acatccagaa ggagtccacc cttcatcttg    1440
tcctccgtct gcgtggtggt atgcagatat tcgtaaagac cttgactggc aagaccatca    1500
ctcttgaggt cgagccctct gacacccttg aaaccgcaa ggccaagatc caggacaagg    1560
aaggtatccc cccagatcag cagaggtgtg atcttcgccg gtaagcaact tgaagacggc    1620
cgtaccctct cggactacaa catccagaag gagtccaccc ttcatcttgt cctccgtctg    1680
cgtggtggta tgcagatatt cgtaaagacc ttgactggca agaccatcac tcttgaggtc    1740
gagccctctg acaccattga aaacgtcaag gccaagatcc aggacaagga aggtatcccc    1800
ccagatcagc agaggttgat cttcgctggc aagcagctcg aagatggtcg taccctctcg    1860
gactacaaca tccagaaaga gtccaccctt catcttgtcc tccgtctgcg tggtggtatg    1920
cagattttcg taaagacctt gactggcaag accatcactc ttgaggtcga gccctctgac    1980
accattgaaa acgtcaaggc caagatccag gacaaggaag gtatcccccc agatcagccg    2040
aggttgatct tcgctggcaa gcagctcgaa gatggtcgta ccctctcgga ctacaacatc    2100
cagaaagagt ccacccttca tcttgtcctc cgtctgcgtg gtggtatgca gattttcgta    2160
aagaccttga ctgggaagac catcactctt gaggtcgagc cctctgacac cattgaaaac    2220
gtcaaggcca agatccagga caaggaaggt atccccccag atcagcagag gcagatcttc    2280
```

```
gccggtatgc aacttgaaga cggccgtacc ccgagaaacg agaacgggct acgttgagca    2340
tcaagagctt ttgtactatt gaaattgtga aaaatgcaga tcttcgttaa aactttgact    2400
gggaagacca tcaccctcga ggtcgaacct tctgatacca ttgaaaacgt gaaggcgaaa    2460
attcaggata aagaaggcat cccccagat cagcagaggt tgatcttcgc cggtaagcag     2520
cttgaggatg gacgtactct ctcggattac aacatccaga aggagtcaac cctccacctt    2580
gtcctccgtc tgcgtggtgg tatgcagatc ttcgtcaaga ccttgactgg caagacgatc    2640
actttggaag tcgagccctc tgacaccatt gagaatgtca aagccaaaat ccaagataag    2700
gaaggcatcc ccccagatca gcagaggttg atcttcgccg gtaagcagct tgaagacggc    2760
cgtactctct ctgattacaa catccagaag gagtcgaccc tccaccttgt cctccgtctt    2820
cgtggtggta tgcagatttt cgtaaagacc ttgactggca agaccatcac ccttgaggtc    2880
gagccctccg acaccatcga aaacgtcaag gccaagatcc aagataagga aggcatcccc    2940
ccagatcagc agaggttgat cttcgccggt aagcagcttg aggatggacg taccctgtca    3000
gactacaaca tccaaaagga gtccaccctg cacttggtgt tgagattgcg tggtggtatg    3060
cagatcttcg tcaagacctt gactggcaag acgatcactt ggaagtcga gccctctgac     3120 accattgaga atgtcaaagc caaaatccaa gataaggaag catcccccc agatcagcag     3180 aggttgatct tcgctggtaa gcaacttgaa gacggccgca ccctctctga ctacaacatc    3240
cagaaggagt cgaccctcca tcttgtcctc cgtctgcgtg gtggtatgca gattttcgtg    3300
aagaccttga ctggcaagac catcacccct tgaagtcgagc cctctgacac cattgagaat    3360
gttaaagcca gatccagga caaggaaggt atccccccag atcagcagag gttgatcttc     3420
gccggtaagc agcttgaaga cggccgtact cttcggatt acaacatcca aggagtcg       3480 accctccacc ttgtcctccg tctgcgtggt ggtatgcaga tcttcgtcaa gaccttgaca    3540
ggcaagacca tcaccttga agtcgagccc tctgacacca tcgaaaacgt caaggctaag    3600
atccaggaca aggaaggcat cccccagat cagcagaggt tgatcttcgc cggtaaacag     3660
cttgaagacg gacgtacccct ctcggactac aacatccaaa aggagtccac tcttcacttg    3720
gtgttgagat gcgtggtgg tatgcagatc ttcgtcaaga ccttgacagg caagaccatc     3780
acccttgaag tcgagccctc tgacacaatt gaaaacgtca aggccaagat ccaggacaag    3840
gaaggtatcc ccccagatca gcagaggttg atcttcgccg gtaagcagct tgaagacggc    3900
cgtactctct ctgattacaa catccagaag gagtcgaccc tccaccttgt actccgtctg    3960
cgtggtggta tgcaaatttt cgtgaagacc ttgactggca agaccatcac tcttgaggtc    4020
gagccctctg acaccattga aaacgtcaag gccaagatcc aggacaagga aggtatcccc    4080
ccagatcagc agaggttgat cttcgccggc aagcagctcg aagacggccg tactctctct    4140
gattacaaca tccagaagga gtccacccctt catcttgtcc tccgtctgcg tggtggtatg    4200
cagattttcg tgaagacctt gactggcaag accatcactc ttgaggtcga gccctctgac    4260
accattgaaa acgtcaaggc caagatccag gacaaggaag tatccccccc agatcagcag    4320
aggttgatct tcgctggcaa gcagctcgaa gatggtcgta ccctctcgga ctacaacatc    4380
cagaaagagt ccaccctcca ccttgtcctt cgtctgcgtg gtggtatgca gattttcgta    4440
aagaccttga ctggcaagac catcactctt gaggtcgagc cctctgacac cattgaaaac    4500
gtcaaggcta agatccagga caaggaaggc atccccccag atcagcagag gttgatcttc    4560
gccggtaagc agcttgaaga cggccgtact ctctctgatt acaacatcca aggagtcg     4620 accctccacc ttgtcctccg tcttcgtggt ggtatgcaga ttttcgtgaa gaccttgact    4680
```

```
ggcaagacca tcacccttga ggtcgagccc tccgacacca tcgaaaacgt caaggccaag    4740
atccaagata aggaaggcat ccccccagat cagcagaggt tgatcttcgc cggtaagcag    4800
cttgaggatg gacgtactct ctcggattat aacatccaga aggagtcaac cctccacctt    4860
gtcctccgtc tgcgtggtgg tatgcagatc ttcgtcaaga ccttgactgg caagacgatc    4920
actttggaag tggagccctc tgacccatt  gagaatgtca aagccaaaat ccaagataag    4980
gaaggcatcc ccccagatca gcagaggttg atcttcgccg gtaagcaact tgaagacggc    5040 cgcacccttct ctgactacaa catccagaag gagtccaccc tccatcttgt ccttcggctg    5100
cgtggtggta tgcagatctt cgtcaagacc ttgacaggca agaccatcac ccttgaagtc    5160
gagccttctg acaccatcga gaacgtcaag gccaagatcc aggacaagga aggtatccct    5220
ccagatcagc aaagattgat cttcgccggc aaacagctcg aagatggccg taccctctca    5280
gactacaaca ttcaaaagga gtcaactctt catctcgttc tgaggctccg tggcggtcgt    5340
tattgatcac aattccaaac ttaaaaattg cattccgatt tccttctttt atttggcaaa    5400
aaatacatac cctagttaat taaaatgact tgaaatttga ttttttaaga atgcttcaaa    5460 ttttttata  gatggtttgt tacatagaca atacacaaca tgttgaaagc ataaaaaaaa    5520 aaaaaaaaa  aaaaaaaaa  aaaaaaaaac caaaaaaaaa aaaggggggg gcccgttcaa    5580
aaggaccaaa gttaacgacc gcgggatggc aacgcattac t                        5621

<210> SEQ ID NO 8
<211> LENGTH: 1927
<212> TYPE: DNA
<213> ORGANISM: Euschistus heros

<400> SEQUENCE: 8
gtttgttgta gttacaggtt ttaatttggt tcacatccta agttcggcaa ttcagatgtc      60
tacttccaaa acagaagaaa agcccttgtg ggacgaaaga atggagcaag ctttaggtga     120
agaaatcatg agaatgtcta cggatgaaat tgtcagtcgt attaggcttc ttgataatga     180
aattaaaatc atgaaaagtg aagtcatgcg agtcagtcat gagttgcagg cacaaacaga     240
aaaaattaag gaaaatacag aaaagatcaa agtgaacaaa actttaccat atttagtatc     300
taatgtgata gagttgcttg atgttgatcc agaggaaact gaggaagatg gtgctgttgt     360
tgaccttgat gcccgtcgta aaggaaaatg tgctgtcatt aaaacatcaa cgaggcagac     420 ttatttttg  ccagtaatag gcttagttga tgctgaaaag ttaaagccag gtgatctggt     480
tggagtaaac aaagattctt atttaattct tgaaaccttg cctgctgagt atgatgcacg     540
agttaaagca atggaagttg atgaaagacc tactgagcag tattctgata tcggtgggct     600
tgataagcag attcaagaat taatagaagc cgttgttctt cctatgacac acaaagaaaa     660
atttgaaaat ctaggaattc atcctcctaa aggtgtattg ctctatggac ctcctggaac     720
aggaaagact ttactggcta gagcgtgtgc agctcaaact aaatcaactt ttttgaaact     780
agctggaccc caacttgttc agatgtttat aggagatgga gccaaacttg tcagagatgc     840
ttttgctctt gctaaggaaa aatctcctgc tattatcttt attgacgagt tggatgctat     900
tggaacaaaa agatttgatt ctgaaaaagc tggtgatcga gaagttcaaa gaactatgtt     960
agaactgctc aaccagttag atggatttag ctcaacagct gatattaagg ttattgcagc    1020
tacaaataga gtagatattt tggatcccgc ccttttgcgt tcaggtcgac tagacagaaa    1080
aattgaattc ccacatccta acgaagatgc ccgagcacgt ataatgcaaa ttcattctcg    1140
```

```
taagatgaat attagtgttg atgttaattt tgaagaactt gctcgttcaa ctgatgattt   1200
caatggagct caatgcaaag cggtttgtgt ggaagcaggt atgatagcat tgcgaagagg   1260
agctggagtt gtcactcatg aagatttcat ggatgcaata ttagaagtgc aggcaaagaa   1320
gaaagccaac ttaaactatt atgcttaaat atctattgat aaagattttt ttaataatgc   1380
agaaactcac ttgcattctt cttttcggga gtgccaataa ctgtgattga ttttgtattg   1440
ttattaactt gtaaatatgc cactctttga aaaacaaatg tgtaagtaaa ccaacaagta   1500
aaatagcaca ttataatttt attaaattct taaagtcgca ttaactccag ttaaaaaagt   1560
tttgttaatt catatatata tatatatttt tgcctgttta attttaaaaa gattatattt   1620
tctgtatcaa ttattagttt gactaatttg attactagtt tgaaatgagt ttctgccaga   1680
tttaatattt aattttatt tttataatca ttttcaaaat taattatttg ttggttcaca   1740
gtttattgaa tatattctaa tctcaaattt gttttttaat ttattttttc attgcattta   1800
atattttttg gattaaattg aaaggagatt aaacttcctg ttgcaaaatt tttttcagt    1860 gattctttat attatttgta tatttataaa tttgggaaac atttaataat atcatgttat   1920
gtttgtt                                                             1927

<210> SEQ ID NO 9
<211> LENGTH: 2170
<212> TYPE: DNA
<213> ORGANISM: Euschistus heros

<400> SEQUENCE: 9
ttacattaga agttgagcct tctgacacaa tagaaaatgt caaggccaaa atccaagaca     60
aagaaggaat ccctccagac caacagaggt tgtatttttg ctggtaaaca gcttgaagat    120
ggccgtactc tttcagatta caatattcaa aaagaatcta cttttcattt agtacttcgg    180
ttgagaggag gcatgcaaat ttttgtgaag accttgactg gtaaaaccat caccttggaa    240
gtggagccat ctgatacaat tgaaaatgtt aaagctaaaa ttcaagataa agaaggaatt    300
cctccagacc aacagaggtt gattttttgca ggtaaacagc tcgaagatgg tcgtacattg    360
tctgactata atattcaaaa ggaatctact cttcatcttg tcctacgttt aagaggaggc    420
atgcagatct tgtcaagac acttactggt aaaacaatca cacttgaagt tgagccttca    480
gacacaattg aaaatgtgaa agctaaaatt caagataaag aaggaattcc tccagatcag    540
cagaggttga ttttgcagg taaacagctc gaagatggtc gtacattgtc tgactataat    600
attcaaaagg aatctactct gcatttggtc cttcgtctga gaggaggaat gcaaatttttt   660 gtaaaaaacct tgactgggaa aactattaca ttagaagtgg aaccttctga cactattgaa    720
aatgttaaag ctaaaattca agataaggaa ggaattccac cagatcagca gcgattgatc    780
tttgctggaa aacagttgga agatggtcgt actttatctg attataacat tcagaaggaa    840
tcaacactac atttagtatt acgtttaaga ggtggaatgc agattttgt taagacgctt    900 actggaaaaa ccataacttt agaagttgaa ccgtcagata ccattgaaaa tgtaaaagcc    960
aaaattcaag ataaggaagg aattccgcca gatcagcaaa ggctgatctt gcaggaaaa    1020 cagttagaag atgggcgtac tctttctgat acaacatcc aaaaggaatc tactttacat   1080
cttgtactta gacttcgagg aggcatgcag atctttgtca agactttaac agggaagacc   1140
atcaccttag aagttgaacc atctgatact attgagaacg taaaagcaaa atccaggac    1200 aaagaaggaa ttccaccaga ccagcaacgt ttgatctttg ctggaaaaca acttgaagat   1260
ggccgtaccc tttcagatta taatattcaa aaagagtcta ctcttcatct tgtacttcgc   1320
```

```
ttgagaggtg gcatgcagat ttttgtaaag actctaactg gtaagaccat aaccttggaa    1380
gttgagccct tcagatacta tgagaatgtt aaagccaaaa ttcaagataa agaaggaata    1440
ccaccagacc aacagaggct tattttgct ggaaagcagc tggaagatgg ccgaactttg     1500
tctgattaca acattcaaaa ggaatcaaca ctgcatttgg tgcttcgtct aagaggaggc    1560
atgcagatct tgtgaagac tttgacaggt aaaaccatta ccttggaagt agagccatct    1620
gatacaattg agaatgtaaa agctaaaatt caggataaaa aaggaattcc tcccgaccag    1680
cagcgtttga tctttgctgg aaaacaactc gaagatggcc gtacccttc agattataat     1740 atccagaagg aatctacact acatctggtc cttcgattga gaggtggtat gcagatcttt    1800
gtcaagaccc tcacaggcaa gactattacc ttagaagttg agccatctga cactattgaa    1860
aatgttaaag ccaaaattca ggacaaagaa ggaatacctc cagatcagca gaggcttat    1920 tttgctggaa acaattaga ggatggtcgt accctatctg attataacat ccagaaggaa     1980
tcaactctgc atttagtgtt gcgtcttagg ggcggatatt aaggctactt atcatttcat   2040
tccatcaaaa ttccatatca gtaaattgct tttgatattt ttattagcat tttcattatt   2100
atatttataa ttatttcata aatacaatgt aactaaacta gaaataaaca gtttctttaa   2160
gttcaaaaaa                                                         2170

<210> SEQ ID NO 10
<211> LENGTH: 2360
<212> TYPE: DNA
<213> ORGANISM: Plutella xylostella

<400> SEQUENCE: 10
atgagtcacg ggttgaagag gattgccgac gaggacaatg aaacccagtt cggttatgtc      60
ttcgctgtgt ccggtcccgt ggtcacagcg gagaagatgt ccggctcggc catgtacgag     120
ctggtgcgcg tcggctacaa cgagctggtc ggcgagatca tccgtctgga gggggacatg     180
gccaccatcc aggtgtacga agagacctca ggcgtgaccg tcggcgaccc cgtgctgcgc     240
accggcaagc ctctctctgt agaactggga cccggcatcc tcggctccat cttcgacggc     300
atccagcggc cgctgaagga catcaacgag ctcacgcaga gcatctacat ccccaagggg     360
gggaacgtgc ccgcgctggc ccgcgacacc gagtgggagt tccacccgca gtacatcaag     420
agcgatgtct cggctggtat ccgaaccccg gtctccgccg ggcgcgtcct cggctccatc     480
tccgacggca tccagcggcc gctgaaggac atcaacgagc tcacgcagag catctacacc     540
cccaaggggg tgaacgtgcc cgcgctggcc cgcgacaccg agtgggagtt ccacccgcag    600
tacatcaaga gcgatgtctc ggccggtatt cgaaccccgg tctccgccgg gcgcgtcctc    660
ggctccatct ccgacggcat ccagcggccg ctgaaggaaa tcaacgagct cacgcagagc    720
atctacatcc caaggcggt gaacgtgccc gcgctggccc gcgacaccga gtgggagttc     780
cacccgcagt acatcaagcg ttgtcctgtc tctgccggta ttcgaacccc ggtctccgcc    840
gggcacgtcc tcggctccat ctccgacggc atccagcggc cgctaaagga catcaacgag    900
ctcacgcaga gcatctacat ccccaagggg gtgaacgtgc ccgcgctggc ccgcgacacc    960
gagtggcagt caacccgca gtacatcaag gtcggcaccc acatcaccgg cggagacttg    1020
tacgggatcg tgcacgagaa cacgctggtg aagcaccgca tgctggtgcc gcccaaggcc    1080
aagggcaccg tcacctacat cgcgcccgag gggaactaca agtcactga cgtggtccta    1140 gagaccgagt tcgacggcga gaagtcctcc tacaccatgc ttcaagtgtg gccggtgaga   1200
```

-continued

| | |
|---|---|
| cagccgcggc cgtgcaccga gaaactaccc gccaaccacc ccctgctgac cgggcagaga | 1260 |
| gtgctcgact cactgttccc caacagtgac tgcatggaga aactagccaa tcacccgctg | 1320 |
| ctgatcggcc agagagtgct cgaatcactg ttcccttgcg tccagggcgg caccacggcc | 1380 |
| atccccgggg ccttcggttg cggcaagacc gtcatctcgc aggcgttgtc caagtactcc | 1440 |
| aactctgacg tcatcgtcta tgtcgggtgt ggggagcgtg gtaacgagat gtccgaagta | 1500 |
| ctgcgtgact cccccgagct gacagtcgag atcgacggcg tgaccgagtc catcatgaag | 1560 |
| cgcacggcgc tcgtggccaa cacctccaac atgccagtgg ccgcccgaga ggcctccatc | 1620 |
| tacaccggaa ttaccctatc cgaatacttc cgtgacatgg gctacaacgt gtccatgatg | 1680 |
| gccgactcga cctcccgttg ggccgaagcg ctgcgtgaga tctcgggtcg tctggccgag | 1740 |
| atgcccgctg actctggtta ccccgcgtac ttgggagcta gactggcgag cttctacgag | 1800 |
| agggctggca gggtcaagtg tctgggtaac ccggagaggg aaggttcggt ctccatcgtg | 1860 |
| ggcgccgtgt cgccgcccgg aggagacttc tctgaccccg tgacggcggc cacgctcggt | 1920 |
| attgttcagg tgttctgggg gctggacaag aagctggcgc agaggaagca cttccctcc | 1980 |
| atcaactggc ttatttctta cagtaagtac atgcgcgcgc tggacgactt ctacgacaag | 2040 |
| aactaccccg agttcgtgcc gctcaggacc aagacagtta ctcgaactac gaccgtttct | 2100 |
| gcccgttcta caagacgacc ggcatgctga agaacatcat cacgttctac gacatgtcgc | 2160 |
| gacacgccgt cgagtccacc gcgcagtccg acaacaaggt gacgtggaac acgatccgtg | 2220 |
| acgccatggg acccgtgctc taccagctgt ccagcatgaa gttcaaggac cccgtgaaag | 2280 |
| atggagaagc caagatcaag gctgacttcg accagatcgt cgaggacatg gccgctgcct | 2340 |
| tccgtaacct agaggactaa | 2360 |

<210> SEQ ID NO 11
<211> LENGTH: 2030
<212> TYPE: DNA
<213> ORGANISM: Plutella xylostella

<400> SEQUENCE: 11

| | |
|---|---|
| atgccgttga gattggatat caagaggaag ctgacggctc gctcggaccg cgtgaagtgc | 60 |
| gtggaccagc acccctcgga gccctggctg ctatgctccc tgtacaatgg ggatgtcaac | 120 |
| atatggaact acgagacaca gctgcaaata aaaagatttg aggtaagtgt atgcgacttg | 180 |
| ccagtccgtg cggccaagtt tgtgccgagg aagttctggg tgatcaccgg ctccgatgac | 240 |
| atgcaaattc gtgtcttcaa ctacaacaca ctggaacgtg tacacaattt tgaagctcat | 300 |
| tcagactatg tgaggtgtat tgcggttcac cccacccagc catacatctt gaccagcagt | 360 |
| gatgatcttc tgataaagct ttggaactgg atcgcaact ggacttgcca gcaagtgttc | 420 |
| gagggacaca cgcactatgt gatgcagatt gtcatcaacc ccaaagacaa caacactttt | 480 |
| gccagtgcca gtcttgacag aaccgtcaag gtatggcagc tgggctcttc catcccgaac | 540 |
| ttcactctgg aaggtcacga aagggagtc aactgcgtgg actactacca cggcggggac | 600 |
| aagccgtacc tcatcagtgg agctgatgac cgcctcgtca agatatggga ctaccagaac | 660 |
| aagacttgtg ttcagacctt ggaaggtcac gcccagaatg tgtcagcagt gtccttccac | 720 |
| cccgagctac cgatcctgct gactggctca gaggacggca cggtgcgcat ctggcacgcc | 780 |
| ggcacctacc ggctcgagag ctcgctgaac tacggcttcg agcgagtctg gactatatcc | 840 |
| tccatgcatg gtccaataa tgtcgctgtt ggttacgacg aagggactat aatgataaaa | 900 |
| gtaggacggg aggagccggc tatttccatg gacgtcaacg gcggcaaaat catctgggcc | 960 |

-continued

```
aaacactcag agatgcaaca agtcaacttg aaagctttac cagaaggtac acacataaag   1020
gatggcgaga ggctgccatt ggtggtaaaa gacatgggtt cttgcgagat ctatccacag   1080
acgatagccc acaacccgaa cggcagattc gtggtagtct gcggagatgg ggaatacatc   1140
atctacacag ccatggcttt gaggaataag gctttcggca atgcgcagga gtttgtgtgg   1200
acgtttgaca gctcggagta tgccacactg gagaactcca gcactatcaa agtgttcaag   1260
aacttcaagg agcggaagag cttcaaaccg gagtatgggg ctgaaggaat atttggcggt   1320
ttcatgctgg gcgtgaagtc aatcagtggg gtttccttct ccatctacga ctgggaacat   1380
ctggagctca tcagacgcat cgagatccag ccccgccacg tgttctggtc ggagagcggc   1440
agtctagtct gtctggcgac ggacgaaagc tactacattc tgcgctacaa cgccgccgtc   1500
gtcaccaagg cgcgcgagac taacaccaac atcacagagg acggcattga ggatgccttt   1560
gaggtggtcg gcgaagtgaa cgagacagta aagacgggca tctggatcgg ggactgcttc   1620
atctacacca actctctcaa cagaataaac tactatgtcg gcggcgagat cgtcacgata   1680
tcgcatctcg atcacaccat gtacatactt ggatacgtag ctaaggaaaa cagactatac   1740
ctgaacgaca aggagctcaa cgtggtctcc tattccctcc tgctgccggt gctggagtac   1800
cagacggcgg tcatgcgagg ggacttcgag acggcggaca aggtgctgcc ggtcataccg   1860
cacgagcacc ggacgagagt cgcgcacttc ctcgagaaac agggcttcaa gcagcaagcg   1920
ctagccgtgt ccacggagcc ggaacaccag ttcgagctgg ccctagcttt aggcgagctc   1980
cgaagagccc gccaactagc cgaggaggcg acggcggctg gaggggctcc              2030
```

<210> SEQ ID NO 12
<211> LENGTH: 3621
<212> TYPE: DNA
<213> ORGANISM: Plutella xylostella

<400> SEQUENCE: 12

```
atgggggcg tggagcaatc ctgttacact ctcatcaact tcccaaccga tgcagagcca     60
tacaatgaac tgcaactcaa gattgacttg gagagaggtg acatcaagaa gaagattgag    120
gctctaaaga aggtgattgg tatcatcctc tccggggaga agatacctgg tatcctcatg    180
gtcatcatca ggtttgtgct gccgctgcag gaccatacca tcaagaagct gctactgatc    240
ttctgggaga tcgtcccgaa gaccaccccc gacggcaagc tgctgcagga gatgatcctc    300
gtctgtgact cgtacaggaa ggacctgcaa caccctaacg agttcatccg cggctccacc    360
ctccggttcc tgtgcaagct gaaggagccc gagctgctgg agccgctgat gccggcgatc    420
agggcctgcc tcgagcaccg ccactcgtat gtgcggagga acgccgtgct ggccatcttt    480
accatctacc gactccggtt cctgtgcaag ctgaaggagc ccgagctgct gaagccgctg    540
atgccggcga tcagggcctg cctcgagcac cggcactcgt atgtgcggag gaacgccgtg    600
ctggctatat ttaccatcta ccgaaacttc gacttcctca tcccggacgc tccggaactg    660
atcggcaagt tcttagagac ggaacaggac atgtcgtgca agcggaacgc tttcctgatg    720
ttgctacatg ctgagcagga gcgtgcattg agctacctgg ctgatagatt ggacagtgtg    780
gcgggcttcg gggatatact gcaactggtc attgtggagc ttatttataa ggtgtgccac    840
gcgaacccgt ccgaacgctc gcgcttcatc cgcacagtgt atgggctgct caacgcgccc    900
agcgccgcgg tccggtacga ggcggccggc acgctggtca cgctgtctac tgcgcctgcc    960
gctattaagg cggcagcatc ctgctacatc gacctcatag tcaaagaatc tgacaacaac   1020
```

```
gtgaagctaa tcgttctctc ccgtctcgga gccctacgac agggcgaggc ggcggcgcgc   1080
gcgctgcccg cgctggctat ggacgtgctg agggtgctgc aatcggctga tttggatgtc   1140
cgtgctcagg ctttacaact ggtgaagctg atagtgctct ctcggctcgg agccctacga   1200
caaggcgagg cggcggcgcg cgcgctgccc gccctcgcca tggacgtgct tagggtgctg   1260
cagtctgcgg atttggatgt gcgtgctcag gccctacagt tagccctgga cctcgtaacc   1320 cccggcacg cggacgagct agtacaagtg ctgcgcaagg aggcggcgcg cgccaccagc   1380
gccgacagcg accacgccgc ccagtaccgc cagctgctgg tgcgcgcgct gcacaaggcc   1440
gcgctgcagt tcccagaagt ggccggcagc gtggcgcccg cgctgctgga gctgctcggg   1500
gacggcagcg agccggccgc gcccgacgtg ctgctgttca ctagagaggc cctgcagacc   1560
ttcccggacc tccggggca gatctaccag tgtcatatat gtctgtggtc tggtactacc   1620
gatggtggtc tggtggatct gtccggtgac tatatcacac agggacagat ctgtccagta   1680
ctagagccgg ccgcgcccga cgtgctgctg ttcactagag aggctctaca gaccttcccg   1740
gacctccgcg ggcagatcta ccagcgtctc ctagactcga tcggcaactt caagggcaag   1800
cgtctgctag actcgatcgg caacatcaag gtgggcaagg tggcccgctc agctctgtgg   1860
ctactcgccc agttcgcgga cacggaggcg cgcgccgagg ccgccctggc tgccgtggcc   1920
gcctgcgtgc ccactgtagg gggggagcag gagacggatg attccgcagc gaagcaagaa   1980 gcgacggcg cgccgcggca gctggtcacc agcgacggca cttacgcgtc gcagtccgcc   2040
ttcaacctgc cctcgtccgc gtccaccgcg tcaacatcca ccaacaacct ccgctcagcc   2100
ctcacctcgg gcgactcgtt cacggccgcc tgcgcctgct ccgcgctggc caagctgtcg   2160
ctcaagcagg ccactgtgag ggacgccaac agggcgctgc acctcgctgc taggctactg   2220
gctcattata agattaatgc tggcaacggc acaaccctca cagcggacga catagagcac   2280
gcggctctct gcgccaggct cagctcgcga cgccccaagg ctcttctagg agccgccatc   2340
gatggtagtg ggaggcgct taaagcactg ctgaaggaaa ctgcggctga tgatgtggct   2400
gccaaggctc tactaggagc cgccatcgac ggcagcggag aggcgcttaa agcactgctg   2460
aaggaaactg ctgctgatga tgtggctgcc aagacagcgg ttatagtaga gctagcaggt   2520
ctatgtaagt ggctgagctc gcgacgcccc aaggctctac taggagccgc catcgatggt   2580
agtggggagg cgcttaaagc actgctgaag gaaactgctg ctgatgacgt agctgctaag   2640
gagcgcgaag cagcgtcagc caagcgcaca gtggatgtag aagaaggcat cgtgttctcg   2700
caactggcgg gcgcgggcgc cgccaacacg caccacgaca tcttcgaggt gtcgctgtcc   2760
aaggcactgg atggtcgttc cggccaaggc gaggacaaag gcaagctgtc caaggtgacg   2820
cagctgacag gcttctccga tccagtctac gcggaggcca tcgtggccgt caaccagtac   2880
gacatcgtgc tcgacgtgct ggtggttaac cagaccgacg atacgctcca gaactgcaca   2940
gtggagctag ccacgctcgg agacctgcga ttggtcgagc ggcccgcgtc ggtggtgtta   3000
gccccgcgag actacgccac cataaaggca cacgtcaagg tggcgtccac ggagaatggg   3060
atcatatttg ggaatattgt gtacgaagtg acgggcgcat ccatggaccg aggagtcgtg   3120
gttctaaacg acatccacat cgacatcgtg gactacatcc agccgccgc gtgcagcgac   3180 gccgacttcc gctccatgtg ggccgagttc gagcgggaga acaagccggc cgcgggcagc   3240
gacgccgact ccgctcaat gtgggccgcg ttcgagtggg agaacaaggt ttccgtgaac   3300
acaaacatca cagacctgaa ggaatacctg cagcacctcc tcgcttctac caacatgaag   3360
tgtctcacgc cagaaaaggc gctttccggt caatgcggct tcatggcggc caacatgtac   3420
```

```
gctagatcca tcttcggcga agacgctcta gccaacctga gcattgagcg agcgctcaac    3480
aagccggacg caccggtcgt gggtcacgtc aggatacgag ctaagagcca gggtatggca    3540
ttaagcctcg gcgacaagat caacatgatg cagaaggccg cccacaagcc gtcggcctcc    3600
ccgccgacgc ccgccgcctg a                                              3621
```

```
<210> SEQ ID NO 13
<211> LENGTH: 302
<212> TYPE: RNA
<213> ORGANISM: artificial sequence
<220> FEATURE:
<223> OTHER INFORMATION: synthetic construct

<400> SEQUENCE: 13
gugccguuga gauuggauau caagaggaag cugacggcuc gcucggaccg cgugaagugc     60
guggaccagc accccucgga gcccuggcug cuaugcuccc uguacaaugg ggaugucaac    120
auauggaacu acgagacaca gcugcaaaua aaaagauuug agguaugcga cuugccaguc    180
cgugcggcca aguuugugcc gaggaaguuc ugggugauca ccggcuccga ugacaugcaa    240
auucgugucu caacuacaa cacacuggaa cguguacaca auuuugaagc ucauucagac     300
uc                                                                  302
```

```
<210> SEQ ID NO 14
<211> LENGTH: 298
<212> TYPE: RNA
<213> ORGANISM: artificial sequence
<220> FEATURE:
<223> OTHER INFORMATION: synthetic construct

<400> SEQUENCE: 14
ggcaaaacau ccguaagcug aucaaggaug guuugaucau caaaaagccu guggcugucc     60
acuccagagc ccgcguccgu aaaaacacag aagccagacg gaagggucgu cauuguggcu    120
ucgguaagag gaagggguacc gccaacgcca gaaugccugu gaagguccug ugggucaaca   180
gaaugagagu ccugcgacgg uccuuaaaaa aauacagaga agccaagaag aucgauaggc    240
aaauguacca cgaccuuuac augaaagcca aagguaacgu cuucaaaaac aagagggu      298
```

```
<210> SEQ ID NO 15
<211> LENGTH: 300
<212> TYPE: RNA
<213> ORGANISM: artificial sequence
<220> FEATURE:
<223> OTHER INFORMATION: synthetic construct

<400> SEQUENCE: 15
ggugccuucg gcguguggaaa aacugucauc ucacaagcuc uguccaaaua cucaaacucu     60
gacgucauca uuuacgucgg augcggugaa cguguaacg aaauguuuga gguauugaga     120
gauuuccccg aacucacagu ugagauugac ggguaacg agccaucau gaagcguacu       180 gcucuggucg ccaacacauc caacaugccu guagcugcuc gagaagcuuc cauuuauacu    240
gguaucacau uguccgaaua cuuccgugac augggguuaca acgugucgau gauggcugac   300
```

```
<210> SEQ ID NO 16
<211> LENGTH: 300
<212> TYPE: RNA
<213> ORGANISM: artificial sequence
<220> FEATURE:
<223> OTHER INFORMATION: synthetic construct
```

<400> SEQUENCE: 16

```
gacaucaaga gaaagcuguc ugcucgauca gaccguguga aaugugucga ucugcaccca      60
acugagcccu ggauguuggc uucucucuac aacggaaacg uucacauuug gaaccacgaa     120
acucaacagc uucugaaauc cuucgaagua ugcgagcuuc caaucagggc ugcaguuuuc     180
guaccgagga agaacugggu ggucacaggc ucggacgaca ugcacguucg ugucuucaac     240
uacaacacuc ucgagcgugu acauccuuc gaggcccauu cugauuauuu gagaugcauc      300
```

<210> SEQ ID NO 17
<211> LENGTH: 300
<212> TYPE: RNA
<213> ORGANISM: artificial sequence
<220> FEATURE:
<223> OTHER INFORMATION: synthetic construct

<400> SEQUENCE: 17

```
ggaggagacu uguacgguau cguacacgag aacacauugg uuaagcauaa gauguugauc      60
ccacccaagg ccaagggguac cgucaccuac aucgcgcccu ccggcaacua caaagucacu    120
gacguagugu uggagacgga guucgacggc gagaaggaga aguacaccau guugcaagua     180
uggccggugc gccagccccg ccccgucacu gagaagcugc ccgccaacca cccccugcuc     240
accggacaga gagugcucga cucucucuuc ccuugugucc agggugguac cacggccauc     300
```

<210> SEQ ID NO 18
<211> LENGTH: 301
<212> TYPE: RNA
<213> ORGANISM: artificial sequence
<220> FEATURE:
<223> OTHER INFORMATION: synthetic construct

<400> SEQUENCE: 18

```
ggaucauauc uaccagaaac uguuggaggc ggugcccggu aucaaagugg uaagauagcg      60
cggucugcgc uguggcugcu ggcccaguuc gcugagacuc cggaacgcgc caaggaugcc    120
uuggauguac ucgccaacgu cauaccuucc cuuagcggac aagaggauaa ggaagaaucc     180
gagucggcag cuaaggccca ggacacuuca gcuccacgac agcuugucac cagugaugga     240
acuuaugcuu cgcagucugc uuuuaacuug ccaguuagcc aagcggcucc aacccacgcg    300
c                                                                     301
```

<210> SEQ ID NO 19
<211> LENGTH: 301
<212> TYPE: RNA
<213> ORGANISM: artificial sequence
<220> FEATURE:
<223> OTHER INFORMATION: synthetic construct

<400> SEQUENCE: 19

```
ggcguucucc uucuaugauu gggagaacuu ggaguugauc agacggauug agauccagcc      60
gcggcacgug uacuggucgg agagcggcaa ccuggugugc cuggcggcug augacucgua    120
cuacgugcuc aaguauaaug cagcuguugu gacgcgagcu cgcgaaacca acuccaacau     180
cacagaagac ggcaucgaag acgcuuuuga ggucgugggu gcagugaacg agguggugaaa   240
gacaggacua uggguggggcg acugcuucau cuacacgaau uccuugaaca gaauaaacua    300
c                                                                     301
```

<210> SEQ ID NO 20
<211> LENGTH: 302

<212> TYPE: RNA
<213> ORGANISM: artificial sequence
<220> FEATURE:
<223> OTHER INFORMATION: synthetic construct

<400> SEQUENCE: 20
gcguccaggg cggcaccacg gccaucccccg gggccuucgg uugcggcaag accgucaucu    60
cgcaggcguu guccaaguac uccaacucug acgucaucgu cuaugucggg uggggagc     120 gugguaacga gauguccgaa guacugcgug acuuccccga gcugacaguc gagaucgacg   180
gcgugaccga guccaucaug aagcgcacgg cgcucguggc caacaccucc aacaugccag   240
uggccgcccg agaggccucc aucuacaccg gaauuacccu auccgaauac uuccgugaca   300
uc                                                                  302

<210> SEQ ID NO 21
<211> LENGTH: 301
<212> TYPE: RNA
<213> ORGANISM: artificial sequence
<220> FEATURE:
<223> OTHER INFORMATION: synthetic construct

<400> SEQUENCE: 21
ggccgcuaaa ggacaucaac gagcucacgc agagcaucua caucccccaag ggggugaacg   60 ugcccgcgcu ggcccgcgac accgaguggc aguucaaccc gcaguacauc aaggucggca   120
cccacaucac cggcggagac uuguacggga ucgugcacga aacacgcug gugaagcacc    180 gcaugcuggu gccgcccaag gccaagggca ccgucaccua caucgcgccc gagggggaacu 240 acaaagucac ugacguggguc cuagagaccg aguucgacgg cgagaaguccc uccuacacca  300 c                                                                   301

<210> SEQ ID NO 22
<211> LENGTH: 257
<212> TYPE: RNA
<213> ORGANISM: artificial sequence
<220> FEATURE:
<223> OTHER INFORMATION: synthetic construct

<400> SEQUENCE: 22 gcauccccccc agaucagcag agguugaucu uugccggcaa gcaguuggaa gacggacgua   60
cuuugucuga cuacaacauc caaaaagaau ccacucucca ccuggucuug agauugagag   120
guggcaugca gaucuucgug aagacccuca caggaaagac caucacucuu gaggucgagc   180
cuucugacac caucgaaaac gucaaggcua aaauucaaga caaggaaggu auuccuccag   240
aucagcagag auugauc                                                  257

<210> SEQ ID NO 23
<211> LENGTH: 300
<212> TYPE: RNA
<213> ORGANISM: artificial sequence
<220> FEATURE:
<223> OTHER INFORMATION: synthetic construct

<400> SEQUENCE: 23
gcaggcacaa acagaaaaaa uuaaggaaaa uacagaaaag aucaaguga acaaaacuuu    60 accauauuua guaucuaaug ugauagaguu gcuugauguu gauccagagg aaacugagga   120
agauggugcu guuguugacc uugaugcccg ucguaaagga aaaugugcug ucauuaaaac   180
aucaacgagg cagacuuuau uuuugccagu aauaggcuua guugaugcug aaaaguuaaa   240

```
gccaggugau cugguuggag uaaacaaaga uucuuauuua auucuugaaa ccuugccugc    300
```

<210> SEQ ID NO 24
<211> LENGTH: 300
<212> TYPE: RNA
<213> ORGANISM: artificial sequence
<220> FEATURE:
<223> OTHER INFORMATION: synthetic construct

<400> SEQUENCE: 24

```
guugauuuuu gcagguaaac agcucgaaga uggucguaca uugucugacu auaauauuca     60
aaaggaaucu acucugcauu ugguccuucg ucugagagga ggaaugcaaa uuuuuguaaa    120
aaccuugacu gggaaaacua uuacauuaga aguggaaccu ucugcacacua uugaaaaugu   180
uaaagcuaaa auucaagaua aggaaggaau uccaccagau cagcagcgau ugaucuuugc    240
uggaaaacag uuggaagaug gucguacuuu aucgauuauu aacauucaga aggaaucaac    300
```

<210> SEQ ID NO 25
<211> LENGTH: 302
<212> TYPE: RNA
<213> ORGANISM: artificial sequence
<220> FEATURE:
<223> OTHER INFORMATION: synthetic construct

<400> SEQUENCE: 25

```
gacacuuacu gguaaaacaa ucacacuuga aguugagccu ucagacacaa uugaaaaugu     60
gaaagcuaaa auucaagaua aagaaggaau uccuccagau cagcagaggu ugauuuuugc    120
agguaaacag cucgaagaug gucguacauu gucgacuau aauauucaaa aggaaucuac    180
ucugcauuug guccuucguc ugagaggagg aaugcaaauu uuuguaaaaa ccuugacugg   240
gaaaacuauu acauuagaag uggaaccuuc ugacacuauu gaaauguua aagcuaaaau   300
uc                                                                  302
```

<210> SEQ ID NO 26
<211> LENGTH: 302
<212> TYPE: RNA
<213> ORGANISM: artificial sequence
<220> FEATURE:
<223> OTHER INFORMATION: synthetic construct

<400> SEQUENCE: 26

```
gaccuugacu ggcaagacca ucacucuuga ggucgagccc ucugacacca uugaaaacgu     60
caaggccaag auccaggaca aggaagguau ccccccagau cagcagaggu ugaucuucgc    120
uggcaagcag cucgaggaug gucguacccu cucggacuac aacauccaga aggaguccac    180
ccuucaucuu guccuccguc ugcguggugg uaugcagauu uucgucaaga ccuugacugg    240
caagacgauc acuuuggaag ucgagcccuc ugacaccauu gagaauguca aagccaaaau    300
cc                                                                  302
```

<210> SEQ ID NO 27
<211> LENGTH: 300
<212> TYPE: RNA
<213> ORGANISM: artificial sequence
<220> FEATURE:
<223> OTHER INFORMATION: synthetic construct

<400> SEQUENCE: 27

```
gagaagaacu cuucacugga guuggucca guucuuguug aauuagaugg cgauguuaau      60
gggcaaaaau ucucugucag uggagagggu gaaggugaug caacauacgg aaaacuuacc   120
```
cuuaauuuua uuugcacuac ugggaagcua ccuguuccau ggccaacacu ugucacuacu    180
uucucuuaug guguucaaug cuucucaaga uacccagauc auaugaaaca gcaugacuuu    240
uucaagagug ccaugcccga agguuaugua caggaaagaa cuauauuuuu caaagaugac    300

<210> SEQ ID NO 28
<211> LENGTH: 302
<212> TYPE: RNA
<213> ORGANISM: artificial sequence
<220> FEATURE:
<223> OTHER INFORMATION: synthetic construct

<400> SEQUENCE: 28
ggcgugccua cuauaggggg ggagcaagag cagacugagg auuccgcagc gaagcaggag     60
gcgacggcgg cgccgcggca gcuggucacc agcgacggga cuuacgccuc gcaguccgcc    120
uucaaccugc ccucguccgc cgccaccgca ucaacaucca caacgggcu ccgcucagcg    180 cucaccucgg gcgacucguu cacggccgcc ugcgccugcu ccgcgcuggc caagcugucg    240
cucaagcagg ccacugugag ggacgccaac agggcgcugc accucgcugc uaggcuacug    300
gc                                                                   302

<210> SEQ ID NO 29
<211> LENGTH: 300
<212> TYPE: RNA
<213> ORGANISM: artificial sequence
<220> FEATURE:
<223> OTHER INFORMATION: synthetic construct

<400> SEQUENCE: 29
gcaucuacau ccccaagggg gugaacgugc ccgcgcuggc ccgcgacacc gagugggagu     60
uccacccgca guacaucaag gucggcaccc acaucaccgg cggagacuua uacgggaucg    120
ugcacgagaa cacgcugguu aagcaccgca ugcugguugcc gcccaaggcc aagggcaccg    180
ucaccuacau cgcgcccgag gggaacuaca aagucacuga cguggccua gagaccgagu    240 ucgacggcga aagucccucc uacaccaugc uucaagugug gccggugaga cagccgcggc    300

<210> SEQ ID NO 30
<211> LENGTH: 302
<212> TYPE: RNA
<213> ORGANISM: artificial sequence
<220> FEATURE:
<223> OTHER INFORMATION: synthetic construct

<400> SEQUENCE: 30
gugccguuga gauuggauau caagaggaag cugacggcuc gcucggaccg cgugaagugc     60
guggaccagc accccucgga gcccuggcug cuaugcuccc uguacaaugg ggaugucaac    120
auauggaacu acgagacaca gcugcaaaua aaaagauuug agguaugcga cuugccaguc    180
cgugcggcca aguuugugcc gaggaaguuc uggugauca ccggcuccga ugacauguaa    240
auucgugucu ucaacuacaa cacacuggaa cguguacaca auuugaagc ucauucagac    300 uc                                                                   302

<210> SEQ ID NO 31
<211> LENGTH: 300
<212> TYPE: RNA
<213> ORGANISM: artificial sequence
<220> FEATURE:
<223> OTHER INFORMATION: synthetic construct

<400> SEQUENCE: 31

| ggugccuucg gcuguggaaa aacugucauc ucacaagcuc ugaccaaaua cucaaacucu | 60 |
|---|---|
| gacgucauca uuuacgucgg augcggugaa cgugguaacg aaauguuuga gguauugaga | 120 |
| gauuucccg aacucacagu ugagauugac ggaguaacug agaccaucau gaagcguacu | 180 |
| gcucuggucg ccaacacauc caacaugccu guugcugcuc gagaagcuuc cauuuauacu | 240 |
| gguaucacau uguccgaaua cuuccgugac auggguuaca acgugucgau gauggcugac | 300 |

<210> SEQ ID NO 32
<211> LENGTH: 300
<212> TYPE: RNA
<213> ORGANISM: artificial sequence
<220> FEATURE:
<223> OTHER INFORMATION: synthetic construct

<400> SEQUENCE: 32

| gacaucaaga gaaagcuguc ugcucgauca ggccguguga aaugugucga ucugcaccca | 60 |
|---|---|
| acugagcccu ggauguuggc uucucucuac aacggaaacg uucacauuug gaaccacgaa | 120 |
| acucaacagc uucugaaauc cuucgaagua ugcgagcuuc caaucagggc ugcaguuuuc | 180 |
| guaccgagga agaacuggu ggucacaggc ucggacgaca ugcacguucg ugucuucaac | 240 |
| uacaacacuc ucgagcgugu acauuccuuc gaggcccauu cugauuauuu gagaugcauc | 300 |

<210> SEQ ID NO 33
<211> LENGTH: 300
<212> TYPE: RNA
<213> ORGANISM: artificial sequence
<220> FEATURE:
<223> OTHER INFORMATION: synthetic construct

<400> SEQUENCE: 33

| ggaggagacu uguacgguau cguacacgag aacacauugg uuaagcauaa gauguugauc | 60 |
|---|---|
| ccacccaagg ccaaggguac cgucaccuac aucgcgcccu ccggcaacua caaagucacu | 120 |
| gacguagugu uggagacggu guucgacggc gagaaggaga aguacaccau guugcaagua | 180 |
| uggccgguc gccagccccg ccccgucacu gagaagcugc ccgccaacca ccccgcugcuc | 240 |
| accggacaga gagugcucga cucucucuuc ccuuguagucc aggugguac cacgccauc | 300 |

<210> SEQ ID NO 34
<211> LENGTH: 301
<212> TYPE: RNA
<213> ORGANISM: artificial sequence
<220> FEATURE:
<223> OTHER INFORMATION: synthetic construct

<400> SEQUENCE: 34

| ggaucauauc uaccagaaac uguuggaggc ggugcccggu aucaaagugg uaagauagcg | 60 |
|---|---|
| cggucugcgc uguggcugcu ggcccaguuc gcugagacuc cggaacgcgc caaggaugcc | 120 |
| uuggauguac ucgccaacgu cauaccuucc cuuagcggac aagaggauaa agaagaaucc | 180 |
| gagucggcag cuaaggccca ggacacuuca gcuccacgac agcuugucac cagugaugga | 240 |
| acuuaugcuu cgcagucugc uuuuaacuug ccaguuagcc aagcggcucc aacccacgcg | 300 |
| c | 301 |

<210> SEQ ID NO 35
<211> LENGTH: 302
<212> TYPE: RNA
<213> ORGANISM: artificial sequence

```
<220> FEATURE:
<223> OTHER INFORMATION: synthetic construct

<400> SEQUENCE: 35
gcguccaggg cggcaccacg gccaucccccg gggccuucgg uagcggcaag accgucaucu    60
cgcaggcguu guccaaguuc uccaacucug acgucaucgu cuaugucggg uguggggagc   120
gugauaacga gauguccgaa guacugcgug acuucccccga gcugacaguc gagaucgacg   180
gcgugaccga guccaacaug aagcgcacgg cgcucguggc caacaccucc aacaugccag   240
uggccgcccg agaggccucc aucuacaccg gaauuacccu auccgaauac uuccgugaca   300
uc                                                                  302

<210> SEQ ID NO 36
<211> LENGTH: 257
<212> TYPE: RNA
<213> ORGANISM: artificial sequence
<220> FEATURE:
<223> OTHER INFORMATION: synthetic construct

<400> SEQUENCE: 36
gcaucccccc agaucagcag agguuaaucu uugccggcaa gcaguuggaa gacggacgua    60
cuuugucuga uuacaacauc caaaaagaau ccacucucca ccuggucuug agauugagag   120
guggcaugca gaucuucaug aagacccuca caggaaagac caucucucuu gaggucgagc   180
cuucugacac caucgaaaac gucaaggcua aaauucaagg caaggaaggu auuccuccag   240
auuagcagag auugauc                                                  257

<210> SEQ ID NO 37
<211> LENGTH: 300
<212> TYPE: RNA
<213> ORGANISM: artificial sequence
<220> FEATURE:
<223> OTHER INFORMATION: synthetic construct

<400> SEQUENCE: 37
gcaggcacaa acagaaaaaa uuaaggaaaa uacagaaaag aucaaaguga acaaaacuuu    60
accguauuua gaaucuaaug ugauagaguu gcuugauguu gauccagagg aaacugagga   120
agauggugcu auuguugacc uugaugcccg ucguaaagga aaaugugcug ucauuaaaac   180
aucaacgagg cagacuuauu uuuugccagu aauaggcuua guugaugcug aaaaguuaaa   240
gccaggugau cugguuggag uaaacaaaga ucuuauuug auucuugaaa ccuugccugc   300

<210> SEQ ID NO 38
<211> LENGTH: 300
<212> TYPE: RNA
<213> ORGANISM: artificial sequence
<220> FEATURE:
<223> OTHER INFORMATION: synthetic construct

<400> SEQUENCE: 38
guugauuuuu gcagguaaac agcucgaaga uggucguaca uugucugacu auaauauuca    60
aauggaaucu acucugcauu uggccuuucg ucugagagca ggaaugcaaa uauuuguaaa   120
aaccuugacu gggaaaacua uuacauuaga auggaaccu ucugacacua uugaauaugu   180
uaaagcuaaa acucaggaua agguaggaau ucaccagau caguagcgau ugaucuuugc   240
uagaaaacag uuggaagaug gucauacuuu aucugauuau aacauucaga uggaaucaac   300

<210> SEQ ID NO 39
```

```
<211> LENGTH: 302
<212> TYPE: RNA
<213> ORGANISM: artificial sequence
<220> FEATURE:
<223> OTHER INFORMATION: synthetic construct

<400> SEQUENCE: 39
gacacuuacu gguaaaacaa ucacacuuga aguugagccu ucagacacaa uugaaaaugu      60
gaaaguuaaa auucaagaua aaguaggaau uccuccaguu cagcagaggu ugauuuuugc     120
agguaaacag cucgaagaug gucguacauu gucgacuau aauauucuaa aggaaucuac     180
ucugcauuug guccuucguc ugagaagagg aaugcaaauu guuguaaaaa ccuugacugg    240
gaaaacuauu acauuagaag uggaaccuuc ugacacuauu gaaauuguua aagcuaaaau    300
uc                                                                   302

<210> SEQ ID NO 40
<211> LENGTH: 302
<212> TYPE: RNA
<213> ORGANISM: artificial sequence
<220> FEATURE:
<223> OTHER INFORMATION: synthetic construct

<400> SEQUENCE: 40
gaccuugacu ggcaagacca ucacucuuga ggucgagccc ucugacacca uugaaaacgu     60
caaggccaag auccagaaca aggaagguau cccccagau cagcagaggu uggucuucgc    120
uggcaagcag cucgaggaug gucguacccu cucggacuac aacaucuaga aggaguccac   180
ccuucaucuu guccuccguc ugcguggugg caugcagauu uucgcaaga ccuugacugg    240 caagacgauc acuuuggaag ucgagcccuc ugacaccauu gagaguguca aagccaaaau   300
cc                                                                   302

<210> SEQ ID NO 41
<211> LENGTH: 300
<212> TYPE: RNA
<213> ORGANISM: artificial sequence
<220> FEATURE:
<223> OTHER INFORMATION: synthetic construct

<400> SEQUENCE: 41
gagaagaacu cuucacugga guuggucccca guucuuguug aauuagaugg cgauguuaau     60
gggcaaaaau ucucugucag uggugagggu gaaggugaug caacauacgg aaaacuuacc    120
cuuaauuuua uuugcacuac ugggaagcua ccuguuccau ggccaacacu ugucacuacu    180
uucucuuaug guguucaaug cuucucaaga uacccagauc auaugaaaca gcaugacuuu   240
uucaagagug ccaugcccga agguuaugua caggaaagaa cuauauuuuu caaagaugac   300

<210> SEQ ID NO 42
<211> LENGTH: 302
<212> TYPE: RNA
<213> ORGANISM: artificial sequence
<220> FEATURE:
<223> OTHER INFORMATION: synthetic construct

<400> SEQUENCE: 42
ggcgugccua cuauaggggg ggagcaagag cagacugagg auuccgcagc gaagcaggag     60
gcgacggcgg cgccgcggca gcuggucacc agcgacggga cuuacgccuc gcaguccgcc   120
uucaaccugc ccucguccgc cgccaccgca ucaacaucca caacgggcu ccgcucagcg    180 cucaccucgg gcgacucguu cacggccgcc ugcgccugcu ccgcgcuggc aaagcugucg    240
```
cucaagcagg ccacugugag ggacgccaac agggcgcugc accucgcugc caggcuacug    300
gc                                                                    302

<210> SEQ ID NO 43
<211> LENGTH: 3005
<212> TYPE: DNA
<213> ORGANISM: Lygus hesperus

<400> SEQUENCE: 43
agcacagctc agaaagttga agctctcaag aaaacgattc acatgatttc caacggcgag     60
cgtttaccgg gtcttctgat gcatatcatc agattcattc tgccttccca ggaccacacg    120
atcaaaaagt tgctgctaat attctgggag atcgttccta aaacttaccc cgatggaaaa    180
ctgcttcaag aaatgatact tgtttgcgac gcctacagaa aggatttaca acaccccaat    240
gagttcgtgc gcgggtcgac tttgagattc ctctgcaaat tgaaggagcc agaacttctg    300
gaaccgctga tgcctgccat tcggtcgtgc ctcgagcaca gagtgtctta cgtccgcagg    360
aacgctgtcc ttgccatttt cacgatctac aagaatttcg aatttctaat ccctgatgct    420
cccgaactca ttgccaattt cctcgacgga gagcaagata tgtcttgcaa aaggaatgcc    480
ttcttgatgc tcctccacgc tgaccaagac agagcactct cctatcttgc ttcttgtctg    540
gaccaagtca ccagctttgg tgacatcctc cagcttgtca tcgttgaatt gatttacaag    600
gtttgtcatg cgaatccctc agaacgttct cggttcataa ggtgcatata caacctattg    660
aattcaagca gccctgctgt ccgatatgaa gctgctggta cgctgataac cctgtccaac    720
gcacctactg ccatcaaggc tgctgcatca tgctacattg atctaatcat caaggaaagc    780
gataacaacg tcaaactgat cgtcctcgat cgcctggtcg ccctcaaaga catcccgacg    840
tacgaaagag tcttgcagga tctcgtcatg gacatcctcc gcgtcttggc cagcccggat    900
atggaagtca ggaagaaggc tttgaatctc gctcttgatc ttacaacttc gcgttgtgtc    960
gaagaagtag ttttgatgct gaagaaagag gttgccaaaa ctcataactt gtccgagcac   1020
gaggaaacag gaaaatatag gcaactcctt gtgagaactc tgcactcttg cagtatgaaa   1080
ttccctgatg tggctgcttc cgtcatccca gtgctcatgg aattttttgtc tgactccaac   1140 gagctcgctt cccaagacgt ccttattttc gtaagggaag ccattcacaa atttgaaaat   1200
ctgaggaaca caatcattga gaaattgctt gaagcttttc cgtccataaa gttcgtcaaa   1260
gtccatcgtg ctgcgttgtg gatattagga gagtacgctg cttccatcga tgacgtcaga   1320
gctgtcatga aacaaatcaa acagaatttg ggtgaggttc ctatggtgga agatgaaatg   1380
aagcgggccg ctggagagaa gacagaagag tcatctgaac agaacagcgg gggtgcaatg   1440
ccgtcaagcg cttccaaact agtaacgtct gatgggacct atgcttctca gtctgtgttc   1500
agcactgtat ccacatccaa aaaagaggac cgaccacctt tgaggcagta tctgattgat   1560
ggtgattatt ttattggctc caccatcgcg tccactttgg tgaaactttc tctgaagttt   1620
gacaacttgg aatccaacac ggctgcgcag aacgaattct gcaatgaatg catgctgatc   1680
atcgcctgca ccctccatct tggaagatct ggcctttgca caagaatttt gaataacgac   1740
gacgctgaga ggatgctgtt ttgtcttcga gttcttgggg atggaagccc aaccattgag   1800
aagattttta ctcaagaatg ccgagaagct cttgcgtcta tgcttaccgc tcaacaccat   1860
gaggaaatcg ccttgaataa ggccaaagaa aagaccgcac atctcatcca cgtagacgac   1920
ccagtctcat tcctgcaatt atcatctctg agaaactctg aacttggttc tgaaaacgtg   1980

```
ttcgagctaa gtcttactca ggcgcttggt ggtcccacca gtggtggctc ctccaactcg    2040
gacctcttct tctctgccag caagctcaac aaagtcacgc agcttactgg cttttctgac    2100
cctgtctacg ctgaagctta cgtccaagtc aaccagtatg atatcgtctt ggacgtactc    2160
attgtcaacc agacagctga cactcttcaa aattgcactc tggaattggc tacacttggc    2220
gacctgaaat tggtcgagaa gccgcaaccc tgcgttttgg cgcctcatga cttctgtaac    2280
ataaaagcta acgtcaaagt ggcttccact gaaaacggaa ttattttttgg caacattgtt   2340 tacgacgtta gtggagcagc ttccgaccga aacgtcgtcg tcctcaatga cattcacatc    2400
gatattatgg actacatagt tcctgcatct tgttctgaca ctgaattccg ccaaatgtgg    2460
gctgaattcg aatgggaaaa caaggtatct gtcaacacca acctcacgga cttgcacgag    2520
tatttggccc atttggtcag gagcaccaac atgaagtgct tgacaccaga gaaagcgctc    2580
tgcggtcaat gtgggttcat ggctgccaac atgtatgcgc gctcgatttt cggagaagat    2640
gcgttggcga acctgagcat cgagaaaccc ttcaacaagc tgatgcacc tgtcactgga     2700 cacatccgca tccgagccaa aagccaggga atggcactca gtctgggaga caaaatcaac    2760
atgacccaga agagaccgca gaaaatgtac ggtgcctaag ccctcataga tcccaccacc    2820
tcggttcaac tctccatctc ctttgtgaga gcaccctact gcttacctgc gccacactgc    2880
aagtaaactt ggcttcggcc tcctatttat catattttac ggtattcttt gttatcgaaa    2940
tatttatgca tattatatta ttggtatttc gttatcccaa ttcattcaat aaatatatag    3000
attaa                                                                3005

<210> SEQ ID NO 44
<211> LENGTH: 1623
<212> TYPE: DNA
<213> ORGANISM: Lygus hesperus

<400> SEQUENCE: 44
gccattagag cttcagacga gaaacgagaa cgagctacgt tgagcatcaa gagcttttgt      60
actattgaaa ttgtgaaaaa tgcagatctt cgttaaaact ttgactggga agaccatcac     120
cctcgaggtc gagccttctg ataccattga aaacgtgaag gcgaaaattc aggataaaga     180
aggcatcccc ccagatcagc agaggttgat cttttgccggc aagcagttgg aagacggacg    240
tactttgtct gactacaaca tccaaaaaga atccactctc cacctggtct tgagattgag     300
aggtggcatg cagatcttcg tgaagaccct cacaggaaag accatcactc ttgaggtcga     360
gccttctgac accatcgaaa acgtcaaggc taaaattcaa gacaaggaag gtattcctcc     420
agatcagcag agattgatct cgccggcaa acaactcgaa gatggccgta ccctctctga     480
ctacaatatt caaaaagagt ccacccttca cttggtgttg agattgcgtg gaggtatgca     540
aatctttgtc aaaacattga ctggaaagac catcacccctt gaagtcgaac cctccgacac    600
catcgaaaat gtcaaggcca gatccagga caaggaaggc atcccccag atcagcagag       660 gttgattttc gctggcaaac aacttgaaga cggacgtacc ctctcggact acaacatcca     720
gaaggagtcg accctccatc ttgtcctccg tctgcgtggt ggtatgcaga ttttgtcaa      780 aactctgact ggcaagacaa tcacccttga agtagagccc tctgacacca tcgaaaatgt     840
caaggcgaaa atccaggaca agaaggcat cccccagat cagcagaggt tgatcttttgc      900 cggtaagcag cttgaagacg gccgcaccct ctcggactac aacatccaga aggagtccac     960
ccttcatctt gtcctccgtc tgcgtggtgg tatgcagatc ttcgtcaaga ccttgactgg    1020
caagacgatc actttggaag tcgagccctc tgacaccatt gagaatgtca aagccaaaat    1080
```

```
ccaagataag gaaggcatcc ccccagatca gcagaggttg atcttcgctg gtaagcaact    1140
tgaagacggc cgcaccctct ctgactacaa catccagaag gagtcgaccc tccatcttgt    1200
cctccgtctg cgtggtggta tgcagatctt cgtcaagacc ttgacaggca agaccatcac    1260
ccttgaagtc gagccctctg acaccatcga aacgtcaag gctaagatcc aggacaagga     1320
aggtatcccc ccagatcagc aaagattgat cttcgccggc aaacagctcg aagatggccg    1380
taccctctca gactacaaca ttcaaaagga gtcaactctt catctcgttc tgaggctccg    1440
tggcggtcgt tattgatcac aattccaaac ttaaaaattg cattccgatt ttccttcttt    1500
atttggcaaa aaatacatac cctagttaat taaaatgact tgaaatttga ttttttaaga    1560
atgcttcaaa ttttttata gatggtttgt tacatagaca atacacaaca tgttgaaagc     1620
aat                                                                  1623

<210> SEQ ID NO 45
<211> LENGTH: 301
<212> TYPE: RNA
<213> ORGANISM: artificial sequence
<220> FEATURE:
<223> OTHER INFORMATION: synthetic construct

<400> SEQUENCE: 45
guugcugcua auauucuggg agaucguucc uaaaacuuac cccgauggaa aacugcuuca     60
agaaaugaua cuuguuugcg acgccuacag aaaggauuua caacaccccca augaguucgu    120 gcgcgggucg acuuugagau uccucugcaa auugaaggag ccagaacuuc uggaaccgcu    180
gaugccugcc auucggucgu gccucgagca cagagugucu acguccgca ggaacgcugu      240 ccuugccauu uucacgaucu acaagaauuu cgaauuucua auccccugaug cucccgaacu    300 c                                                                    301

<210> SEQ ID NO 46
<211> LENGTH: 255
<212> TYPE: RNA
<213> ORGANISM: artificial sequence
<220> FEATURE:
<223> OTHER INFORMATION: synthetic construct

<400> SEQUENCE: 46
gacguacuuu gucugacuac aacauccaaa aagaauccac ucuccaccug gucuugagau     60
ugagaggugg caugcagauc uucgugaaga cccucacagg aaagaccauc acucuugagg    120
ucgagccuuc ugacaccauc gaaaacguca aggcuaaaau ucaagacaag gaagguauuc    180
cuccagauca gcagagauug aucuucgccg gcaaacaacu cgaagauggc cguacccucu    240
cugacuacaa uauuc                                                     255

<210> SEQ ID NO 47
<211> LENGTH: 701
<212> TYPE: DNA
<213> ORGANISM: Lygus hesperus

<400> SEQUENCE: 47
aagttttctc ttttgtaatt tttttgtaga tttttgtaca aaatacgttt tttgtttaaa     60
atttaaaaac ggagggggcg agatcacttt ttgacggcag cctcgtcttc tcgggcgtac    120
gcctgcatga tctcttgctt cttggtggcg atcctctcct cgcgcctctt cttcgcctcc    180
ttgaccttga gacgtctcgc ctctgcctgg tccttcaaca tctttgatct cgccttttca    240
```

```
gccttcttct tgtgaatgaa gtccatcagt accctcttgt ttttgaagac gttacctttg      300
gctttcatgt aaaggtcgtg gtacatttgc ctatcgatct tcttggcttc tctgtatttt      360
ttaaggagcc gtcgcaggac tctcattctg ttgacccaca ggaccttcac aggcattctg      420
gcgttggcgg tacccttcct cttaccgaag ccacagtgac gacccttccg tctggcttct      480
gtgtttttac ggacgcgggc tctggagtgg acagccacag gctttttgat gatcaaacca      540
tccttgatca gcttacggat gttttgccta gagttggtgt tggcgatttc gttgatttca      600
ttagggtcca accacacttt cttcttgccg catctcatca ccgaggcggc gagcctcttc      660
tgcagtttga gcgaactcat ggtcggacga agagaaccac c                         701

<210> SEQ ID NO 48
<211> LENGTH: 1927
<212> TYPE: DNA
<213> ORGANISM: Euschistus heros

<400> SEQUENCE: 48
aacaaacata acatgatatt attaaatgtt tcccaaattt ataaatatac aaataatata       60
aagaatcact gaaaaaaaat tttgcaacag gaagtttaat ctcctttcaa tttaatccaa      120
aaaatattaa atgcaatgaa aaaataaatt aaaaaacaaa tttgagatta gaatatattc      180
aataaactgt gaaccaacaa ataattaatt ttgaaaatga ttataaaaat aaaaattaaa      240
tattaaatct ggcagaaact catttcaaac tagtaatcaa attagtcaaa ctaataattg      300
atacagaaaa tataatcttt ttaaaattaa acaggcaaaa atatatatat atatatgaat      360
taacaaaact ttttttaactg gagttaatgc gactttaaga atttaataaa attataatgt      420
gctattttac ttgttggttt acttacacat ttgttttttca aagagtggca tatttacaag      480
ttaataacaa tacaaaatca atcacagtta ttggcactcc cgaaaagaag aatgcaagtg      540
agtttctgca ttattaaaaa aatctttatc aatagatatt taagcataat agtttaagtt      600
ggctttcttc tttgcctgca cttctaatat tgcatccatg aaatcttcat gagtgacaac      660
tccagctcct cttcgcaatg ctatcatacc tgcttccaca caaaccgctt tgcattgagc      720
tccattgaaa tcatcagttg aacgagcaag ttcttcaaaa ttaacatcaa cactaatatt      780
catcttacga gaatgaattt gcattatacg tgctcgggca tcttcgttag gatgtgggaa      840
ttcaattttt ctgtctagtc gacctgaacg caaaagggcg ggatccaaaa tatctactct      900
atttgtagct gcaataacct taatatcagc tgttgagcta aatccatcta actggttgag      960
cagttctaac atagttcttt gaacttctcg atcaccagct ttttcagaat caaatctttt     1020
tgttccaata gcatccaact cgtcaataaa gataatagca ggagatttttt ccttagcaag     1080 agcaaaagca tctctgacaa gtttggctcc atctcctata aacatctgaa caagttgggg     1140
tccagctagt ttcaaaaaag ttgatttagt ttgagctgca cacgctctag ccagtaaagt     1200 cttttcctgtt ccaggaggtc catagagcaa tacacccttta ggaggatgaa ttcctagatt     1260
ttcaaatttt tctttgtgtg tcataggaag aacaacggct tctattaatt cttgaatctg     1320
cttatcaagc ccaccgatat cagaatactg ctcagtaggt ctttcatcaa cttccattgc     1380
tttaactcgt gcatcatact cagcaggcaa ggtttcaaga attaaataag aatctttgtt     1440
tactccaacc agatcacctg gctttaactt ttcagcatca actaagccta ttactggcaa     1500
aaaataagtc tgcctcgttg atgttttaat gacagcacat tttcctttac gacgggcatc     1560
aaggtcaaca acagcaccat cttcctcagt ttcctctgga tcaacatcaa gcaactctat     1620
cacattagat actaaatatg gtaaagtttt gttcactttg atctttttctg tattttcctt     1680
```

```
aatttttct gtttgtgcct gcaactcatg actgactcgc atgacttcac ttttcatgat      1740
tttaatttca ttatcaagaa gcctaatacg actgacaatt tcatccgtag acattctcat      1800
gatttcttca cctaaagctt gctccattct ttcgtcccac aagggctttt cttctgtttt      1860
ggaagtagac atctgaattg ccgaacttag gatgtgaacc aaattaaaac ctgtaactac      1920
aacaaac                                                                1927
```

<210> SEQ ID NO 49
<211> LENGTH: 2170
<212> TYPE: DNA
<213> ORGANISM: Euschistus heros

<400> SEQUENCE: 49

```
tttttgaac ttaaagaaac tgtttatttc tagtttagtt acattgtatt tatgaaataa       60
ttataaatat aataatgaaa atgctaataa aaatatcaaa agcaatttac tgatatggaa      120
ttttgatgga atgaaatgat aagtagcctt aatatccgcc cctaagacgc aacactaaat      180
gcagagttga ttccttctgg atgttataat cagataggt acgaccatcc tctaattgtt       240
ttccagcaaa aataagcctc tgctgatctg gaggtattcc ttctttgtcc tgaattttgg      300
ctttaacatt ttcaatagtg tcagatggct caacttctaa ggtaatagtc ttgcctgtga      360
gggtcttgac aaagatctgc ataccacctc tcaatcgaag gaccagatgt agtgtagatt      420
ccttctggat attataatct gaaagggtac ggccatcttc gagttgtttt ccagcaaaga      480
tcaaacgctg ctggtcggga ggaattcctt ctttatcctg aattttagct tttacattct      540
caattgtatc agatggctct acttccaagg taatggtttt acctgtcaaa gtcttcacaa      600
agatctgcat gcctcctctt agacgaagca ccaaatgcag tgttgattcc ttttgaatgt      660
tgtaatcaga caaagttcgg ccatcttcca gctgctttcc agcaaaaata agcctctgtt      720
ggtctggtgg tattccttct ttatcttgaa ttttggcttt aacattctca atagtatctg      780
aaggctcaac ttccaaggtt atggtcttac cagttagagt ctttacaaaa atctgcatgc      840
cacctctcaa gcgaagtaca agatgaagag tagactcttt tgaatatta taatctgaaa       900 gggtacggcc atcttcaagt tgttttccag caaagatcaa acgttgctgg tctggtggaa      960
ttccttcttt gtcctggatt tttgctttta cgttctcaat agtatcagat ggttcaactt      1020
ctaaggtgat ggtcttccct gttaaagtct tgacaaagat ctgcatgcct cctcgaagtc      1080
taagtacaag atgtaaagta gattcctttt ggatgttgta atcagaaaga gtacgcccat      1140
cttctaactg ttttcctgca aagatcagcc tttgctgatc tggcggaatt ccttccttat      1200
cttgaatttt ggcttttaca ttttcaatgg tatctgacgg ttcaacttct aaagttatgg      1260
tttttccagt aagcgtctta acaaaaatct gcattccacc tcttaaacgt aatactaaat      1320
gtagtgttga ttccttctga atgttataat cagataaagt acgaccatct tccaactgtt      1380
ttccagcaaa gatcaatcgc tgctgatctg gtggaattcc ttccttatct tgaattttag      1440
ctttaacatt ttcaatagtg tcagaaggtt ccacttctaa tgtaatagtt ttcccagtca      1500 aggttttttac aaaaatttgc attcctcctc tcagacgaag gaccaaatgc agagtagatt      1560
ccttttgaat attatagtca gacaatgtac gaccatcttc gagctgttta cctgcaaaaa      1620
tcaacctctg ctgatctgga ggaattcctt ctttatcttg aattttagct ttcacatttt      1680
caattgtgtc tgaaggctca acttcaagtg tgattgtttt accagtaagt gtcttgacaa      1740
agatctgcat gcctcctctt aaacgtagga caagatgaag agtagattcc ttttgaatat      1800
```

```
tatagtcaga caatgtacga ccatcttcga gctgtttacc tgcaaaaatc aacctctgtt    1860
ggtctggagg aattccttct ttatcttgaa ttttagcttt aacattttca attgtatcag    1920
atggctccac ttccaaggtg atggttttac cagtcaaggt cttcacaaaa atttgcatgc    1980
ctcctctcaa ccgaagtact aaatgtaaag tagattcttt ttgaatattg taatctgaaa    2040
gagtacggcc atcttcaagc tgtttaccag caaaaataca acctctgttg gtctggaggg    2100
attccttctt tgtcttggat tttggccttg acattttcta ttgtgtcaga aggctcaact    2160
tctaatgtaa                                                           2170
```